US006284741B1

(12) United States Patent
Werther et al.

(10) Patent No.: US 6,284,741 B1
(45) Date of Patent: Sep. 4, 2001

(54) METHOD FOR THE PROPHYLAXIS AND/OR TREATMENT OF PROLIFERATIVE AND /OR INFLAMMATORY SKIN DISORDERS

(75) Inventors: George Arthur Werther, Camberwell; Christopher John Wraight, Blackburn, both of (AU)

(73) Assignee: Royal Children's Hospital Research Foundation, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/199,926

(22) Filed: Nov. 25, 1998

Related U.S. Application Data

(63) Continuation of application No. 08/666,392, filed as application No. PCT/AU95/00410 on Jul. 6, 1995, now Pat. No. 5,929,040.

(30) Foreign Application Priority Data

Jul. 8, 1994 (AU) .............................................. PM6725/94

(51) Int. Cl.[7] ........................ A61K 31/7088; C07H 21/00
(52) U.S. Cl. ............................. 514/44; 435/6; 435/91.31; 536/24.5
(58) Field of Search ........................... 435/6, 91.31, 375, 435/325; 514/44; 536/24.3, 24.31, 24.5

(56) References Cited

U.S. PATENT DOCUMENTS

| 5,585,479 | 12/1996 | Hoke et al. ........................ 536/24.5 |
| 5,643,788 | 7/1997 | Baserga et al. ...................... 435/325 |
| 5,929,040 | * 7/1999 | Werther et al. ....................... 514/44 |

FOREIGN PATENT DOCUMENTS

| 9422486 | 10/1994 | (WO) . |
| 9423034 | 10/1994 | (WO) . |
| 9610401 | 4/1996 | (WO) . |

OTHER PUBLICATIONS

Stein, C. A. Keeping the biotechnology of antisense in context. Nature Biotechnol. 17: 209, Mar. 1999.*

"Localization of Messenger Ribonucleic Acid for Insulin-–Like Growth Factor–Binding Proteins in Human Skin by in Situ Hybridization" by J.A. Batch et al.; Journal of Clinical Endocrinology and Metabolism; vol. 79, No. 5, pp. 1444–1449, (1994).*

"Regulation of IGFBP Secretion and Modulation of Cell Growth in MDBK cells" by W.S. Cohick et al.; pp. 20–23; University of North Carolina School of Medicine, Division of Endocrinology, (1993).*

"Episomal Expression of Sense and Antisense Insulin–like Growth Factor (IGF)–binding Protein–4 Complementary DNA Alters the Mitogenic Response of a Human Colon Cancer Cell Line (HT–29) by Mechanisms that are Independent of and Dependent upon IGF–1" by Singh et al.; Cancer Research 54, pp. 6563–6570, Dec. 15, 1994.*

"Loss of the Metastatic Phenotype in Murine carcinoima Cells Expression an Antisense RNA to the Insulin–like Growth Factor Receptor" by Long et al.; Cancer Research 55, pp. 1006–1009, Mar. 1, 1995.*

"Growth Inhibition of Human Melanoma Cells in Nude Mice by Antisense Strategies to the Type 1 Insulin–like Growth Factor Receptor" by Resnicoff et al.; Cancer Research 54, pp. 4848–4850, Sep. 15, 1995.*

"Antisense–Mediated Reduction in Insulin–Like Growth Factor–1 Receptor Expression Suppresses the Malignant Phenotype of a Human Alveolar Rhabdomyosarcoima" by Shapiro et al.; The American Society For Clinical Investigation, Inc.; vol. 94, Sep. 1994, pp. 1235–1242.*

"The Insulin–like Growth Factor 1 Receptor Is Expressed by Epithelial Cells with Proliferative Potential in Human Epidermis and Skin Appendages: Correlation of Increased Expression with Epidermal Hyperplasia" by Hodak et al.; Laboratory for Investigative Dermatology; pp. 564–570, (1996).*

Antisense '97: A roundtable on the state of the industry. Nature Biotechnology 15: 519–524, (Jun. 1997).*

Gewirtz et al. Facilitating oligonucleotide delivery: Helping antisense deliver on its promise. Proc. Natl. Acad. Sci USA 93: 3161–3163, (Apr. 1996).*

Gura. Antisense has growing pains. Science 270: 575–577 (Oct. 1995).*

Stull et al. Antigene, ribozyme and aptamer nucleic acid drugs: Progress and prospects. Pharm. Res. 12: 465–483, (Apr. 1995).*

Gouy, M. Secondary structure prediction of RNA, in Nucleic Acid and Protein Sequence Analysis: A Practical Approach, Bishop et al, eds. IRL Press, Oxford, pp. 259–284 (1987).*

* cited by examiner

*Primary Examiner*—John L. LeGuyader
*Assistant Examiner*—Thomas G Larson
(74) *Attorney, Agent, or Firm*—Baker Botts

(57) ABSTRACT

The present invention relates generally to a method for the prophylaxis and/or treatment of skin disorders, and in particular proliferative and/or inflammatory skin disorders, and to genetic molecules useful for same. The present invention is particularly directed to genetic molecules capable of modulating growth factor interaction with its receptor on epidermal keratinocytes to inhibit, reduce or otherwise decrease stimulation of this layer of cells. The present invention contemplates, in a most preferred embodiment, a method for the prophylaxis and/or treatment of psoriasis.

6 Claims, 20 Drawing Sheets

```
  1  ATTCGGGGCG  AGGGAGGAGG  AAGAAGCGGA  GGAGGCGGCT  CCCGCTCGCA
 51  GGGCCCGTGCA CCTGCCCGCC  CGCCCGCTCG  CTCGCTCGCC  CGCCGGCCG
101  CGCTGCCGAC  CGCCAGCATG  CTGCCGAGAG  TGGGCTGCCC  CGCGCTGCCG
151  CTGCCCGCGC  CGCCGCTGCT  CCGCCTGCTG  CCGCTGCTGC  TGCTGCTACT
201  GGGCGCGAGT  GGCGGCGGGG  GCGGGAGGTG  CGCGGAGGTG  CTGTTCCGCT
251  GCCCGCCCTG  CACACCCGAG  GCGGGCGCG   CCTGGGGCCC  CCCGCCGGTT
301  GCGCCCGCCCG CCGCGGTGGC  CGCAGTGGGC  CGGCAGTGGCC GCATGCCATG
351  CGCGGAGCTC  GTCCGGGAGC  CGGGCTGCGG  CTGCTGCTCG  GTGTGCGCCC
401  GGCTGGAGGG  CGAGGCGTGC  GGCGTCTACA  CCCCGCCTG   CGGCCAGGGG
451  CTGCGCTGCT  ATCCCCACCC  GGGCTCCGAG  CTGCCCCTGC  AGGCGCTGGT
501  CATGGGCGAG  GGCACTTGTG  AGAAGCGCCG  GGACGCCGAG  TATGGCGCCA
551  GCCCGGAGCA  GGTTGCAGAC  AATGGCGATG  ACCACTCAGA  AGGAGGCCTG
601  GTGGAGAACC  ACGTGGACAG  CACCATGAAC  ATGTTGGGCG  GGGGAGGCAG
651  TGCTGGCCGG  AAGCCCCTCA  AGTCGGGTAT  GAAGGAGCTG  GCCGTGTTCC
701  GGGAGAAGGT  CACTGAGCAG  CACCGGCAGA  TGGGCAAGGG  TGGCAAGCAT
```

FIG.1A

```
 751  CACCTTGGCC TGGAGGAGCC CAAGAAGCTG CGACCACCCC CTGCCAGGAC
 801  TCCCTGCCAA CAGGAACTGG ACCAGGTCCT GGAGCGGATC TCCACCATGC
 851  GCCTTCCGGA TGAGCGGGGC CCTCTGGAGC ACCTCTACTC CCTGCACATC
 901  CCCAACTGTG ACAAGCATGG CCTGTACAAC CTCAAACAGT GCAAGATGTC
 951  TCTGAACGGG CAGCGTGGGG AGTGCTGGTG TGTGAACCCC AACACCGGGA
1001  AGCTGATCCA GGGAGCCCCC ACCATCCGGG GGGACCCCGA GTGTCATCTC
1051  TTCTACAATG AGCAGCAGGA GGCTTGCGGG GCCTGCCCCC AGCGGATGCA
1101  GTAGACCGCA GCCAGCCGGT GCCTGGCGCC CCTGCCCCCC GCCCCTCTCC
1151  AAACACCGGC AGAAAACGGA GAGTGCTTGG GTGGTGGGTG CTGGAGGATT
1201  TTCCAGTTCT GACACACGTA TTTATATTTG GAAAGAGACC AGCACCGAGC
1251  TCGGCACCTC CCCGGCCTCT CTCTTCCCAG CTGCAGATGC CACACCTGCT
1301  CCTTCTTGCT TTCCCCGGGG GAGGAAGGGG GTTGTGGTCG GGGAGCTGGG
1351  GTACAGGTTT GGGGAGGGGG AAGAGAAATT TTTATTTTTG AACCCCTGTG
1401  TCCCTTTTGC ATAAGATTAA AGGAAGGAAA AGT
```

FIG.1B

| | | | |
|---|---|---|---|
| 1 | CTCAGGCCCC | AGCCGCTTCC | TGCCTGGATT | CCACAGCTTC | GCGCCGTGTA |
| 51 | CTGTCGCCCC | ATCCCTGCGC | GCCCAGCCTG | CCAAGCAGCG | TGCCCCGGTT |
| 101 | GCAGGCGTCA | TGCAGCGGGC | GCGACCCACG | CTCTGGGCCG | CTGCGCTGAC |
| 151 | TCTGCTGGTG | CTGCTCCGCG | GGCCCGCCGT | GGGCGCGGGCT | GGCGCGAGCT |
| 201 | CGGGGGGCTT | GGGTCCCGTG | GTGCGCTGCG | AGCCGTGCGA | CGCGCGTGCA |
| 251 | CTGGCCCAGT | GCGCGCCTCC | GCCCGCCGTG | TGCGCGGAGC | TGGTGCGCGA |
| 301 | GCCGGGCTGC | GGCTGCTGCC | TGACGTGCGC | ACTGAGCGAG | GGCCAGCCGT |
| 351 | GCGGCATCTA | CACCGAGCGC | TGTGGCTCCG | GCCTTCGCTG | CCAGCCGTCG |
| 401 | CCCGACGAGG | CGCGACCGCT | GCAGGCGCTG | CTGGACGGCC | GCGGGCTCTG |
| 451 | CGTCAACGCT | AGTGCCGGTCA | GCCGCCTGCG | CGCCTACCTG | CTGCCAGCGC |
| 501 | CGCCAGCTCC | AGGAAATGCT | AGTGAGTCGG | AGGAAGACCG | CAGCGCCGGC |
| 551 | AGTGTGGAGA | GCCCGTCCGT | CTCCAGCACG | CACCGGGTGT | CTGATCCCAA |
| 601 | GTTCCACCCC | CTCCATTCAA | AGATAATCAT | CATCAAGAAA | GGGCATGCTA |
| 651 | AAGACAGCCA | GCGCTACAAA | GTTGACTACG | AGTCTCAGAG | CACAGATACC |
| 701 | CAGAACTTCT | CCTCCGAGTC | CAAGCGGGAG | ACAGAATATG | GTCCCTGCCG |

FIG.2A

```
 751  TAGAGAAATG  GAAGACACAC  TGAATCACCT  GAAGTTCCTC  AATGTGCTGA
 801  GTCCCAGGGG  TGTACACATT  CCCAACTGTG  ACAAGAAGGG  ATTTTATAAG
 851  AAAAAGCAGT  GTCGCCCTTC  CAAAGGCAGG  AAGCGGGGCT  TCTGCTGGTG
 901  TGTGGATAAG  TATGGGCAGC  CTCTCCCAGG  CTACACCACC  AAGGGGAAGG
 951  AGGACGTGCA  CTGCTACAGC  ATGCAGAGCA  AGTAGACGCC  TGCCGCAAGT
1001  TAATGTGGAG  CTCAAATATG  CCTTATTTTG  CACAAAAGAC  TGCCAAGGAC
1051  ATGACCAGCA  GCTGGCTACA  GCCTCGATTT  ATATTTCTGT  TTGTGGTGAA
1101  CTGATTTTTT  TTAAACCAAA  GTTTAGAAAG  AGGTTTTTGA  AATGCCTATG
1151  GTTTCTTTGA  ATGGTAAACT  TGAATTTTTC  TTCACTTTCC  AGTAGTCAGC
1201  AAAGAGCAGT  TTGAATTTTC  TTGTCGCTTC  CTATCAAAAT  ATTCAGAGAC
1251  TCGAGCACAG  CACCCAGACT  TCATGCGCCC  GTGGAATGCT  CACCACATGT
1301  TGGTCGAAGC  GGCCGACCAC  CCCCACTCC   ACTTAGGCGG  CTGTGTTGCC
1351  TATGTAGAGA  ACACGCTTCA  CCGTACAGTG  CGCACAGGCT
1401  TTATCGAGAA  TAGGAAAACC  TTTAAACCCC  GGTCATCCGG  ACATCCCAAC
1451  GCATGCTCCT  GGAGCTCACA  GCCTTCTGTG  GTGTCATTTC  TGAAACAAGG
```

FIG. 2B

```
1501  GCGTGGATCC CTCAACCAAG AAGAATGTTT ATGTCTTCAA GTGACCTGTA
1551  CTGCTTGGGG ACTATTGGAG AAAATAAGGT GGAGTCCTAC TTGTTTAAAA
1601  AATATGTATC TAAGAATGTT CTAGGCACT  CTGGGAACCT ATAAAGGCAG
1651  GTATTTCGGG CCCTCCTCTT CAGGAATCTT CCTGAAGACA TGGCCCAGTC
1701  GAAGGCCCAG GATGGCTTTT GCTGCGGCCC CGTGGGGCCC GAGGGACAGA
1751  GAGACGGGAG AGTCAGCCTC CACATTCAGA GGCATCACAA GTAATGGCAC
1801  AATTCTTCGG ATGACTGCAG AAAATAGTGT TTTGTAGTTC AACAACTCAA
1851  GACGAAGCTT ATTTCTGAGG ATAAGCTCTT TAAAGGCAAA GCTTTATTTT
1901  CATCTCTCAT CTTTTGTCCT CCTTAGCACA ATGTAAAAAA GAATAGTAAT
1951  ATCAGAAACAG GAAGGAGGAA TGGCTTGCTG GGGAGCCCAT CCAGGACACT
2001  GGGAGCACAT AGAGATTCAC CCATGTTTGT TGAACTTAGA GTCATTCTCA
2051  TGCTTTTCTT TATAATTCAC ACATATATGC AGAGAAGATA TGTTCTTGTT
2101  AACATTGTAT ACAACATAGC CCCAAATATA GTAAGATCTA TACTAGATAA
2151  TCCTAGATGA AATGTTAGAG ATGCTATATG ATACAACTGT GGCCATGACT
2201  GAGGAAAGGA GCTCACGCCC AGAGACTGGG CTGCTCTCCC GGAGGCCAAA
```

FIG. 2C

```
2251  CCCAAGAAGG TCTGGCAAAG TCAGGCTCAG GGAGACTCTG CCCTGCTGCA
2301  GACCTCGGTG TGGACACACG CTGCATAGAG CTCTCCTTGA AAACAGAGGG
2351  GTCTCAAGAC ATTCTGCCTA CCTATTAGCT TTTCTTTATT TTTTTAACTT
2401  TTTGGGGGA AAAGTATTTT TGAGAAGTTT GTCTTGCAAT GTATTTATAA
2451  ATAGTAAATA AAGTTTTTAC CATT
```

FIG. 2D

```
1    TTTTTTTTT  TTTTGAGAAA  GGGAATTTCA  TCCCAAATAA  AAGGAATGAA
51   GTCTGGCTCC  GGAGGAGGGT  CCCCGACCTC  GCTGTGGGGG  CTCCTGTTTC
101  TCTCCGCCGC  GCTCTCGCTC  TGGCCGACGA  GTGGAGAAAT  CTGCGGGCCA
151  GGCATCGACA  TCCGCAACGA  CTATCAGCAG  CTGAAGCGCC  TGGAGAACTG
201  CACGGTGATC  GAGGGCTACC  TCCACATCCT  GCTCATCTCC  AAGGCCGAGG
251  ACTACCGCAG  CTACCGCTTC  CCCAAGCTCA  CGGTCATTAC  CGAGTACTTG
301  CTGCTGTTCC  GAGTGGCTGG  CCTCGAGAGC  CTCGGAGACC  TCTTCCCCAA
351  CCTCACGGTC  ATCCGCGGCT  GGAAACTCTT  CTACAACTAC  GCCCTGGTCA
401  TCTTCGAGAT  GACCAATCTC  AAGGATATTG  GGCTTTACAA  CCTGAGGAAC
451  ATTACTCGGG  GGGCCATCAG  GATTGAGAAA  AATGCTGACC  TCTGTTACCT
501  CTCCACTGTG  GACTGGTCCC  TGATCCTGGA  TGCGGTGTCC  AATAACTACA
551  TTGTGGGGAA  TAAGCCCCCA  AAGGAATGTG  GGGACCTGTG  TCCAGGGACC
601  ATGGAGGAGA  AGCCGATGTG  TGAGAAGACC  ACCATCAACA  ATGAGTACAA
651  CTACCGCTGC  TGGACCACAA  ACCGCTGCCA  GAAAATGTGC  CCAAGCACGT
701  GTGGGAAGCG  GGCGTGCACC  GAGAACAATG  AGTGCTGCCA  CCCCGAGTGC
```

FIG. 3A

```
 751  CTGGGCAGCT GCAGCGCGCC TGACAACGAC ACGGCCTGTG TAGCTTGCCG
 801  CCACTACTAC TATGCCGGTG TCTGTGTGCC TGCCTGCCCG CCCAACACCT
 851  ACAGGTTTGA GGGCTGGCGC TGTGTGGACC GTGACTTCTG CGCCAACATC
 901  CTCAGCGCCG AGAGCAGCGA CTCCGAGGGG TTTGTGATCC ACGACGGCGA
 951  GTGCATGCAG GAGTGCCCCT CGGGCTTCAT CCGCAACGGC AGCCAGAGCA
1001  TGTACTGCAT CCCTTGTGAA GGTCCTTGCC CGAAGGTCTG TGAGGAAGAA
1051  AAGAAAACAA AGACCATTGA TTCTGTTACT TCTGCTCAGA TGCTCCAAGG
1101  ATGCACCATC TTCAAGGGCA ATTGCTCAT TAACATCCGA CGGGGAATA
1151  ACATTGCTTC AGAGCTGGAG AACTTCATGG GGCTCATCGA GGTGGTGACG
1201  GGCTACGTGA AGATCCGCCA TTCTCATGCC TTGGTCTCCT TGTCCTTCCT
1251  AAAAAACCTT CGCCTCATCC TAGGAGAGGA GCAGCTAGAA GGGAATTACT
1301  CCTTCTACGT CCTCGACAAC CAGAACTTGC AGCAACTGTG GGACTGGGAC
1351  CACCGCAACC TGACCATCAA AGCAGGGAAA ATGTACTTTG CTTTCAATCC
1401  CAAATTATGT GTTCCGAAA TTTACCGCAT GGAGGAAGTG ACGGGACTA
1451  AAGGGCGCCA AAGCAAAGGG GACATAAACA CCAGGAACAA CGGGGAGAGA
```

FIG. 3B

```
1501  GCCTCCTGTG  AAAGTGACGT  CCTGCATTTC  ACCTCCACCA  CCACGTCGAA
1551  GAATCGCATC  ATCATAAACCT GGCACCGGTA  CCGGCCCCCT  GACTACAGGG
1601  ATCTCATCAG  CTTCACCGTT  TACTACAAGG  AAGCACCCTT  TAAGAATGTC
1651  ACAGAGTATG  ATGGGCAGGA  TGCCTGCGGC  TCCAACAGCT  GGAACATGGT
1701  GGACGTGGAC  CTCCCGCCCA  ACAAGGACGT  GGAGCCCGGC  ATCTTACTAC
1751  ATGGGCTGAA  GCCCTGGACT  CAGTACGCCG  TTTACGTCAA  GGCTGTGACC
1801  CTCACCATGG  TGGAGAACGA  CCATATCCGT  GGGGCCAAGA  GTGAGATCTT
1851  GTACATTCGC  ACCAATGCTT  CAGTTCCTTC  CATTCCCTTG  GACGTTCTTT
1901  CAGCATCGAA  CTCCTCTTCT  CAGTTAATCG  TGAAGTGGAA  CCCTCCCTCT
1951  CTGCCCAACG  GCAACCTGAG  TTACTACATT  GTGCGCTGGC  AGCGGGCAGCC
2001  TCAGGACGGC  TACCTTTACC  GGCACAATTA  CTGCTCCAAA  GACAAAATCC
2051  CCATCAGGAA  GTATGCCGAC  GGCACCATCG  ACATTGAGGA  GGTCACAGAG
2101  AACCCCAAGA  CTGAGGTGTG  TGGTGGGGAG  AAAGGGCCTT  GCTGCGCCTG
2151  CCCCAAAACT  GAAGCCGAGA  AGCAGGCCGA  GAAGGAGGAG  GCTGAATACC
2201  GCAAAGTCTT  TGAGAATTTC  CTGCACAACT  CCATCTTCGT  GCCCAGACCT
```

FIG.3C

```
2251  GAAAGGAAGC  GGAGAGATGT  CATGCAAGTG  GCCAACACCA  CCATGTCCAG
2301  CCGAAGCAGG  AACACCACGG  CCGCAGACAC  CTACAACATC  ACCGACCCGG
2351  AAGAGCTGGA  GACAGAGTAC  CCTTTCTTTG  AGAGCAGAGT  GGATAACAAG
2401  GAGAGAACTG  TCATTTCTAA  CCTTCGGCCT  TTCACATTGT  ACCGCATCGA
2451  TATCCACAGC  TGCAACCACG  AGGCTGAGAA  GCTGGGCTGC  AGCGCCTCCA
2501  ACTTCGTCTT  TGCAAGGACT  ATGCCCGCAG  AAGGAGCAGA  TGACATTCCT
2551  GGGCCAGTGA  CCTGGGAGCC  AAGGCCTGAA  AACTCCATCT  TTTTAAAGTG
2601  GCCGGAACCT  GAGAATCCCA  ATGGATTGAT  TCTAATGTAT  GAAATAAAAT
2651  ACGGATCACA  AGTTGAGGAT  CAGCGAGAAT  GTGTGTCCAG  ACAGGAATAC
2701  AGGAAGTATG  GAGGGGCCAA  GCTAAACCGG  CTAAAACCCGG  GGAACTACAC
2751  AGCCCGGATT  CAGGCCACAT  CTCTCTCTGG  GAATGGGTCG  TGGACAGATC
2801  CTGTGTTCTT  CTATGTCCAG  GCCAAAACAG  GATATGAAAA  CTTCATCCAT
2851  CTGATCATCG  CTCTGCCCGT  CGCTGTCCTG  TTGATCGTGG  GAGGGTTGGT
2901  GATTATGCTG  TACGTCTTCC  ATAGAAAGAG  AAATAACAGC  AGGCTGGGGA
2951  ATGGAGTGCT  GTATGCCTCT  GTGAACCCGG  AGTACTTCAG  CGCTGCTGAT
```

FIG.3D

```
3001  GTGTACGTTC  CTGATGAGTG  GGAGGTGGCT  CGGGAGAAGA  TCACCATGAG
3051  CCGGGAACTT  GGGCAGGGGT  CGTTTGGGAT  GGTCTATGAA  GGAGTTGCCA
3101  AGGGTGTGGT  GAAAGATGAA  CCTGAAACCA  GAGTGGCCAT  TAAAACAGTG
3151  AACGAGGCCG  CAAGCATGCG  TGAGAGGATT  GAGTTTCTCA  ACGAAGCTTC
3201  TGTGATGAAG  GAGTTCAATT  GTCACCATGT  GGTGCGATTG  CTGGGTGTGG
3251  TGTCCCAAGG  CCAGCCAACA  CTGGTCATCA  TGGAACTGAT  GACACGGGGC
3301  GATCTCAAAA  GTTATCTCCG  GTCTCTGAGG  CCAGAAAATGG  AGAATAATCC
3351  AGTCCTAGCA  CCTCCAAGCC  TGAGCAAGAT  GATTCAGATG  GCCGGAGAGA
3401  TTGCAGACGG  CATGGCATAC  CTCAACGCCA  ATAAGTTCGT  CCACAGAGAC
3451  CTTGCTGCCC  GGAATTGCAT  GGTAGCCGAA  GATTTCACAG  TCAAAATCGG
3501  AGATTTTGGT  ATGACGCGAG  ATATCTATGA  GACAGACTAT  TACCGGAAAG
3551  GAGGCAAAGG  GCTGCTGCCC  GTGCGCTGGA  TGTCTCCTGA  GTCCCTCAAG
3601  GATGGAGTCT  TCACCACTTA  CTCGGACGTC  TGGTCCTTCG  GGGTCGTCCT
3651  CTGGGAGATC  GCCACACTGG  CCGAGCAGCC  CTACCAGGGC  TTGTCCAACG
3701  AGCAAGTCCT  TCGCTTCGTC  ATGGAGGGCG  GCCTTCTGGA  CAAGCCAGAC
```

FIG. 3E

```
3751  AACTGTCCTG ACATGCTGTT TGAACTGATG CGCATGTGCT GGCAGTATAA
3801  CCCCAAGATG AGGCCTTCCT TCCTGGAGAT CATCAGCAGC ATCAAAGAGG
3851  AGATGGAGCC TGGCTTCCGG GAGGTCTCCT TCTACTACAG CGAGGAGAAC
3901  AAGCTGCCCG AGCCGGAGGA GCTGGACCTG GAGCCAGAGA ACATGGAGAG
3951  CGTCCCCCTG GACCCCCTCG CCTCCCTGTC CTCCCTGCCA CTGCCCGACA
4001  GACACTCAGG ACACAAGGCC GAGAACGGCC CCGGCCCTGG GGTGCTGGTC
4051  CTCCGGCGCCA GCTTCGACGA GAGACAGCCT TACGCCCACA TGAACGGGGG
4101  CCGCAAGAAC GAGCGGGCCT TGCCGCTGCC CCAGTCTTCG ACCTGCTGAT
4151  CCTTGGATCC TGAATCTGTG CAAACAGTAA CGTGTGCGCA CGGCCAGCGG
4201  GGTGGGGGGG GAGAGAGAGT CATTCACAAG CCTCCTGTAC
4251  CTCAGTGGAT CTTCAGTTCT GCCCTTGCTG CCCGCGGGAG ACAGCTTCTC
4301  TGCAGTAAAA CACATTTGGG ATGTTCCTTT TTTCAATATG CAAGCAGCTT
4351  TTTATTCCCT GCCCAAACCC TTAACTGACA TGGCCTTTA AGAACCTTAA
4401  TGACAACACT TAATAGCAAC AGAGCACTTG AGAACCAGTC TCCTCACTCT
4451  GTCCCTGTCC TTCCCTGTTC TCCCTTTCTC TCTCCTCTCT GCTTCATAAC
```

FIG.3F

```
4501  GGAAAAATAA TTGCCACAAG TCCAGCTGGG AAGCCCTTTT TATCAGTTTG
4551  AGGAAGTGGC TGTCCCTGTG GCCCCATCCA ACCACTGTAC ACACCCGCCT
4601  GACACCGTGG GTCATTACAA AAAAACACGT GGAGATGGAA ATTTTTACCT
4651  TTATCTTTCA CCTTTCTAGG GACATGAAAT TTACAAAGGG CCATCGTTCA
4701  TCCAAGGCTG TTACCATTTT AACGCTGCCT AATTTTGCCA AAATCCTGAA
4751  CTTTCTCCCT CATCGGCCCG GCGCTGATTC CTCGTGTCCG GAGGCATGGG
4801  TGAGCATGGC AGCTGGTTGC TCCATTTGAG AGACACGCTG GCGACACACT
4851  CCGTCCATCC GACTGCCCCT GCTGTGCTGC TCAAGGCCAC AGGCACACAG
4901  GTCTCATTGC TTCTGACTAG ATTATTATTT GGGGGAACTG GACACAATAG
4951  GTCTTTCTCT CAGTGAAGGT GGGGAGAAGC TGAACCGGC
```

FIG. 3G

US 6,284,741 B1

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 1433 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: Coding Sequence
       (B) LOCATION: 118...1101
       (D) OTHER INFORMATION:
       (A) NAME/KEY: Coding Sequence
       (B) LOCATION: 118...234
       (D) OTHER INFORMATION:
       (A) NAME/KEY: Coding Sequence
       (B) LOCATION: 235...1101
       (D) OTHER INFORMATION:

(x) PUBLICATION INFORMATION:
       (A) AUTHORS: Binkert, C., et al.
       (B) TITLE: Cloning, sequence analysis and expression...
       (C) JOURNAL: EMBO J.
       (D) VOLUME: 8
       (E) ISSUE: 1989
       (F) PAGES: 2497-2502
       (G) DATE:

(xi) SEQUENCE DESCRIPTION: SEQ ID NO:1:

```
ATTCGGGGCG AGGGAGGAGG AAGAAGCGGA GGAGGCGGCT CCCGCTCGCA GGGCCGTGCA     60

CCTGCCCGCC CGCCCGCTCG CTCGCTCGCC CGCCGCGCCG CGCTGCCGAC CGCCAGC ATG   120
                                                                Met
                                                                  1

CTG CCG AGA GTG GGC TGC CCC GCG CTG CCG CTG CCG CCG CCG CCG CTG     168
Leu Pro Arg Val Gly Cys Pro Ala Leu Pro Leu Pro Pro Pro Pro Leu
              5                  10                  15

CTG CCG CTG CTG CCG CTG CTG CTG CTG CTA CTG GGC GCG AGT GGC GGC     216
Leu Pro Leu Leu Pro Leu Leu Leu Leu Leu Gly Ala Ser Gly Gly
         20                  25                  30

GGC GGC GGG GCG CGC GCG GAG GTG CTG TTC CGC TGC CCG CCC TGC ACA     264
Gly Gly Gly Ala Arg Ala Glu Val Leu Phe Arg Cys Pro Pro Cys Thr
     35                  40                  45

CCC GAG CGC CTG GCC GCC TGC GGG CCC CCG CCG GTT GCG CCG CCC GCC     312
Pro Glu Arg Leu Ala Ala Cys Gly Pro Pro Pro Val Ala Pro Pro Ala
 50                  55                  60                  65

GCG GTG GCC GCA GTG GCC GGA GGC GCC CGC ATG CCA TGC GCG GAG CTC     360
Ala Val Ala Ala Val Ala Gly Gly Ala Arg Met Pro Cys Ala Glu Leu
                 70                  75                  80

GTC CGG GAG CCG GGC TGC GGC TGC TGC TCG GTG TGC GCC CGG CTG GAG     408
Val Arg Glu Pro Gly Cys Gly Cys Cys Ser Val Cys Ala Arg Leu Glu
                 85                  90                  95

GGC GAG GCG TGC GGC GTC TAC ACC CCG CGC TGC GGC CAG GGG CTG CGC     456
Gly Glu Ala Cys Gly Val Tyr Thr Pro Arg Cys Gly Gln Gly Leu Arg
            100                 105                 110

TGC TAT CCC CAC CCG GGC TCC GAG CTG CCC CTG CAG GCG CTG GTC ATG     504
Cys Tyr Pro His Pro Gly Ser Glu Leu Pro Leu Gln Ala Leu Val Met
        115                 120                 125

GGC GAG GGC ACT TGT GAG AAG CGC CGG GAC GCC GAG TAT GGC GCC AGC     552
```

```
Gly Glu Gly Thr Cys Glu Lys Arg Arg Asp Ala Glu Tyr Gly Ala Ser
130                 135                 140                 145

CCG GAG CAG GTT GCA GAC AAT GGC GAT GAC CAC TCA GAA GGA GGC CTG      600
Pro Glu Gln Val Ala Asp Asn Gly Asp Asp His Ser Glu Gly Gly Leu
            150                 155                 160

GTG GAG AAC CAC GTG GAC AGC ACC ATG AAC ATG TTG GGC GGG GGA GGC      648
Val Glu Asn His Val Asp Ser Thr Met Asn Met Leu Gly Gly Gly Gly
                165                 170                 175

AGT GCT GGC CGG AAG CCC CTC AAG TCG GGT ATG AAG GAG CTG GCC GTG      696
Ser Ala Gly Arg Lys Pro Leu Lys Ser Gly Met Lys Glu Leu Ala Val
            180                 185                 190

TTC CGG GAG AAG GTC ACT GAG CAG CAC CGG CAG ATG GGC AAG GGT GGC      744
Phe Arg Glu Lys Val Thr Glu Gln His Arg Gln Met Gly Lys Gly Gly
195                 200                 205

AAG CAT CAC CTT GGC CTG GAG GAG CCC AAG AAG CTG CGA CCA CCC CCT      792
Lys His His Leu Gly Leu Glu Glu Pro Lys Lys Leu Arg Pro Pro Pro
210                 215                 220                 225

GCC AGG ACT CCC TGC CAA CAG GAA CTG GAC CAG GTC CTG GAG CGG ATC      840
Ala Arg Thr Pro Cys Gln Gln Glu Leu Asp Gln Val Leu Glu Arg Ile
                230                 235                 240

TCC ACC ATG CGC CTT CCG GAT GAG CGG GGC CCT CTG GAG CAC CTC TAC      888
Ser Thr Met Arg Leu Pro Asp Glu Arg Gly Pro Leu Glu His Leu Tyr
                245                 250                 255

TCC CTG CAC ATC CCC AAC TGT GAC AAG CAT GGC CTG TAC AAC CTC AAA      936
Ser Leu His Ile Pro Asn Cys Asp Lys His Gly Leu Tyr Asn Leu Lys
            260                 265                 270

CAG TGC AAG ATG TCT CTG AAC GGG CAG CGT GGG GAG TGC TGG TGT GTG      984
Gln Cys Lys Met Ser Leu Asn Gly Gln Arg Gly Glu Cys Trp Cys Val
275                 280                 285

AAC CCC AAC ACC GGG AAG CTG ATC CAG GGA GCC CCC ACC ATC CGG GGG     1032
Asn Pro Asn Thr Gly Lys Leu Ile Gln Gly Ala Pro Thr Ile Arg Gly
290                 295                 300                 305

GAC CCC GAG TGT CAT CTC TTC TAC AAT GAG CAG CAG GAG GCT TGC GGG     1080
Asp Pro Glu Cys His Leu Phe Tyr Asn Glu Gln Gln Glu Ala Cys Gly
                310                 315                 320

GTG CAC ACC CAG CGG ATG CAG TAGACCGCAG CCAGCCGGTG CCTGGCGCCC CTGC   1135
Val His Thr Gln Arg Met Gln
                325

CCCCCGCCCC TCTCCAAACA CCGGCAGAAA ACGGAGAGTG CTTGGGTGGT GGGTGCTGGA   1195

GGATTTTCCA GTTCTGACAC ACGTATTTAT ATTTGGAAAG AGACCAGCAC CGAGCTCGGC   1255

ACCTCCCCGG CCTCTCTCTT CCCAGCTGCA GATGCCACAC CTGCTCCTTC TTGCTTTCCC   1315

CGGGGGAGGA AGGGGGTTGT GGTCGGGGAG CTGGGGTACA GGTTTGGGGA GGGGGAAGAG   1375

AAATTTTTAT TTTTGAACCC CTGTGTCCCT TTTGCATAAG ATTAAAGGAA GGAAAAGT    1433

(2) INFORMATION FOR SEQ ID NO:2:

(i) SEQUENCE CHARACTERISTICS:
        (A) LENGTH: 2474 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 110...982
        (D) OTHER INFORMATION:

(x) PUBLICATION INFORMATION:
        (A) AUTHORS: Wood, W.I., et al.
```

(B) TITLE: Cloning and expression of the growth...
(C) JOURNAL: Mol. Endocrinol.
(D) VOLUME: 2
(E) ISSUE: 1988
(F) PAGES: 1176-1185
(G) DATE:

(xi) SEQUENCE DESCRIPTION: SEQ ID NO:2:

```
CTCAGCGCCC AGCCGCTTCC TGCCTGGATT CCACAGCTTC GCGCCGTGTA CTGTCGCCCC        60

ATCCCTGCGC GCCCAGCCTG CCAAGCAGCG TGCCCCGGTT GCAGGCGTC ATG CAG CGG       118
                                                     Met Gln Arg
                                                       1

GCG CGA CCC ACG CTC TGG GCC GCT GCG CTG ACT CTG CTG GTG CTG CTC        166
Ala Arg Pro Thr Leu Trp Ala Ala Ala Leu Thr Leu Leu Val Leu Leu
      5              10                  15

CGC GGG CCG CCG GTG GCG CGG GCT GGC GCG AGC TCG GGG GGC TTG GGT        214
Arg Gly Pro Pro Val Ala Arg Ala Gly Ala Ser Ser Gly Gly Leu Gly
 20              25                  30                  35

CCC GTG GTG CGC TGC GAG CCG TGC GAC GCG CGT GCA CTG GCC CAG TGC        262
Pro Val Val Arg Cys Glu Pro Cys Asp Ala Arg Ala Leu Ala Gln Cys
              40                  45                  50

GCG CCT CCG CCC GCC GTG TGC GCG GAG CTG GTG CGC GAG CCG GGC TGC        310
Ala Pro Pro Pro Ala Val Cys Ala Glu Leu Val Arg Glu Pro Gly Cys
          55                  60                  65

GGC TGC TGC CTG ACG TGC GCA CTG AGC GAG GGC CAG CCG TGC GGC ATC        358
Gly Cys Cys Leu Thr Cys Ala Leu Ser Glu Gly Gln Pro Cys Gly Ile
      70                  75                  80

TAC ACC GAG CGC TGT GGC TCC GGC CTT CGC TGC CAG CCG TCG CCC GAC        406
Tyr Thr Glu Arg Cys Gly Ser Gly Leu Arg Cys Gln Pro Ser Pro Asp
 85                  90                  95

GAG GCG CGA CCG CTG CAG GCG CTG CTG GAC GGC CGC GGG CTC TGC GTC        454
Glu Ala Arg Pro Leu Gln Ala Leu Leu Asp Gly Arg Gly Leu Cys Val
100              105                 110                 115

AAC GCT AGT GCC GTC AGC CGC CTG CGC GCC TAC CTG CTG CCA GCG CCG        502
Asn Ala Ser Ala Val Ser Arg Leu Arg Ala Tyr Leu Leu Pro Ala Pro
                 120                 125                 130

CCA GCT CCA GGA AAT GCT AGT GAG TCG GAG GAA GAC CGC AGC GCC GGC        550
Pro Ala Pro Gly Asn Ala Ser Glu Ser Glu Glu Asp Arg Ser Ala Gly
             135                 140                 145

AGT GTG GAG AGC CCG TCC GTC TCC AGC ACG CAC CGG GTG TCT GAT CCC        598
Ser Val Glu Ser Pro Ser Val Ser Ser Thr His Arg Val Ser Asp Pro
         150                 155                 160

AAG TTC CAC CCC CTC CAT TCA AAG ATA ATC ATC ATC AAG AAA GGG CAT        646
Lys Phe His Pro Leu His Ser Lys Ile Ile Ile Ile Lys Lys Gly His
165                 170                 175

GCT AAA GAC AGC CAG CGC TAC AAA GTT GAC TAC GAG TCT CAG AGC ACA        694
Ala Lys Asp Ser Gln Arg Tyr Lys Val Asp Tyr Glu Ser Gln Ser Thr
180                 185                 190                 195

GAT ACC CAG AAC TTC TCC TCC GAG TCC AAG CGG GAG ACA GAA TAT GGT        742
Asp Thr Gln Asn Phe Ser Ser Glu Ser Lys Arg Glu Thr Glu Tyr Gly
                 200                 205                 210

CCC TGC CGT AGA GAA ATG GAA GAC ACA CTG AAT CAC CTG AAG TTC CTC        790
Pro Cys Arg Arg Glu Met Glu Asp Thr Leu Asn His Leu Lys Phe Leu
             215                 220                 225

AAT GTG CTG AGT CCC AGG GGT GTA CAC ATT CCC AAC TGT GAC AAG AAG        838
Asn Val Leu Ser Pro Arg Gly Val His Ile Pro Asn Cys Asp Lys Lys
         230                 235                 240

GGA TTT TAT AAG AAA AAG CAG TGT CGC CCT TCC AAA GGC AGG AAG CGG        886
Gly Phe Tyr Lys Lys Lys Gln Cys Arg Pro Ser Lys Gly Arg Lys Arg
245                 250                 255
```

-continued

```
GGC TTC TGC TGG TGT GTG GAT AAG TAT GGG CAG CCT CTC CCA GGC TAC    934
Gly Phe Cys Trp Cys Val Asp Lys Tyr Gly Gln Pro Leu Pro Gly Tyr
260                 265                 270                 275

ACC ACC AAG GGG AAG GAG GAC GTG CAC TGC TAC AGC ATG CAG AGC AAG T  983
Thr Thr Lys Gly Lys Glu Asp Val His Cys Tyr Ser Met Gln Ser Lys
            280                 285                 290

AGACGCCTGC CGCAAGTTAA TGTGGAGCTC AAATATGCCT TATTTTGCAC AAAAGACTGC 1043

CAAGGACATG ACCAGCAGCT GGCTACAGCC TCGATTTATA TTTCTGTTTG TGGTGAACTG 1103

ATTTTTTTTA AACCAAAGTT TAGAAAGAGG TTTTTGAAAT GCCTATGGTT TCTTTGAATG 1163

GTAAACTTGA GCATCTTTTC ACTTTCCAGT AGTCAGCAAA GAGCAGTTTG AATTTTCTTG 1223

TCGCTTCCTA TCAAAATATT CAGAGACTCG AGCACAGCAC CCAGACTTCA TGCGCCCGTG 1283

GAATGCTCAC CACATGTTGG TCGAAGCGGC CGACCACTGA CTTTGTGACT TAGGCGGCTG 1343

TGTTGCCTAT GTAGAGAACA CGCTTCACCC CCACTCCCCG TACAGTGCGC ACAGGCTTTA 1403

TCGAGAATAG GAAAACCTTT AAACCCCGGT CATCCGGACA TCCCAACGCA TGCTCCTGGA 1463

GCTCACAGCC TTCTGTGGTG TCATTTCTGA ACAAGGGCG TGGATCCCTC AACCAAGAAG 1523

AATGTTTATG TCTTCAAGTG ACCTGTACTG CTTGGGGACT ATTGGAGAAA ATAAGGTGGA 1583

GTCCTACTTG TTTAAAAAAT ATGTATCTAA GAATGTTCTA GGGCACTCTG GGAACCTATA 1643

AAGGCAGGTA TTTCGGGCCC TCCTCTTCAG GAATCTTCCT GAAGACATGG CCCAGTCGAA 1703

GGCCCAGGAT GGCTTTTGCT GCGGCCCCGT GGGGTAGGAG GGACAGAGAG ACGGGAGAGT 1763

CAGCCTCCAC ATTCAGAGGC ATCACAAGTA ATGGCACAAT TCTTCGGATG ACTGCAGAAA 1823

ATAGTGTTTT GTAGTTCAAC AACTCAAGAC GAAGCTTATT TCTGAGGATA AGCTCTTTAA 1883

AGGCAAAGCT TTATTTTCAT CTCTCATCTT TTGTCCTCCT TAGCACAATG TAAAAAGAA  1943

TAGTAATATC AGAACAGGAA GGAGGAATGG CTTGCTGGGG AGCCCATCCA GGACACTGGG 2003

AGCACATAGA GATTCACCCA TGTTTGTTGA ACTTAGAGTC ATTCTCATGC TTTTCTTTAT 2063

AATTCACACA TATATGCAGA GAAGATATGT TCTTGTTAAC ATTGTATACA ACATAGCCCC 2123

AAATATAGTA AGATCTATAC TAGATAATCC TAGATGAAAT GTTAGAGATG CTATATGATA 2183

CAACTGTGGC CATGACTGAG GAAAGGAGCT CACGCCCAGA GACTGGGCTG CTCTCCCGGA 2243

GGCCAAACCC AAGAAGGTCT GGCAAAGTCA GGCTCAGGGA GACTCTGCCC TGCTGCAGAC 2303

CTCGGTGTGG ACACACGCTG CATAGAGCTC TCCTTGAAAA CAGAGGGGTC TCAAGACATT 2363

CTGCCTACCT ATTAGCTTTT CTTTATTTTT TTAACTTTTT GGGGGGAAAA GTATTTTGA  2423

GAAGTTTGTC TTGCAATGTA TTTATAAATA GTAAATAAAG TTTTTACCAT T          2474
```

(2) INFORMATION FOR SEQ ID NO:3:

(i) SEQUENCE CHARACTERISTICS:
        (A) LENGTH: 4989 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(x) PUBLICATION INFORMATION:
        (A) AUTHORS: Ullrich, A., et al.

(B) TITLE: Insulin-like growth factor I receptor...
(C) JOURNAL: EMBO J.
(D) VOLUME: 5
(E) ISSUE: 1986
(F) PAGES: 2503-2512
(G) DATE:

(xi) SEQUENCE DESCRIPTION: SEQ ID NO:3:

| | | | | | |
|---|---|---|---|---|---|
| TTTTTTTTTT | TTTTGAGAAA | GGGAATTTCA | TCCCAAATAA | AAGGAATGAA | GTCTGGCTCC | 60 |
| GGAGGAGGGT | CCCCGACCTC | GCTGTGGGGG | CTCCTGTTTC | TCTCCGCCGC | GCTCTCGCTC | 120 |
| TGGCCGACGA | GTGGAGAAAT | CTGCGGGCCA | GGCATCGACA | TCCGCAACGA | CTATCAGCAG | 180 |
| CTGAAGCGCC | TGGAGAACTG | CACGGTGATC | GAGGGCTACC | TCCACATCCT | GCTCATCTCC | 240 |
| AAGGCCGAGG | ACTACCGCAG | CTACCGCTTC | CCCAAGCTCA | CGGTCATTAC | CGAGTACTTG | 300 |
| CTGCTGTTCC | GAGTGGCTGG | CCTCGAGAGC | CTCGGAGACC | TCTTCCCCAA | CCTCACGGTC | 360 |
| ATCCGCGGCT | GGAAACTCTT | CTACAACTAC | GCCCTGGTCA | TCTTCGAGAT | GACCAATCTC | 420 |
| AAGGATATTG | GCTTTACAA | CCTGAGGAAC | ATTACTCGGG | GGGCCATCAG | GATTGAGAAA | 480 |
| AATGCTGACC | TCTGTTACCT | CTCCACTGTG | GACTGGTCCC | TGATCCTGGA | TGCGGTGTCC | 540 |
| AATAACTACA | TTGTGGGGAA | TAAGCCCCCA | AAGGAATGTG | GGACCTGTG | TCCAGGGACC | 600 |
| ATGGAGGAGA | AGCCGATGTG | TGAGAAGACC | ACCATCAACA | ATGAGTACAA | CTACCGCTGC | 660 |
| TGGACCACAA | ACCGCTGCCA | GAAAATGTGC | CCAAGCACGT | GTGGGAAGCG | GGCGTGCACC | 720 |
| GAGAACAATG | AGTGCTGCCA | CCCCGAGTGC | CTGGGCAGCT | GCAGCGCGCC | TGACAACGAC | 780 |
| ACGGCCTGTG | TAGCTTGCCG | CCACTACTAC | TATGCCGGTG | TCTGTGTGCC | TGCCTGCCCG | 840 |
| CCCAACACCT | ACAGGTTTGA | GGGCTGGCGC | TGTGTGGACC | GTGACTTCTG | CGCCAACATC | 900 |
| CTCAGCGCCG | AGAGCAGCGA | CTCCGAGGGG | TTTGTGATCC | ACGACGGCGA | GTGCATGCAG | 960 |
| GAGTGCCCCT | CGGGCTTCAT | CCGCAACGGC | AGCCAGAGCA | TGTACTGCAT | CCCTTGTGAA | 1020 |
| GGTCCTTGCC | CGAAGGTCTG | TGAGGAAGAA | AAGAAAACAA | AGACCATTGA | TTCTGTTACT | 1080 |
| TCTGCTCAGA | TGCTCCAAGG | ATGCACCATC | TTCAAGGGCA | ATTTGCTCAT | TAACATCCGA | 1140 |
| CGGGGGAATA | ACATTGCTTC | AGAGCTGGAG | AACTTCATGG | GGCTCATCGA | GGTGGTGACG | 1200 |
| GGCTACGTGA | AGATCCGCCA | TTCTCATGCC | TTGGTCTCCT | TGTCCTTCCT | AAAAAACCTT | 1260 |
| CGCCTCATCC | TAGGAGAGGA | GCAGCTAGAA | GGGAATTACT | CCTTCTACGT | CCTCGACAAC | 1320 |
| CAGAACTTGC | AGCAACTGTG | GGACTGGGAC | CACCGCAACC | TGACCATCAA | AGCAGGGAAA | 1380 |
| ATGTACTTTG | CTTTCAATCC | CAAATTATGT | GTTTCCGAAA | TTTACCGCAT | GGAGGAAGTG | 1440 |
| ACGGGGACTA | AAGGGCGCCA | AAGCAAAGGG | GACATAAACA | CCAGGAACAA | CGGGGAGAGA | 1500 |
| GCCTCCTGTG | AAAGTGACGT | CCTGCATTTC | ACCTCCACCA | CCACGTCGAA | GAATCGCATC | 1560 |
| ATCATAACCT | GGCACCGGTA | CCGGCCCCCT | GACTACAGGG | ATCTCATCAG | CTTCACCGTT | 1620 |
| TACTACAAGG | AAGCACCCTT | TAAGAATGTC | ACAGAGTATG | ATGGGCAGGA | TGCCTGCGGC | 1680 |
| TCCAACAGCT | GGAACATGGT | GGACGTGGAC | CTCCCGCCCA | ACAAGGACGT | GGAGCCCGGC | 1740 |
| ATCTTACTAC | ATGGGCTGAA | GCCCTGGACT | CAGTACGCCG | TTTACGTCAA | GGCTGTGACC | 1800 |
| CTCACCATGG | TGGAGAACGA | CCATATCCGT | GGGGCCAAGA | GTGAGATCTT | GTACATTCGC | 1860 |
| ACCAATGCTT | CAGTTCCTTC | CATTCCCTTG | GACGTTCTTT | CAGCATCGAA | CTCCTCTTCT | 1920 |
| CAGTTAATCG | TGAAGTGGAA | CCCTCCCTCT | CTGCCCAACG | GCAACCTGAG | TTACTACATT | 1980 |
| GTGCGCTGGC | AGCGGCAGCC | TCAGGACGGC | TACCTTTACC | GGCACAATTA | CTGCTCCAAA | 2040 |
| GACAAAATCC | CCATCAGGAA | GTATGCCGAC | GGCACCATCG | ACATTGAGGA | GGTCACAGAG | 2100 |

```
AACCCCAAGA CTGAGGTGTG TGGTGGGGAG AAAGGGCCTT GCTGCGCCTG CCCCAAAACT   2160

GAAGCCGAGA AGCAGGCCGA GAAGGAGGAG GCTGAATACC GCAAAGTCTT TGAGAATTTC   2220

CTGCACAACT CCATCTTCGT GCCCAGACCT GAAAGGAAGC GGAGAGATGT CATGCAAGTG   2280

GCCAACACCA CCATGTCCAG CCGAAGCAGG AACACCACGG CCGCAGACAC CTACAACATC   2340

ACCGACCCGG AAGAGCTGGA GACAGAGTAC CCTTTCTTTG AGAGCAGAGT GGATAACAAG   2400

GAGAGAACTG TCATTTCTAA CCTTCGGCCT TTCACATTGT ACCGCATCGA TATCCACAGC   2460

TGCAACCACG AGGCTGAGAA GCTGGGCTGC AGCGCCTCCA ACTTCGTCTT GCAAGGACT    2520

ATGCCCGCAG AAGGAGCAGA TGACATTCCT GGGCCAGTGA CCTGGGAGCC AAGGCCTGAA   2580

AACTCCATCT TTTTAAAGTG GCCGGAACCT GAGAATCCCA ATGGATTGAT TCTAATGTAT   2640

GAAATAAAAT ACGGATCACA AGTTGAGGAT CAGCGAGAAT GTGTGTCCAG ACAGGAATAC   2700

AGGAAGTATG GAGGGGCCAA GCTAAACCGG CTAAACCGGG GAACTACAC AGCCCGGATT    2760

CAGGCCACAT CTCTCTCTGG GAATGGGTCG TGGACAGATC CTGTGTTCTT CTATGTCCAG   2820

GCCAAAACAG GATATGAAAA CTTCATCCAT CTGATCATCG CTCTGCCCGT CGCTGTCCTG   2880

TTGATCGTGG GAGGGTTGGT GATTATGCTG TACGTCTTCC ATAGAAAGAG AAATAACAGC   2940

AGGCTGGGGA ATGGAGTGCT GTATGCCTCT GTGAACCCGG AGTACTTCAG CGCTGCTGAT   3000

GTGTACGTTC CTGATGAGTG GGAGGTGGCT CGGGAGAAGA TCACCATGAG CCGGGAACTT   3060

GGGCAGGGGT CGTTTGGGAT GGTCTATGAA GGAGTTGCCA AGGGTGTGGT GAAAGATGAA   3120

CCTGAAACCA GAGTGGCCAT TAAAACAGTG AACGAGGCCG CAAGCATGCG TGAGAGGATT   3180

GAGTTTCTCA ACGAAGCTTC TGTGATGAAG GAGTTCAATT GTCACCATGT GGTGCGATTG   3240

CTGGGTGTGG TGTCCCAAGG CCAGCCAACA CTGGTCATCA TGGAACTGAT GACACGGGGC   3300

GATCTCAAAA GTTATCTCCG GTCTCTGAGG CCAGAAATGG AGAATAATCC AGTCCTAGCA   3360

CCTCCAAGCC TGAGCAAGAT GATTCAGATG GCCGGAGAGA TTGCAGACGG CATGGCATAC   3420

CTCAACGCCA ATAAGTTCGT CCACAGAGAC CTTGCTGCCC GGAATTGCAT GGTAGCCGAA   3480

GATTTCACAG TCAAAATCGG AGATTTTGGT ATGACGCGAG ATATCTATGA GACAGACTAT   3540

TACCGGAAAG GAGGCAAAGG GCTGCTGCCC GTGCGCTGGA TGTCTCCTGA GTCCCTCAAG   3600

GATGGAGTCT TCACCACTTA CTCGGACGTC TGGTCCTTCG GGGTCGTCCT CTGGGAGATC   3660

GCCACACTGG CCGAGCAGCC CTACCAGGGC TTGTCCAACG AGCAAGTCCT TCGCTTCGTC   3720

ATGGAGGGCG GCCTTCTGGA CAAGCCAGAC AACTGTCCTG ACATGCTGTT TGAACTGATG   3780

CGCATGTGCT GGCAGTATAA CCCCAAGATG AGGCCTTCCT TCCTGGAGAT CATCAGCAGC   3840

ATCAAAGAGG AGATGGAGCC TGGCTTCCGG GAGGTCTCCT TCTACTACAG CGAGGAGAAC   3900

AAGCTGCCCG AGCCGGAGGA GCTGGACCTG GAGCCAGAGA ACATGGAGAG CGTCCCCCTG   3960

GACCCCTCGG CCTCCTCGTC CTCCCTGCCA CTGCCCGACA GACACTCAGG ACACAAGGCC   4020

GAGAACGGCC CCGGCCCTGG GGTGCTGGTC CTCCGCGCCA GCTTCGACGA GAGACAGCCT   4080

TACGCCCACA TGAACGGGGG CCGCAAGAAC GAGCGGGCCT TGCCGCTGCC CCAGTCTTCG   4140

ACCTGCTGAT CCTTGGATCC TGAATCTGTG CAAACAGTAA CGTGTGCGCA CGCGCAGCGG   4200

GGTGGGGGGG GAGAGAGAGT TTTAACAATC CATTCACAAG CCTCCTGTAC CTCAGTGGAT   4260

CTTCAGTTCT GCCCTTGCTG CCCGCGGGAG ACAGCTTCTC TGCAGTAAAA CACATTTGGG   4320

ATGTTCCTTT TTTCAATATG CAAGCAGCTT TTTATTCCCT GCCCAAACCC TTAACTGACA   4380

TGGGCCTTTA AGAACCTTAA TGACAACACT TAATAGCAAC AGAGCACTTG AGAACCAGTC   4440

TCCTCACTCT GTCCCTGTCC TTCCCTGTTC TCCCTTTCTC TCTCCTCTCT GCTTCATAAC   4500
```

-continued

```
GGAAAAATAA TTGCCACAAG TCCAGCTGGG AAGCCCTTTT TATCAGTTTG AGGAAGTGGC    4560

TGTCCCTGTG GCCCCATCCA ACCACTGTAC ACACCCGCCT GACACCGTGG GTCATTACAA    4620

AAAAACACGT GGAGATGGAA ATTTTTACCT TTATCTTTCA CCTTTCTAGG GACATGAAAT    4680

TTACAAAGGG CCATCGTTCA TCCAAGGCTG TTACCATTTT AACGCTGCCT AATTTTGCCA    4740

AAATCCTGAA CTTTCTCCCT CATCGGCCCG GCGCTGATTC CTCGTGTCCG GAGGCATGGG    4800

TGAGCATGGC AGCTGGTTGC TCCATTTGAG AGACACGCTG GCGACACACT CCGTCCATCC    4860

GACTGCCCCT GCTGTGCTGC TCAAGGCCAC AGGCACACAG GTCTCATTGC TTCTGACTAG    4920

ATTATTATTT GGGGGAACTG GACACAATAG GTCTTTCTCT CAGTGAAGGT GGGGAGAAGC    4980

TGAACCGGC                                                           4989
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

```
GCGCCCGCTG CATGACGCCT GCAAC                                           25
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

```
CGGGCGGCTC ACCTGGAGCT GGCG                                            24
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO

```
        (v) FRAGMENT TYPE:

(vi) ORIGINAL SOURCE:

(xi) SEQUENCE DESCRIPTION: SEQ ID NO:6:

AGGCGGCTGA CGGCACTA                                               18

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CAGGCGTCAT GCAGCGGGC                                              19

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CGGAGATGCC GCATGCCAGC GCAGG                                       25

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GACAGCGTCG GAGCGATC                                               18
```

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

ATCTCTCCGC TTCCTTTC                                    18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GAAAGGAAGC GGAGAGAT                                    18

METHOD FOR THE PROPHYLAXIS AND/OR TREATMENT OF PROLIFERATIVE AND/OR INFLAMMATORY SKIN DISORDERS

This is a continuation of application Ser. No. 08/666,392, now U.S. Pat. No. 5,929,040, filed Jun. 20, 1996 which is a 371 national phase filing of PCT/AU95/00410, filed Jul. 6, 1995.

The present invention relates generally to a method for the prophylaxis and/or treatment of skin disorders, and in particular proliferative and/or inflammatory skin disorders, and to genetic molecules useful for same. The present invention is particularly directed to genetic molecules capable of modulating growth factor interaction with its receptor on epidermal keratinocytes to inhibit, reduce or otherwise decrease stimulation of this layer of cells. The present invention contemplates, in a most preferred embodiment, a method for the prophylaxis and/or treatment of psoriasis.

Bibliographic details of the publications numerically referred to in this specification are collected at the end of the description. Sequence Identity Numbers (SEQ ID NOs.) for the nucleotide sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Psoriasis and other similar conditions are common and often distressing proliferative and/or inflammatory skin disorders affecting or having the potential to affect a significant proportion of the population. The condition arises from over proliferation of basal keratinocytes in the epidermal layer of the skin associated with inflammation in the underlying dermis. Whilst a range of treatments have been developed, none is completely effective and free of adverse side effects. Although the underlying cause of psoriasis remains elusive, there is some consensus of opinion that the condition arises at least in part from over expression of local growth factors and their interaction with their receptors supporting keratinocyte proliferation via keratinocyte receptors which appear to be more abundant during psoriasis.

One important group of growth factors are the dermally-derived insulin-like growth factors (IGFs) which support keratinocyte proliferation. In particular, IGF-I and IGF-II are ubiquitous peptides each with potent mitogenic effects on a broad range of cells. Molecules of the IGF type are also known as "progression factors" promoting "competent" cells through DNA synthesis. The IGFs act through a common receptor known as the Type I or IGF-I receptor, which is tyrosine kinase linked. They are synthesised in mesenchymal tissues, including the dermis, and act on adjacent cells of mesodermal, endodermal or ectodermal origin. The regulation of their synthesis involves growth hormone (GH) in the liver, but is poorly defined in most tissues (1).

Particular proteins, referred to as IGF binding proteins (IGFBPs), appear to be involved in autocrine/paracrine regulation of tissue IGF availability (2). Six IGFBPs have so far been identified. The exact effects of the IGFBPs is not clear and observed effects in vitro have been inhibitory or stimulatory depending on the experimental method employed (3). There is some evidence, however, that certain IGFBPs are involved in targeting IGF-I to its cell surface receptor.

Skin, comprising epidermis and underlying dermis, has GH receptors on dermal fibroblasts (4). Fibroblasts synthesize IGF-I as well as IGFBPs-3, -4, -5 and -6 (5) which may be involved in targeting IGF-I to adjacent cells as well as to the overlaying epidermis. The major epidermal cell type, the keratinocyte, does not synthesize IGF-I, but possesses IGF-I receptors and is responsive to IGF-I (6).

It is apparent, therefore, that IGF-I and other growth promoting molecules, are responsible for or at least participate in a range of skin cell activities. In accordance with the present invention, the inventors have established that abberations in the normal functioning of these molecules or abberations in their interaction with their receptors is an important factor in proliferative and/or inflammatory skin disorders. It is proposed, therefore, to target these molecules or other molecules which facilitate their functioning or interaction with their receptors to thereby ameliorate the effects of abberant activity during or leading to skin disease conditions.

Accordingly, one aspect of the present invention contemplates a method for ameliorating the effects of a proliferative and/or inflammatory skin disorder in a mammal, said method comprising contacting the proliferating and/or inflamed skin or skin capable of proliferation and/or inflammation with an effective amount of a nucleic acid molecule or chemical analogue thereof capable of inhibiting or otherwise reducing a growth factor mediated cell proliferation and/or inflammation.

Growth factor mediated cell proliferation and inflammation are also referred to as epidermal hyperplasias and may be mediated by any number of molecules such as but not limited to IGF-I, keratinocyte growth factor (KGF), transforming growth factor-α (TGFα), tumour necrosis factor-α (TNFα), interleukin-1, -4, -6 and 8 (IL-1, IL-4, IL-6 and IL-8, respectively), basic fibroblast growth factor (bFGF) or a combination of one or more of the above. The present invention is particularly described and exemplified with reference to IGF-I and its receptor (IGF-I receptor) and to IGF-I facilitating molecules, IGFBPs, since targeting these molecules according to the methods contemplated herein provides the best results to date. This is done, however, with the understanding that the present invention extends to any growth factor or cytokine-like molecule, a receptor thereof or a facilitating molecule like the IGFBPs involved in skin cell proliferation such as those molecules contemplated above and/or their receptors and/or facilitating molecules therefor.

According to this preferred embodiment, there is provided a method for ameliorating the effects of a proliferative and/or inflammatory skin disorder in a mammal, said method comprising contacting the proliferating and/or inflamed skin or skin capable of proliferation and/or inflammation with an effective amount of a nucleic acid molecule or chemical analogue thereof capable of inhibiting or otherwise reducing IGF-I mediated cell proliferation and/or inflammation.

The present invention is particularly described by psoriasis as the proliferative skin disorder. However, the subject invention extends to a range of proliferative and/or inflammatory skin disorders or epidermal hyperplasias such as but not limited to psoriasis, ichthyosis, pityriasis rubra pilaris ("PRP"), seborrhoea, keloids, keratoses, neoplasias and scleroderma, warts, benign growths and cancers of the skin.

In a preferred embodiment, therefore, the present invention is directed to a method for ameliorating the effects of psoriasis, said method comprising contacting proliferating skin or skin capable of proliferation with an effective amount of a nucleic acid molecule or chemical analogue thereof capable of inhibiting or otherwise reducing IGF-I mediated cell proliferation.

The present invention extends to any mammal such as but not limited to humans, livestock animals (e.g. horses, sheep, cows, goats, pigs, donkeys), laboratory test animals (e.g. rabbits, mice, guinea pigs), companion animals (e.g. cats, dogs) and captive wild animals. However, the instant invention is particularly directed to proliferative and/or inflammatory skin disorders such as psoriasis in humans.

The aspects of the subject invention instantly contemplated are particularly directed to the topical application of one or more suitable nucleic molecules capable of inhibiting, reducing or otherwise interfering with IGF-mediated cell proliferation and/or inflammation. More particularly, the nucleic acid molecule targets IGF-I interaction with its receptor. Conveniently, therefore, the nucleic acid molecule is an antagonist of IGF-I interaction with its receptor. Most conveniently, the nucleic acid molecule antagonist is an antisense molecule to the IGF-I receptor, to IGF-I itself or to a molecule capable of facilitating IGF-I interaction with its receptor such as but not limited to an IGFBP.

Insofar as the invention relates to IGFBPs, the preferred molecules are IGFBP-2, -3, 4, -5 and -6. The most preferred molecules are IGFBP-2 and IGFBP-3.

The nucleotide sequences of IGFBP-2 and IGFBP-3 are set forth in FIGS. 1A and 1B (SEQ ID NO. 1) and 2A and 2B (SEQ ID NO. 2), respectively. According to a particularly preferred aspect of the present invention, there is provided a nucleic acid molecule comprising at least about ten nucleotides capable of hybridising to, forming a heteroduplex or otherwise interacting with an mRNA molecule directed from a gene corresponding to a genomic form of SEQ ID NO. 1 and/or SEQ ID NO. 2 and which thereby reduces or inhibits translation of said mRNA molecule. Preferably, the nucleic acid molecule is at least about 15 nucleotides in length and more preferably at least about 20–25 nucleotides in length. However, the instant invention extends to any length nucleic acid molecule including a molecule of 100–200 nucleotides in length to correspond to the full length of or near full length of the subject genes.

The nucleotide sequence of the antisense molecules may correspond exactly to a region or portion of SEQ ID NO. 1 or SEQ ID NO. 2 or may differ by one or more nucleotide substitutions, deletions and/or additions. It is a requirement, however, that the nucleic acid molecule interact with an mRNA molecule to thereby reduce its translation into active protein.

Examples of potential antisense molecules for IGFBP-2 and IGFBP-3 are those capable of interacting with sequences selected from the lists in Examples 6 and 7, respectively.

The nucleic acid molecules in the form of an antisense molecule may be linear or covalently closed circular and single stranded or partially double stranded. A double stranded molecule may form a triplex with target mRNA or a target gene. The molecule may also be protected from, for example, nucleases, by any number of means such as using a nonionic backbone or a phosphorothioate linkage. A convenient nonionic backbone contemplated herein is ethylphosphotriester linkage or a 2'-O-methylribosyl derivative.

Examples of suitable oligonucleotide analogues are conveniently described in Ts'O et al (7).

Alternatively, the antisense molecules of the present invention may target the IGF-I gene itself or its receptor or a multivalent antisense molecule may be constructed or separate molecules administered which target at least two or an IGFBP, IGF-I and/or IGF-I-receptor. Examples of suitable antisense molecules capable of targetting the IGF-I receptor are those capable of interacting with sequences selected from the list in Example 8. One particularly useful antisense molecule is 5'-ATCTCTCCGCTTCCTTTC-3' (SEQ ID NO. 10). A particularly preferred embodiment of the present invention contemplates a method of ameliorating the effects of psoriasis, said method comprising contacting proliferating skin or skin capable of proliferation with an effective amount of one or more nucleic acid molecules or chemical analogues thereof capable of inhibiting or otherwise reducing IGF-I mediated cell proliferation wherein said one or more molecules comprises a polynucleotide capable of interacting with mRNA directed from two or more of an IGF-I gene, an IGF-I receptor gene or a gene encoding an IGFBP such as IGFBP-2 and/or IGFBP-3.

In accordance with one aspect of the present invention the nucleic acid molecule is topically applied in aqueous solution or in conjunction with a cream, ointment, oil or other suitable carrier and/or diluent. A single application may be sufficient depending on the severity or exigencies of the condition although more commonly, multiple applications are required ranging from hourly, multi-hourly, daily, multi-daily, weekly or monthly, or in some other suitable time interval. The treatment might comprise solely the application of the nucleic acid molecule or this may be applied in conjunction with other treatments for the skin proliferation and/or inflammatory disorder being treated or for other associated conditions including microbial infection, bleeding and the formation of a variety of rashes.

As an alternative to or in conjunction with antisense therapy, the subject invention extends to the nucleic acid molecule as, or incorporating, a ribozyme including a minizyme to, for example, IGF-I, its receptor or to molecules such as IGFBPs and in particular IGFBP-2 and -3. Ribozymes are synthetic nucleic acid molecules which possess highly specific endoribonuclease activity. In particular, they comprise a hybridising region which is complementary in nucleotide sequence to at least part of a target RNA. Ribozymes are well described by Haseloff and Gerlach (8) and in International Patent Application No. WO 89/05852. The present invention extends to ribozymes which target mRNA specified by genes encoding IGF-I, its receptor or one or more IGFBPs such as IGFBP-2 and/or IGFBP-3.

According to this embodiment, there is provided in a particularly preferred aspect a ribozyme comprising a hybridising region and a catalytic region wherein the hybridising region is capable of hybridising to at least part of a target mRNA sequence transcribed from a genomic gene corresponding to SEQ ID NO. 1 or SEQ ID NO. 2 wherein said catalytic domain is capable of cleaving said target mRNA sequence to reduce or inhibit IGF-I mediated cell proliferation and/or inflammation.

Yet another aspect of the present invention contemplates co-suppression to reduce expression or to inhibit translation of an endogenous gene encoding, for example, IGF-I, its receptor, or IGFBPs such as IGFBP-2 and/or -3. In co-suppression, a second copy of an endogenous gene or a substantially similar copy or analogue of an endogenous gene is introduced into a cell following topical administration. As with antisense molecules, nucleic acid molecules defining a ribozyme or nucleic acid molecules useful in co-suppression may first be protected such as by using a nonionic backbone.

The efficacy of the nucleic acid molecules of the present invention can be conveniently tested and screened using an in vitro system comprising a basal keratinocyte cell line. A particularly useful system comprises the HaCaT cell line described by Boukamp et al (9). In one assay, IGF-I is added to an oligonucleotide treated HaCaT cell line. Alternatively, growth of oligonucleotide treated HaCaT cells is observed on a feeder layer of irradiated 3T3 fibroblasts. Using such in vitro assays, it is observed that antisense oligonucleotides to IGFBP-3, for example, inhibit production of IGFBP-3 by HaCaT cells. Other suitable animal models include the nude mouse/human skin graft model (15; 16) and the "flaky skin" mouse model (17; 18). In the nude mouse model, microdermatome biopsies of psoriasis lesions are taken under local anaesthetic from volunteers then transplanted to congenital athymic (nude) mice. These transplanted human skin grafts maintain the characteristic hyperproliferating epidermis for 6–8 weeks. They are an established model for testing the efficacy of topically applied therapies for psoriasis. In the "flaky skin" mouse model, the fsn/fsn mutation produces mice with skin resembling human psoriasis. This mouse, or another mutant mouse with a similar phenotype is a further in vivo model to test the efficacy of topically applied therapies for psoriasis.

Another aspect of the present invention contemplates a pharmaceutical composition for topical administration which comprises a nucleic acid molecule capable of inhibiting or otherwise reducing IGF-I mediated cell proliferation such as psoriasis and one or more pharmaceutically acceptable carriers and/or diluents. Preferably, the nucleic acid molecule is an antisense molecule to IGF-I, the IGF-I receptor or an IGFBP such as IGFBP-2 and/or IGFBP-3 or comprises a ribozyme to one or more of these targets or is a molecule suitable for co-suppression of one or more of these targets. The composition may comprise a single species of a nuleic acid molecule capable of targeting one of IGF-I, its receptor or an IGFBP, such as IGFBP-2 or IGFBP-3 or may be a multi-valent molecule capable of targeting two or more of IGF-I, its receptor or an IGFBP, such as IGFBP-2 and/or IGFBP-3.

The nucleic acid molecules may be administered in dispersions prepared in creams, ointments, oil or other suitable carrier and/or diluent such as glycerol, liquid polyethylene glycols and/or mixtures thereof. Under ordinary conditions of storage and use, these preparations may contain a preservative to prevent the growth of microorganisms.

The pharmaceutical forms suitable for topical use include sterile aqueous solutions (where water soluble) or dispersions and powders for the extemporaneous preparation of topical solutions or dispersion. In all cases, the form is preferably sterile although this is not an absolute requirement and is stable under the conditions of manufacture and storage. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of superfactants. The prevention of the action of microorganism can be brought about by various antibacterial and antifungal agents, for example, parabens, chlorobutanol, phenol, sorbic acid, thirmerosal and the like. In many cases, it will be preferable to include isotonic agents, for example, sugars or sodium chloride.

Topical solutions are prepared by incorporating the nucleic acid molecule compound in he required amount in the appropriate solvent with various of the other ingredients numerated above, as required, followed by where necessary filter sterilization.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incomparable with the active ingredient, use thereof in the pharmaceutical compositions is contemplated. Supplementary active ingredients can also be incorporated into the compositions. Conveniently, the nucleic acid molecules of the present invention are stored in freeze-dried form and are reconstituted prior to use.

Yet another aspect of the present invention contemplates the use of a nucleic acid molecule in the manufacture of a medicament for the treatment of proliferative and/or inflammatory skin disorders mediated by a growth factor. The proliferative and/or inflammatory skin disorder is generally psoriasis and the nucleic acid molecule targets IGF-I, the IGF-I receptor and/or an IGFBP such as IGFBP-2 and/or IGFBP-3.

Still a further aspect of the present invention contemplates an agent comprising a nucleic acid molecule as hereinbefore defined useful in the treatment of proliferative and/or inflammatory skin disorders, such as psoriasis.

The present invention is further described by the following non-limiting Figures and/or Examples.

BRIEF DESCRIPTION OF THE DRAWINGS

FIGS. 1A and 1B are a representation of the nucleotide sequence of IGFBP-2 (Seq Id No: 1).

FIGS. 2A and 2D are a representation of the nucleotide sequence of IGFBP-3 (Seq. Id. No: 2).

FIGS. 3A—3G are a representation of the nucleotide sequence of IGF-1-receptor (Seq. Id. No: 3).

EXAMPLE 1

In Vitro Assay: Cells

Figure 4A:
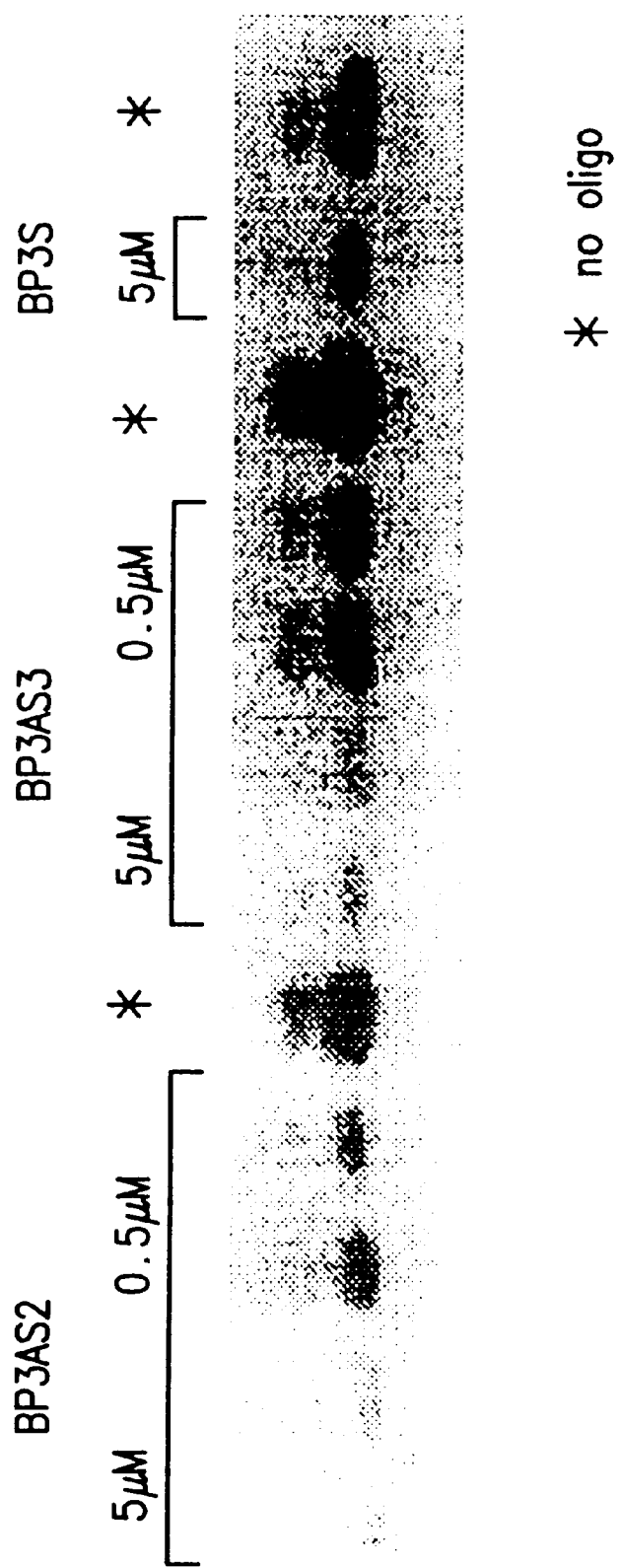
FIG. 4A is a photographic representation of a Western ligand blot of HaCaT conditioned medium showing IGFBP-3 secreted in 24 hours after 7 day treatment with phosphorothioate oligonucleotides (BP3AS2, BP3AS3 and BP3S) at 0.5 $\mu$M and 5 $\mu$M; * no oligonucleotide added.

The differentiated human keratinocyte cell line, HaCaT (9) was used in the in vitro assay. Cells at passage numbers 33 to 36 were maintained as monolayer cultures in 5% v/v $CO_2$ at 37° C. in Keratinocyte-SFM (Gibco) containing EGF and bovine pituitary extract as supplied. Media containing foetal calf serum were avoided because of the high content of IGF-I binding proteins in serum.

Feeder layer plates of lethally irradiated 3T3 fibroblasts were prepared exactly as described by Rheinwald and Green (10).

EXAMPLE 2

In Vitro Assay: Thymidine Incorporation Assay

Cells were grown to 4 days post confluence in 2 $cm^2$ wells with daily medium changes of Keratinocyte-SFM, then the medium was changed to DMEM (Cytosystems, Australia), with the following additions: 25 mM Hepes, 0.19% w/v, sodium bicarbonate, 0.03% w/v glutamine (Sigma Chemical Co, USA), 50 IU/ml penicillin and 50 $\mu$g/ml streptomycin (Flow Laboratories). After 24 hours, IGF-I or tIGF-I was added to triplicate wells, at the concentrations indicated, in 0.5 ml fresh DMEM containing 0.02% v/v bovine serum albumin (Sigma molecular biology grade) and incubated for a further 21 hours. [$^3$H]-Thymidine (0.1 $\mu$Ci/well) was then added and the cells incubated for a further 3 hours. The medium was then aspirated and the cells washed once with ice-cold PBS and twice with ice-cold 10% v/v TCA. The TCA-precipitated monolayers were then solubilized with 0.25M NaOH (200 $\mu$l/well), transferred to scintillation vials and radioactivity determined by liquid scintillation counting (Pharmacia Wallac 1410 liquid scintillation counter).

EXAMPLE 3

Western Ligand Blotting

HaCaT conditioned medium (250 $\mu$l) was concentrated by adding 750 $\mu$l cold ethanol, incubating at -20° C. for 2 hours and centrifuging at 16,000 g for 20 min at 4° C. The resulting pellet was air dried, resuspended thoroughly in non-reducing Laemmli sample buffer, heated to 90° C. for 5 minutes and separated on 12% w/v SDS-PAGE according to the method of Laemmli (1970). Separated proteins were electrophoretically transferred to nitrocellulose membrane (0.45 mm, Schleicher and Schuell, Dassel, Germany) in a buffer containing 25 mM Tris, 192 mM glycine and 20% v/v methanol. IGFBPs were then visualised by the procedure of Hossenlopp et al (11), using [$^{125}$I]-IGF-I, followed by autoradiography. Autoradiographs were scanned in a BioRad Model GS-670 Imaging Densitometer and band densities were determined using the Molecular Analyst program.

EXAMPLE 4

Antisense Oligonucleotides

Phosphorothioate oligodeoxynucleotides were synthesised by Bresatec, Adelaide, South Australia, Australia. The following antisense sequences were used: BP3AS2, 5'-GCG CCC GCT GCA TGA CGC CTG CAA C-3' (SEQ ID NO. 4), a 25 mer complementary to the start codon region of the human IGFBP-3 mRNA; BP3AS3, 5'-CGG GCG GCT CAC CTG GAG CTG GCG-3' (SEQ ID NO. 5), a 24 mer complementary to the exon 1/intron 1 splice site; BP3AS4, 5'-AGG CGG CTG ACG GCA CTA-3' (SEQ ID NO. 6), an 18 mer complementary to a region of the coding sequence lacking RNA secondary structure and oligonucleotide-dimer formation (using the computer software "OLIGO for PC"). Since BP3AS4 was found to be ineffective at inhibiting IGFBP-3 synthesis, it was used as a control. The following additional control oligonucleotide sequences were used: BP3S, 5'-CAG GCG TCA TGC AGC GGG C-3' (SEQ ID NO. 7), an 18 mer sense control sequence equivalent to the start codon region; BP3AS2NS, 5'-CGG AGA TGC CGC ATG CCA GCG CAG G-3' (SEQ ID NO. 8), a 25 mer randomised sequence with the same GC content as BP3AS2; BP3AS4NS, 5'-GAC AGC GTC GGA GCG ATC-3' (SEQ ID NO. 9), an 18 mer randomised sequence with the same GC content as BP3AS4NS. Design of the oligonucleotides was based on the human IGFBP-3 cDNA sequence of Spratt et al (12).

Cells were grown to one day post confluence in 2 $cm^2$ wells with daily medium changes of 0.5 ml Keratinocyte-SFM, then subjected to daily medium changes of Keratinocyte-SFM for a further 4 days. Daily additions of 0.5 ml fresh Keratinocyte-SFM were then continued for a further 7 days, except that at the time of medium addition, 5 $\mu$l oligonucleotide in PBS was added to give the final concentrations indicated, then the wells were shaken to mix the oligonucleotide. After the final addition, cells were incubated for 24 hours and the medium collected for assay of IGFBPs. Cells were then counted after trypsinisation in a Coulter Industrial D Counter, Coulter Bedfordshire, UK. Cell numbers after oligonucleotide treatment differed by less than 10%.

EXAMPLE 5

Antisense Oligonucleotides Inhibit IGFBP-3 Synthesis

Figure 4B:
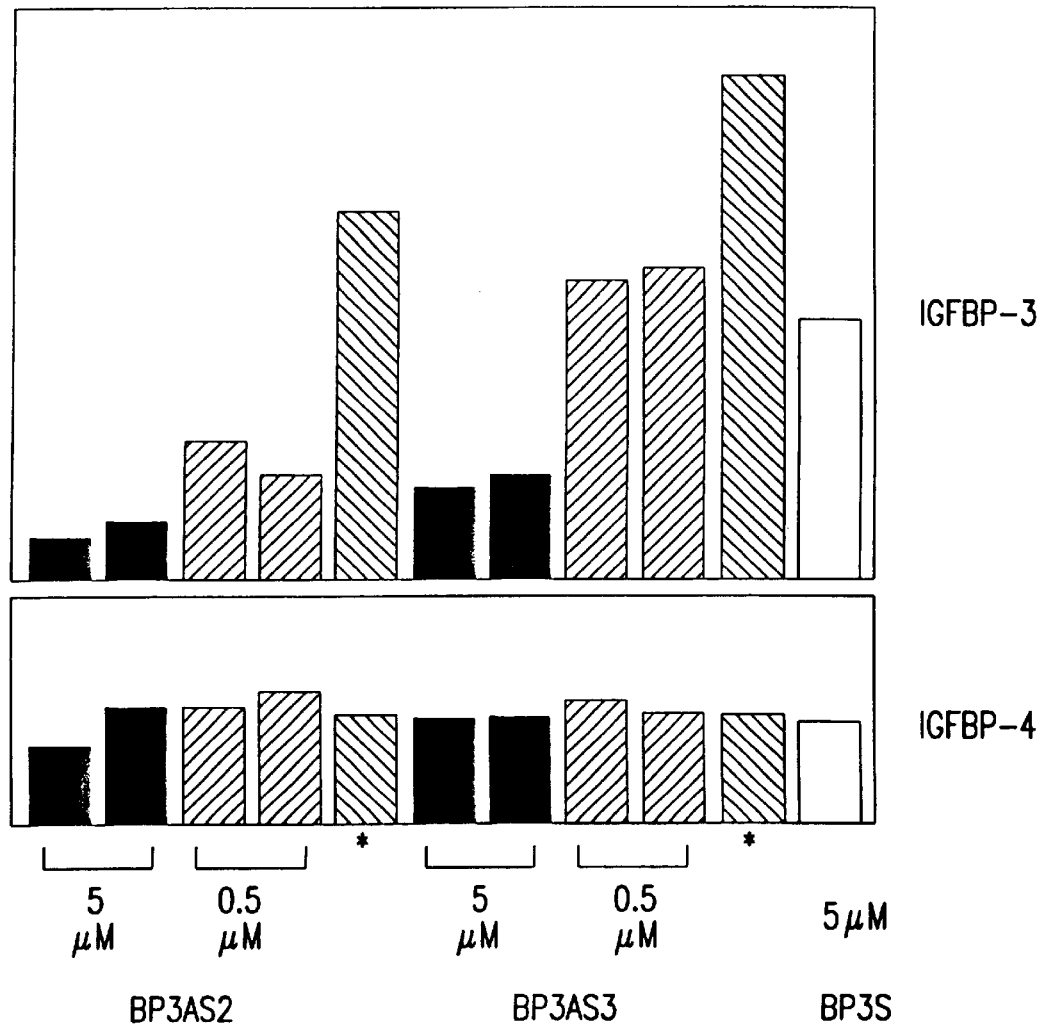
FIG. 4B is a graphical representation of a scanning imaging desitometry of Western ligand blot (FIG. 4A), showing relative band intensities of IGFBP-3 and the 24 kDa IGFBP-4 after treatment with phosphorothioate oligonucleotides; * no oligonucleotide added.

HaCaT cells secrete mainly IGFBP-3 (>95%), with the only other IGFBP detectable in HaCaT conditioned medium being IGFBP4 (<5%). The effect on IGFBP-3 and IGFBP-4 synthesis of antisense oligonucleotides at two concentrations, 5 $\mu$M and 0.5 $\mu$M, was tested. Two oligonucleotides were used, BP3AS2 and BP3AS3, directed against the start site and the intron 1/exon 1 splice site, respectively of the IGFBP-3 mRNA. As a control, a sense oligonucleotide corresponding to the start site was used. As shown in FIGS. 4A and 4B, all oligonucleotides at 5 $\mu$M caused a significant reduction of IGFBP-3 synthesis compared with untreated cells, however, the two antisense oligonucleotides inhibited IGFBP-3 synthesis of approximately 50% compared to the sense control (FIG. 4B). The antisense oligonucleotide directed to the start codon appeared to be more effective of the two, the difference being more apparent at the lower concentration of 0.5 $\mu$M. The cells of IGFBP-4 secreted by the HaCaT cells make photographic reproduction of the bands on Western ligand blots difficult, however densitometry measurements provide adequate relative quantitation. This resulted in the significant observation hat IGFBP-4 levels were unaffected by oligonucleotide addition to the cells, suggesting that the observed inhibitory effects on IGFBP-3 are specific.

Figure 5A:
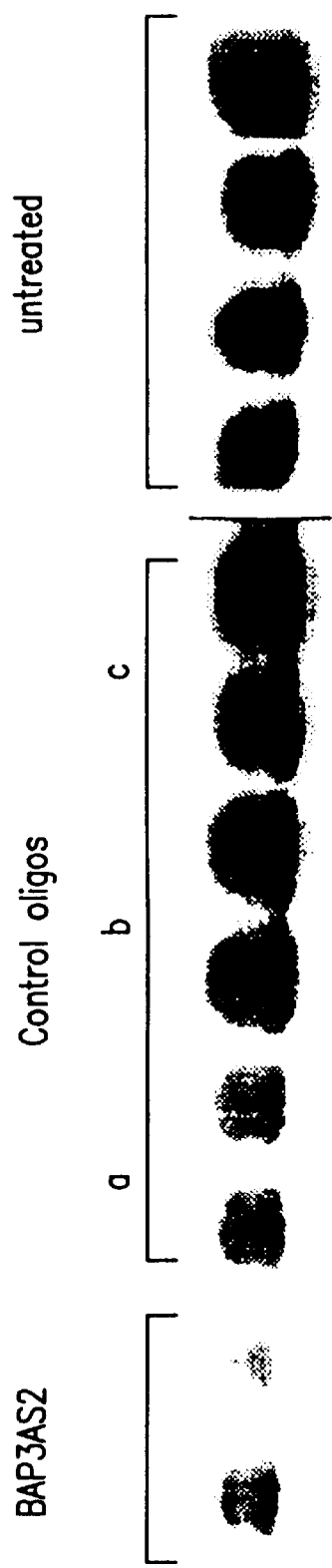
FIG. 5A is a photographic representation of a Western ligand blot of HaCaT conditioned medium showing IGFBP-3 secreted in 24 hours after 7 day treatment with phosophorothioate oligonucleotide BP3AS2 at 0.5 $\mu$M compared with several control oligonucleotides at 0.5 $\mu$M. (a) oligonucleotide BP3AS2NS; (b) oligonucleotide BP3AS4; (c) oligonucleotide BP3AS4NS; and (untreated), no oligonucleotide added.
Figure 5B:
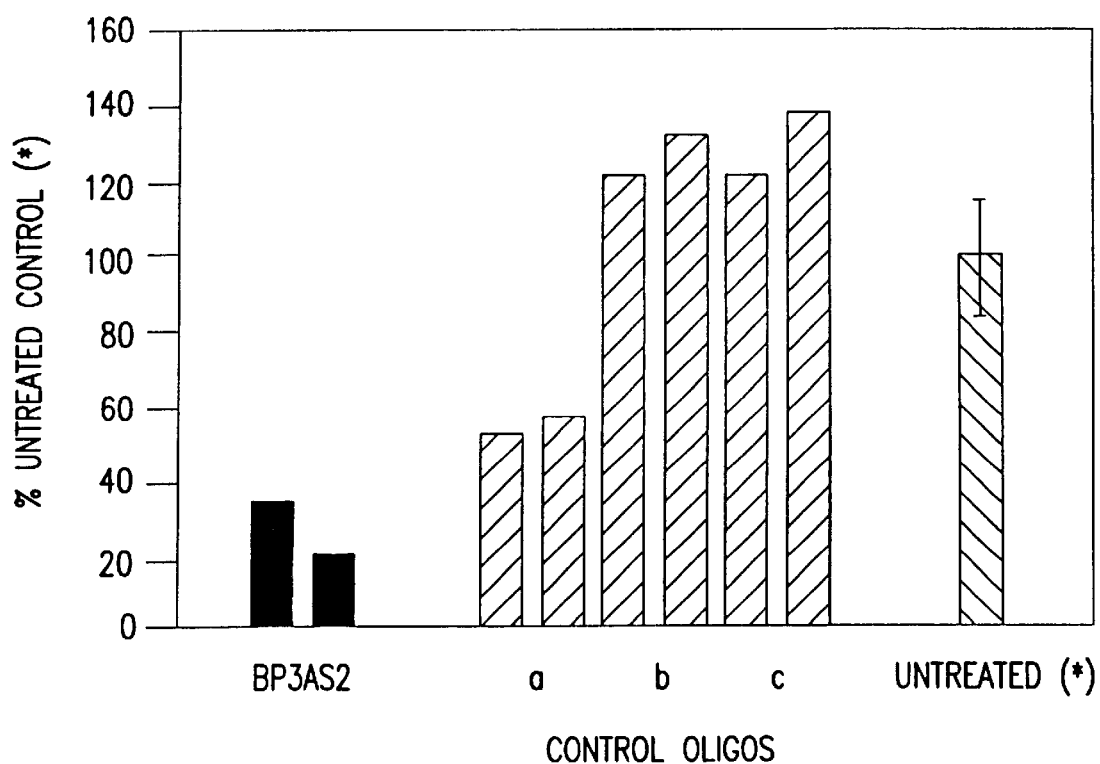
FIG. 5B is a graphical representation of a scanning imaging densitometry of Western ligand blot (FIG. 5A), showing relative band intensities of IGFBP-3 after treatment with phosphorothioate oligonucleotides as in FIG. 5A, showing IGFBP-3 band intensities expressed as a percentage of the average band intensity from conditioned, medium of cells not treated with oligonucleotide.
Figure 6:
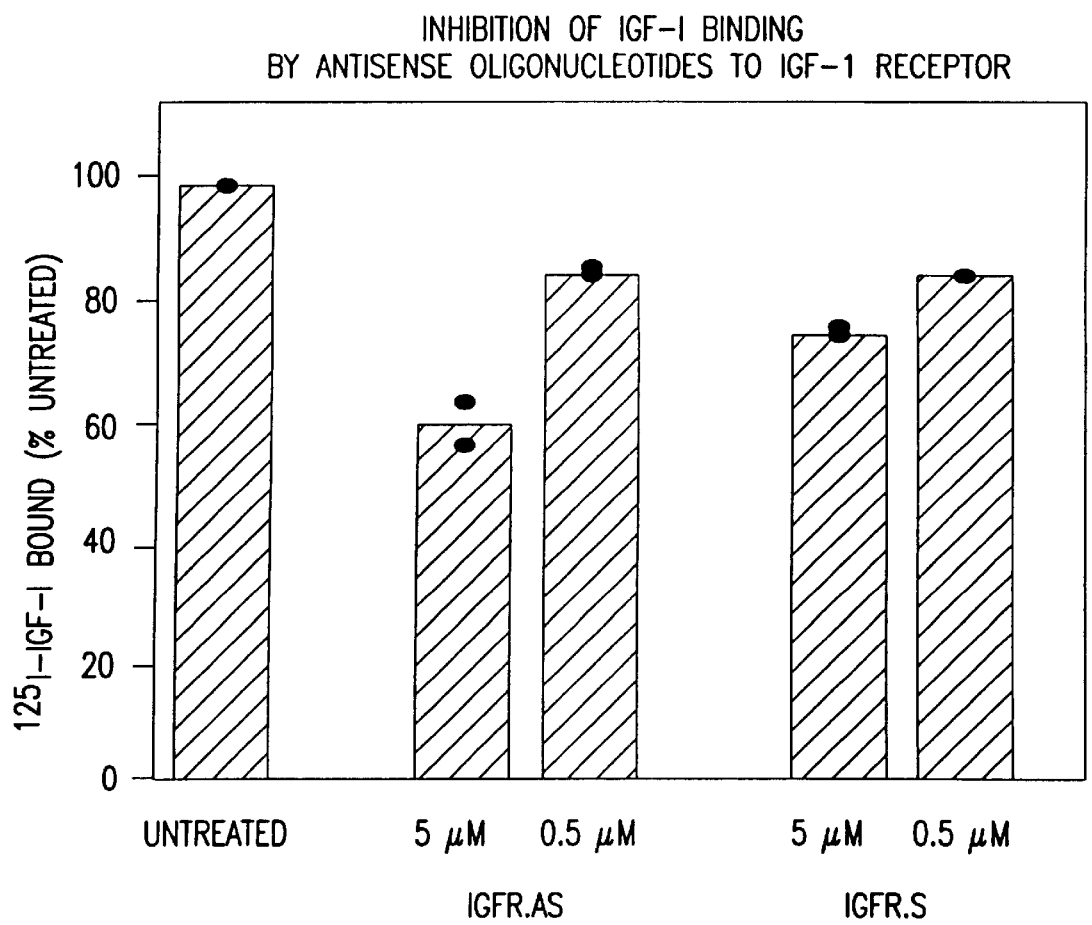
FIG. 6 is a graphical representation showing inhibition of IGF-I binding by antisense oligonucleotides to IGF-I receptor. IGFR.AS: antisense; IGFR.S: sense.

To further investigate the inhibitory effects of the more effective of the two antisense oligonucleotides, BP3AS2, inhibition by this oligonucleotide at 0.5 µM was compared with a number of control oligonucleotides, including one antisense oligonucleotide to IGFBP-3 that had proved to be ineffective at 0.5 µM. As shown in FIGS. 5A and 5B, BP3AS2 was again inhibitory, resulting in levels of IGFBP-3 of approximately 50% of the most non-specifically inhibitory control oligonucleotide, the randomised equivalent of BP3AS2. The other control oligonucleotides caused no reduction in IGFBP-3 levels at 0.5 µM, compared to untreated cells. Of possible significance is the fact that this control oligonucleotide, BP3AS2NS, like BP3AS2 itself, has the highest potential $T_m$ of the three control oligonucleotides used in this experiment, enhancing the probability of non-specific base pairing with non-target mRNAs. However, the lack of inhibition of IGFBP-4 secretion by BP3AS2 suggests that this oligonucleotide is selective even compared with the most closely related protein likely to be present in this cell line.

EXAMPLE 6

Antisense Oligonucleotides of IGFBP2

Antisense oligonucleotides to IGFBP2 may be selected from molecules capable of interacting with one or more oligonucleotides selected from oligonucleotides having the sequence of nucleotides 1–15, 2–16, 3–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 29–43, 30–44, 31–45, 32–46, 33–47, 34–48, 35–49, 36–50, 37–51, 38–52, 39–53, 40–54, 41–55, 42–56, 43–57, 44–58, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 84–98, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124; 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166–180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 186–200, 187–201, 188–202, 189–203, 190–204, 191–205, 192–206, 193–207, 194–208, 195–209, 196–210, 197–211, 198–212, 199–213, 200–214, 201–215, 202–216, 203–217, 204–218, 205–219, 206–220, 207–221, 208–222, 209–223, 210–224, 211–225, 212–226, 213–227, 214–228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288, 275–289, 276–290, 277–291, 278–292, 279–293, 280–294, 281–295, 282–296, 283–297, 284–298, 285–299, 286–300, 287–301, 288–302, 289–303, 290–304, 291–305, 292–306, 293–307, 294–308, 295–309, 296–310, 297–311, 298–312, 299–313, 300–314, 301–315, 302–315, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 350–364, 351–365, 352–366, 353–367, 354–368, 355–369, 356–370, 357–371, 358–372, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388–402, 389–403, 390–404, 391–405, 392–406, 393–407, 394–408, 395–409, 396–410, 397–411, 398–412, 399–413, 400–414, 401–415, 402–416, 403–417, 404–418, 405–419, 406–420, 407–421, 408–422, 409–423, 410–424, 411–425, 412–426, 413–427, 414–428, 415–429, 416–430, 417–431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 461–475, 462–476, 463–477, 464–478, 465–479, 466–480, 467–481, 468–482, 469–483, 470–484, 471–485, 472–486, 473–487, 474–488, 475–489, 476–490, 477–491, 478–492, 479–493, 480–494, 481–495, 482–496, 483–497, 484–498, 485–499, 486–500, 487–501, 488–502, 489–503, 490–504, 491–505, 492–506, 493–507, 494–508, 495–509, 496–510, 497–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544–558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 590–604, 591–605, 592–006, 593–607, 594–608, 595–609, 596–610, 597–611, 598–612, 599–613, 600–614, 601–615, 602–616, 603–617, 604–618, 605–619, 606–620, 607–621, 608–622, 609–623, 610–624, 611–625, 612–626, 613–627, 614–628, 615–629, 616–630, 617–631, 618–632, 619–633, 620–634, 621–635, 622–636, 623–637, 624–638, 625–639, 626–640, 627–641, 628–642, 629–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 658–672, 659–673, 660–674, 661–675, 662–676, 663–677, 664–678, 665–679, 666–680, 667–681, 668–682, 669–683, 670–684, 671–685, 672–686, 673–687, 674–688, 675–689, 676–690, 677–691, 678–692, 679–693, 680–694, 681–695, 682–696, 683–697, 684–698, 685–699, 686–700, 687–701, 688–702, 689–703, 690–704, 691–705, 692–706, 693–707, 694–708, 695–709, 696–710, 697–711, 698–712, 699–713, 700–714, 701–715, 702–716, 703–717, 704–718, 705–719, 706–720, 707–721, 708–722, 709–723, 710–724, 711–725, 712–726, 713–727, 714–728, 715–729, 716–730, 717–731, 718–732, 719–733, 720–734, 721–735, 722–736, 723–737, 724–738, 725–739, 726–740, 727–741, 728–742, 729–743, 730–744, 731–745, 732–746, 733–747, 734–748, 735–749, 736–750, 737–751, 738–752, 739–753, 740–754, 741–755, 742–756, 743–757, 744–758, 745–759, 746–760, 747–761, 748–762, 749–763, 750–764, 751–765, 752–716, 753–767, 754–768, 755–769, 756–770, 757–771, 758–772, 759–773, 760–774, 761–775, 762–776, 763–777, 764–778, 765–779, 766–780, 767–781, 768–782, 769–783, 770–784, 771–785, 772–786, 773–787, 774–788, 775–789, 776–790, 777–791, 778–792, 779–793, 780–794, 781–795, 782–796, 783–797, 784–798, 785–799, 786–800, 787–801, 788–802, 789–803, 790–804, 791–805, 792–806, 793–807, 794–808, 795–809, 796–810, 797–811, 798–812, 799–813, 800–814, 801–815, 802–816, 803–817, 804–818, 805–819, 806–820, 807–821, 808–822, 809–823, 810–824, 811–825, 812–826, 813–827, 814–828, 815–829, 816–830, 817–831, 818–832, 819–833, 820–834, 821–835, 822–836, 823–837, 824–838, 825–839, 826–840, 827–841, 828–842, 829–843, 830–844, 831–845, 832–846, 833–847, 834–848, 835–849, 836–850, 837–851, 838–852, 839–853, 840–854, 841–855, 842–856, 843–857, 844–858, 845–859, 846–860, 847–861, 848–862, 849–863, 850–864, 851–865, 852–866, 853–867, 854–868, 855–869, 856–870, 857–871, 858–872, 859–873, 860–874, 861–875, 862–876, 863–877, 864–878, 865–879, 866–880, 867–881, 868–882, 869–883, 870–884, 871–885, 872–886, 873–887, 874–888, 875–889, 876–890, 877–891, 878–892, 879–893, 880–894, 881–895, 882–896, 883–897, 884–898, 885–899, 886–990, 887–901, 888–902, 889–903, 890–904, 891–905, 892–906, 893–907, 894–908, 895–909, 896–910, 897–911, 898–912, 899–913, 900–914, 901–915, 902–916, 903–917, 904–918, 905–919, 906–920, 907–921, 908–922, 909–923, 910–924, 911–925, 912–926, 913–927, 914–928, 915–929, 916–930, 917–931, 918–932, 919–933, 920–934, 921–935, 922–936, 923–937, 924–938, 925–939, 926–940, 927–941, 928–942, 929–943, 930–944, 931–945, 932–946, 933–947, 934–948, 935–949, 936–950, 937–951, 938–952, 939–953, 940–954, 941–955, 942–956, 943–957, 944–958, 945–959, 946–960, 947–961, 948–962, 949–963, 950–964, 951–965, 952–966, 953–967, 954–968, 955–969, 956–970, 957–971, 958–972, 959–973, 960–974, 961–975, 962–976, 963–977, 964–978, 965–979, 966–980, 967–981, 968–982, 969–983, 970–984, 971–985, 972–986, 973–987, 974–988, 975–989, 976–990, 977–991, 978–992, 979–993, 980–994, 981–995, 982–996, 983–997, 984–998, 985–999, 986–1000, 987–1001, 988–1002, 989–1003, 990–1004, 991–1005, 992–1006, 993–1007, 994–1008, 995–1009, 996–1010, 997–1011, 998–1012, 999–1013, 1000–1014, 1001–1015, 1002–1016, 1003–1017, 1004–1018, 1005–1019, 1006–1020, 1007–1021, 1008–1022, 1009–1023, 1010–1024, 1011–1025, 1012–1026, 1013–1027, 1014–1028, 1015–1029, 1016–1030, 1017–1031, 1018–1032, 1019–1033, 1020–1034, 1021–1035, 1022–1036, 1023–1037, 1024–1038, 1025–1039, 1026–1040, 1027–1041, 1028–1042, 1029–1043, 1030–1044, 1031–1045, 1032–1046, 1033–1047, 1034–1048, 1035–1049, 1036–1050, 1037–1051, 1038–1052, 1039–1053, 1040–1054, 1041–1055, 1042–1056, 1043–1057, 1044–1058, 1045–1059, 1046–1060, 1047–1061, 1048–1062, 1049–1063, 1050–1064, 1051–1065, 1052–1066, 1053–1067, 1054–1068, 1055–1069, 1056–1070, 1057–1071, 1058–1072, 1059–1073, 1060–1074, 1061–1075, 1062–1076, 1063–1077, 1064–1078, 1065–1079, 1066–1080, 1067–1081, 1068–1082, 1069–1083, 1070–1084, 1071–1085, 1072–1086, 1073–1087, 1074–1088, 1075–1089, 1076–1090, 1077–1091, 1078–1092, 1079–1093, 1080–1094, 1081–1095, 1082–1096, 1083–1097, 1084–1098, 1085–1099, 1086–1100, 1087–1101, 1088–1102, 1089–1103, 1090–1104, 1091–1105, 1092–1106, 1093–1107, 1094–1108, 1095–1109, 1096–1110, 1097–1111, 1098–1112, 1099–1113, 1100–1114, 1101–1115, 1102–1116, 1103–1117, 1104–1118, 1105–1119, 1106–1120, 1107–1121, 1108–1122, 1109–1123, 1110–1124, 1111–1125, 1112–1126, 1113–1127, 1114–1128, 1115–1129, 1116–1130, 1117–1131, 1118–1132, 1119–1133, 1120–1134, 1121–1135, 1122–1136, 1123–1137, 1124–1138, 1125–1139, 1126–1140, 1127–1141, 1128–1142, 1129–1143, 1130–1144, 1131–1145, 1132–1146, 1133–1147, 1134–1148, 1135–1149, 1136–1150, 1137–1151, 1138–1152, 1139–1153, 1140–1154, 1141–1155, 1142–1156, 1143–1157, 1144–1158, 1145–1159, 1146–1160, 1147–1161, 1148–1162, 1149–1163, 1150–1164, 1151–1165, 1152–1166, 1153–1167, 1154–1168, 1155–1169, 1156–1170, 1157–1171, 1158–1172, 1159–1173, 1160–1174, 1161–1175, 1162–1176, 1163–1177, 1164–1178, 1165–1179, 1166–1180, 1167–1181, 1168–1182, 1169–1183, 1170–1184, 1171–1185, 1172–1186, 1173–1187, 1174–1188, 1175–1189, 1176–1190, 1177–1191, 1178–1192, 1179–1193, 1180–1194, 1181–1195, 1182–1196, 1183–1197, 1184–1198, 1195–1199, 1186–1200, 1187–1201, 1188–1202, 1189–1203, 1190–1204, 1191–1205, 1192–1206, 1193–1207, 1194–1208, 1195–1209, 1196–1210, 1197–1211, 1198–1212, 1199–1213, 1200–1214, 1201–1215, 1202–1216, 1203–1217, 1204–1218, 1205–1219, 1206–1220, 1207–1221, 1208–1222, 1209–1223, 1210–1224, 1211–1225, 1212–1226, 1213–1227, 1214–1228, 1215–1229, 1216–1230, 1217–1231, 1218–1232, 1219–1233, 1220–1234, 1221–1235, 1222–1236, 1223–1237, 1224–1238, 1225–1239, 1226–1240, 1227–1241, 1228–1242, 1229–1243, 1230–1244, 1231–1245, 1232–1246, 1233–1247, 1234–1248, 1235–1249, 1236–1250, 1237–1251, 1738–1252, 1239–1253, 1240–1254, 1241–1255, 1242–1256, 1243–1257, 1244–1258, 1245–1259, 1246–1260, 1247–1261, 1248–1262, 1249–1263, 1250–1264, 1251–1265, 1252–1266, 1253–1267, 1254–1268, 1255–1269, 1256–1270, 1257–1271, 1258–1272, 1259–1273, 1260–1274, 1261–1275, 1262–1276, 1263–1277, 1264–1278, 1265–1279, 1266–1280, 1267–1281, 1268–1282, 1269–1283, 1270–1284, 1271–1285, 1272–1286, 1273–1287, 1274–1288, 1275–1289, 1276–1290, 1277–1291, 1278–1292, 1279–1293, 1280–1294, 1281–1295, 1282–1296, 1283–1297, 1284–1298, 1285–1299, 1286–1300, 1287–1301, 1288–1302, 1289–1303, 1290–1304, 1291–1305, 1292–1306, 1293–1307, 1294–1308, 1295–1309, 1296–1310, 1297–1311, 1298–1312, 1299–1313, 1300–1314, 1301–1315, 1302–1316, 1303–1317, 1304–1318, 1305–1319, 1306–1320, 1307–1321, 1308–1322, 1309–1323, 1310–1324, 1311–1325, 1312–1326, 1313–1327, 1314–1328, 1315–1329, 1316–1330, 1317–1331, 1318–1332, 1319–1333, 1320–1334, 1321–1335, 1322–1336, 1323–1337, 1324–1338, 1325–1339, 1326–1340, 1327–1341, 1328–1342, 1329–1343, 1330–1344, 1331–1345, 1332–1346, 1333–1347, 1334–1348, 1335–1349, 1336–1350, 1337–1351, 1338–1352, 1339–1353, 1340–1354, 1341–1355, 1342–1356, 1343–1357, 1344–1358, 1345–1359, 1346–1360, 1347–1361, 1348–1362, 1349–1363, 1350–1364, 1351–1365, 1352–1366, 1353–1367, 1354–1368, 1355–1369, 1356–1370, 1357–1371, 1358–1372, 1359–1373, 1360–1374, 1361–1375, 1362–1376, 1363–1377, 1364–1378, 1365–1379, 1366–1380, 1367–1381, 1368–1382, 1369–1383, 1370–1384, 1371–1385, 1372–1386, 1373–1387, 1374–1388, 1375–1389, 1376–1390, 1377–1391, 1378–1392, 1379–1393, 1380–1394, 1381–1395, 1382–1396, 1383–1397, 1384–1398, 1385–1399, 1386–1400, 1387–1401, 1388–1402, 1389–1403, 1390–1404, 1391–1405, 1392–1406, 1393–1407, 1394–1408, 1395–1409, 1396–1410, 1397–1411, 1398–1412, 1399–1413, 1400–1414, 1401–1415, 1402–1416, 1403–1417, 1404–1418, 1405–1419, 1406–1420, 1407–1421, 1408–1422, 1409–1423, 1410–1424, 4111–1425, 1412–1426, 1413–1427, 1414–1428, 1415–1429, 1416–1430, 1417–1431, 1418–1432, and 1419–1433 of SEQ ID NO:1.

EXAMPLE 7

Antisense Oligonucleotides of IGFBP3

Antisense oligonucleotides to IGFBP3 may be selected from molecules capable of interacting with one or more oligonucleotides selected from oligonucleotides having the sequence of nucleotides 1–15, 2–16, 3–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 29–43, 30–44, 31–45, 32–46, 33–47, 34–48, 35–49, 36–50, 37–51, 38–52, 39–53, 40–54, 41–55, 42–56, 43–57, 44–58, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 84–98, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124, 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166–180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 86–200, 187–201, 188–202, 199–203, 190–204, 191–205, 192–206, 193–207, 194–208, 195–209, 196–210, 197–211, 198–212, 199–213, 200–214, 201–215, 202–216, 203–217, 204–218, 205–219, 206–220, 207–221, 208–222, 209–223, 210–224, 211–225, 212–226, 213–227, 214–228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288, 275–289, 276–290, 277–291, 278–292, 279–293, 280–294, 281–295, 282–296, 283–297, 284–298, 285–299, 286–300, 287–301, 288–302, 289–303, 290–304, 291–305, 292–306, 293–307, 294–308, 295–309, 296–310, 297–311, 298–312, 299–313, 300–314, 301–315, 302–316, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 350–364, 351–365, 352–366, 353–367, 354–368, 355–369, 356–370, 357–371, 358–372, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388–402, 389–403, 390–404, 391–405, 392–406, 393–407, 394–408, 395–409, 396–410, 397–411, 398–412, 399–413, 400–414, 401–415, 402–416, 403–417, 404–418, 405–419, 406–420, 407–421, 408–422, 409–423, 410–424, 411–425, 412–426, 413–427, 414–428, 415–429, 416–430, 417–431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 461–475, 462–476, 463–477, 464–478, 465–479, 466–480, 467–481, 468–482, 469–483, 470–484, 471–485, 472–486, 473–487, 474–488, 475–489, 476–490, 477–491, 478–492, 479–493, 480–494, 481–495, 482–496, 483–497, 484–498, 485–499, 480–500, 487–501, 488–502, 489–503, 490–504, 491–505, 492–506, 493–507, 494–508, 495–509, 496–510, 477–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544–558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 590–604, 591–605, 592–606, 593–607, 594–608, 595–609, 596–610, 597–611, 598–612, 599–613, 600–614, 601–615, 602–616, 603–617, 604–618, 605–619, 606–620, 607–621, 608–622, 609–623, 610–624, 611–625, 612–626, 613–627, 614–628, 615–629, 616–630, 617–631, 618–632, 619–633, 620–634, 621–635, 622–636, 623–637, 624–638, 625–639, 626–640, 627–641, 628–642, 629–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 653–672, 659–673, 660–674, 661–675, 662–676, 663–677, 664–678, 665–679, 666–680, 667–681, 668–682, 669–683, 670–684, 671–685, 672–686, 673–687, 674–688, 675–689, 676–690, 677–691, 678–692, 679–693, 680–694, 681–695, 682–696, 683–697, 684–698, 685–699, 686–700, 687–701, 688–702, 689–703, 690–704, 691–705, 692–706, 693–707, 694–708, 695–709, 696–710, 697–711, 698–712, 699–713, 700–714, 701–715, 702–716, 703–717, 704–718, 705–719, 706–720, 707–721, 708–722, 709–723, 710–724, 711–725, 712–726, 713–727, 774–728, 715–729, 716–730, 717–731, 718–732, 719–733, 720–734, 721–735, 722–736, 723–737, 724–738, 725–739, 726–740, 727–741, 728–742, 729–743, 730–744, 731–745, 732–746, 733–747, 734–748, 735–749, 736–750, 737–751, 738–752, 739–753, 740–754, 741–755, 742–756, 743–757, 744–758, 745–759, 746–760, 747–761, 748–762, 749–763, 750–764, 751–765, 752–766, 753–767, 754–768, 755–769, 756–770, 757–771, 758–772, 759–773, 760–774, 761–775, 762–776, 763–777, 764–778, 765–779, 766–780, 767–781, 768–782, 769–783, 770–784, 771–785, 772–786, 773–787, 774–788, 775–789, 776–790, 777–791, 778–792, 779–793, 780–794, 781–795, 782–796, 783–797, 784–798, 785–799, 786–800, 787–801, 788–802, 789–803, 790–804, 791–805, 792–806, 793–807, 794–808, 795–809, 796–810, 797–811, 798–812, 799–813, 800–814, 801–815, 802–816, 803–817, 804–818, 805–819, 806–820, 807–821, 808–822, 809–823, 810–824, 811–825, 812–826, 813–827, 814–828, 815–829, 816–830, 817–831, 818–832, 819–833, 820–834, 821–835, 822–836, 823–837, 824–838, 825–839, 826–840, 827–841, 828–842, 829–843, 830–844, 831–845, 832–846, 833–847, 834–848, 835–849, 836–850, 837–851, 838–852, 839–853, 840–854, 841–855, 842–856, 843–857, 844–858, 845–859, 846–860, 847–861, 848–862, 849–863, 850–864, 851–865, 852–866, 853–867, 854–868, 855–869, 856–870, 857–871, 858–872, 859–873, 860–874, 861–875, 862–876, 863–877, 864–878, 865–879, 866–880, 867–881, 868–882, 869–883, 870–884, 871–885, 872–886, 873–887, 874–888, 875–889, 876–890, 877–891, 878–892, 879–893, 880–894, 881–895, 882–896, 883–897, 884–898, 885–899, 886–900, 887–901, 888–902, 889–903, 890–904, 891–905, 892–906, 893–907, 894–908, 895–909, 896–910, 897–911, 898–912, 899–913, 900–914, 901–915, 902–916, 903–917, 904–918, 905–919, 906–920, 907–921, 908–922, 909–923, 910–924, 911–925, 912–926, 913–927, 914–928, 915–929, 916–930, 917–931, 918–932, 919–933, 920–934, 921–935, 922–936, 923–937, 924–938, 925–939, 926–940, 927–941, 928–942, 929–943, 930–944, 931–945, 932–946, 933–947, 934–948, 935–949, 936–950, 937–951, 938–952, 939–953, 940–954, 941–955, 942–956, 943–957, 944–958, 945–959, 946–960, 947–961, 948–962, 949–963, 950–964, 951–965, 952–966, 953–967, 954–968, 955–969, 956–970, 957–971, 958–972, 959–973, 960–974, 961–975, 962–976, 963–977, 964–978, 965–979, 966–980, 967–981, 968–982, 969–983, 970–984, 971–985, 972–986, 973–987, 974–988, 975–989, 9976–990, 977–991, 978–992, 979–993, 980–994, 981–995, 982–996, 983–997, 984–998, 985–999, 986–1000, 987–1001, 988–1002, 989–1003, 990–1004, 991–1005, 992–1006, 993–1007, 994–1008, 995–1009, 996–1010, 997–1011, 998–1012, 999–1013, 1000–1014, 1001–1015, 1002–1016, 1003–1017, 1004–1018, 1005–1019, 1006–1020, 1007–1021, 1008–1022, 1009–1023, 1010–1024, 1011–1025, 1012–1026, 1013–1027, 1014–1028, 1015–1029, 1016–1030, 1017–1031, 1018–1032, 1019–1033, 1020–1034, 1021–1035, 1022–1036, 1023–1037, 1024–1038, 1025–1039, 1026–1040, 1027–1041, 1028–1042, 1029–1043, 1030–1044, 1031–1045, 1032–1046, 1033–1047, 1034–1048, 1035–1049, 1036–1050, 1037–1051, 1038–1052, 1039–1053, 1040–1054, 1041–1055, 1042–1056, 1043–1057, 1044–1058, 1045–1059, 1046–1060, 1047–1061, 1048–1062, 1049–1063, 1050–1064, 1051–1065, 1052–1066, 1053–1067, 1054–1068, 1055–1069, 1056–1070, 1057–1071, 1058–1072, 1059–1073, 1060–1074, 1061–1075, 1062–1076, 1063–1077, 1064–1078, 1065–1079, 1066–1080, 1067–1081, 1068–1082, 1069–1083, 1070–1084, 1071–1085, 1072–1086, 1073–1087, 1074–1088, 1075–1089, 1076–1090, 1077–1091, 1078–1092, 1079–1093, 1080–1094, 1081–1095, 1082–1096, 1083–1097, 1084–1098, 1085–1099, 1086–1100, 1087–1101, 1088–1102, 1089–1103, 1090–1104, 1091–1105, 1092–1106, 1093–1107, 1094–1108, 1095–1109, 1096–1110, 1097–1111, 1098–1112, 1099–1113, 1100–1114, 1101–1115, 1102–1116, 1103–1117, 1104–1118, 1105–1119, 1106–1120, 1107–1121, 1108–1122, 1109–1123, 1110–1124, 1111–1125, 1112–1126, 1113–1127, 1114–1128, 1115–1129, 1116–1130, 1117–1131, 1118–1132, 1119–1133, 1120–1134, 1121–1135, 1122–1136, 1123–1137, 1124–1138, 1125–1139, 1126–1140, 1127–1141, 1128–1142, 1129–1143, 1130–1144, 1131–1145, 1132–1146, 1133–1147, 1134–1148, 1135–1149, 1136–1150, 1137–1151, 1138–1152, 1139–1153, 1140–1154, 1141–1155, 1142–1156, 1143–1157, 1144–1158, 1145–1159, 1146–1160, 1147–1161, 1148–1162, 1149–1163, 1150–1164, 1351–1165, 1152–1166, 1153–1167, 1154–1168, 1155–1169, 1156–1170, 1157–1171, 1158–1172, 1159–1173, 1160–1174, 1161–1175, 1162–1176, 1163–1177, 1164–1178, 1165–1179, 1166–1180, 1167–1181, 1168–1182, 1169–1183, 1170–1184, 1171–1185, 1172–1186, 1173–1187, 1174–1188, 1175–1189, 1176–1190, 1177–1191, 1178–1192, 1179–1193, 1180–1194, 1181–1195, 1182–1196, 1183–1197, 1184–1198, 1185–1199, 1186–1200, 1187–1201, 1188–1202, 1189–1203, 1190–1204, 1191–1205, 1192–1206, 1193–1207, 1104–1208, 1195–1209, 1196–1210, 1197–1211, 1198–1212, 1199–1213, 1200–1214, 1201–1211, 1202–1216, 1203–1217, 1204–1218, 1205–1219, 1206–1220, 1207–1221, 1208–1222, 1209–1223, 1210–1224, 1211–1225, 1212–1226, 1213–1227, 1214–1228, 1215–1229, 1216–1230, 1217–1231, 1218–1232, 1219–1233, 1920–1234, 1221–1235, 1222–1236, 1223–1237, 1224–1238, 1225–1239, 1226–1240, 1227–1241, 1228–1242, 1229–1243, 1230–1244, 1231–1245, 1232–1246, 1233–1247, 1234–1248, 1235–1249, 1236–1250, 1237–1251, 1238–1252, 1239–1253, 1240–1254, 1241–1255, 1242–1256, 1243–1257, 1244–1258, 1245–1259, 1246–1260, 1247–1261, 1248–1262, 1249–1263, 1250–1264, 1251–1265, 1252–1266, 1253–1267, 1254–1268, 1255–1269, 1256–1270, 1257–1271, 1258–1272, 1259–1273, 1260–1274, 1261–1275, 1262–1276, 1263–1277, 1264–1278, 1265–1279, 1266–1280, 1267–1281, 1268–1282, 1269–1283, 1270–1284, 1271–1285, 1272–1286, 1273–1287, 1274–1288, 1275–1289, 1276–1290, 1277–1291, 1278–1292, 1279–1293, 1280–1294, 1281–1295, 1282–1296, 1283–1297, 1284–1298, 1285–1299, 1286–1300, 1287–1301, 1288–1302, 1789–1303, 1290–1304, 1291–1305, 1292–1306, 1293–1307, 1294–1308, 1295–1309, 1296–1310, 1297–1311, 1298–1312, 1299–1313, 1300–1314, 1301–1315, 1302–1315, 1303–1317, 1304–1318, 1305–1319, 1306–1320, 1307–1321, 1308–1322, 1309–1323, 1310–1324, 1311–1325, 1312–1326, 1313–1327, 1314–1328, 1315–1329, 1316–1330, 1317–1331, 1318–1332, 1319–1333, 1320–1334, 1321–1335, 1322–1336, 1323–1337, 1324–1338, 1325–1339, 1326–1340, 1327–1341, 1328–1342, 1329–1343, 1330–1344, 1331–1345, 1332–1346, 1333–1347, 1334–1348, 1335–1349, 1336–1350, 1337–1351, 1338–1352, 1339–1353, 1340–1354, 1341–1355, 1342–1356, 1343–1357, 1344–1358, 1345–1359, 1346–1360, 1347–1361, 1348–1362, 1349–1363, 1350–1364, 1351–1365, 1352–1366, 1353–1367, 1354–1368, 1355–1369, 1356–1370, 1357–1371, 1358–1372, 1359–1373, 1360–1374, 1361–1375, 1362–1376, 1363–1377, 1364–1378, 1365–1379, 1366–1380, 1367–1381, 1368–1382, 1309–1383, 1370–1384, 1371–1385, 1372–1386, 1373–1387, 1374–1388, 1375–1389, 1376–1390, 1377–1391, 1378–1392, 1379–1393, 1380–1394, 1381–1395, 1382–1390, 1383–1397, 1384–1398, 1385–1399, 1386–1400, 1387–1401, 1388–1402, 1389–1403, 1390–1404, 1391–1405, 1392–1406, 1393–1407, 1394–1408, 1395–1409, 1396–1410, 1397–1411, 1398–1412, 1399–1413, 1400–1414, 1401–1415, 1402–1416, 1403–1417, 1404–1418, 1405–1419, 1406–1420, 1407–1421, 1408–1422, 1409–1423, 1410–1424, 1411–1425, 1412–1426, 1413–1427, 1414–1428, 1415–1429, 1416–1430, 1417–1431, 1418–1432, 1419–1433, 1420–1434, 1421–1435, 1422–1436, 1423–1437, 1424–1438, 1425–1439, 1426–1440, 1427–1441, 1428–1442, 1429–1443, 1430–1444, 1431–1445, 1432–1446, 1433–1447, 1434–1448, 1435–1449, 1436–1450, 1437–1451, 1438–1452, 1439–1453, 1440–1454, 1441–1455, 1442–1456, 1443–1457, 1444–1458, 1445–1459, 1446–1460, 1447–1461, 1448–1462, 1449–1463, 1450–1464, 1451–1465, 1452–1466, 1453–3467, 1454–1468, 1455–1469, 1456–1470, 1457–1471, 1458–1472, 1459–1473, 1460–1474, 1461–1475, 1462–1476, 1463–1477, 1464–1478, 1465–1479, 1466–1480, 1467–1481, 1468–1482, 1409–1483, 1470–1484, 1471–1485, 1472–1486, 1473–1487, 1474–1488, 1475–1489, 1476–1490, 1477–1491, 1478–1492, 1479–1493, 1480–1494, 1481–1495, 1482–1496, 1483–1497, 1484–1498, 1485–1499, 1486–1500, 1487–1501, 1488–1502, 1489–1503, 1490–1504, 1491–1505, 1492–1506, 1493–1507, 1494–1508, 1495–1509, 1496–1510, 1497–1511, 1498–1513, 1499–1514, 1500–1515, 1501–1515, 1502–1516, 1503–1517, 1504–1518, 1505–1519, 1506–1520, 1507–1521, 1508–1522, 1509–1523, 1510–1524, 1511–1525, 1512–1526, 1513–1527, 1514–1528, 1515–1529, 1516–1530, 1517–1531, 1518–1532, 1519–1533, 1520–1534, 1521–1535, 1522–1536, 1523–1537, 1524–1538, 1525–1539, 1526–1540, 1527–1541, 1528–1542, 1529–1543, 1530–1544, 1531–1545, 1532–1546, 1533–1547, 1534–1548, 1535–1549, 1536–1550, 1537–1551, 1538–1552, 1539–1553, 1540–1554, 1541–1555, 1542–1556, 1543–1557, 1544–1558, 1545–1559, 1546–1560, 1547–1561, 1548–1562, 1549–1563, 1550–1564, 1551–1565, 1552–1566, 1553–1567, 1554–1568, 1555–1569, 1556–1570, 1557–1571, 1558–1572, 1559–1573, 1560–1574, 1561–1575, 1562–1576, 1563–1577, 1564–1578, 1565–1579, 1566–1580, 1567–1581, 1568–1582, 1569–1583, 1570–1584, 1571–1585, 1572–1586, 1573–1587, 1574–1588, 1575–1589, 1576–1590, 1577–1591, 1578–1592, 1579–1593, 1580–1594, 1581–1595, 1582–1596, 1583–1597, 1584–1598, 1585–1599, 1536–1600, 1587–1601, 1588–1602, 1589–1603, 1590–1604, 1591–1605, 1592–1606, 1593–1607, 1594–1608, 1595–1609, 1596–1610, 1597–1611, 1598–1612, 1599–1613, 1600–1614, 1601–1615, 1602–1616, 1603–1617, 1604–1618, 1605–1619, 1606–1620, 1607–1621, 1608–1622, 1609–1623, 1610–1624, 1611–1625, 1612–1626, 1613–1627, 1614–1628, 1615–1629, 1616–1630, 1617–1631, 1618–1632, 1619–1633, 1620–1634, 1621–1635, 1622–1636, 1623–1637, 1624–1638, 1625–1639, 1626–1640, 1627–1641, 1628–1642, 1629–1643, 1630–1644, 1631–1645, 1632–1646, 1633–1647, 1634–1648, 1635–1649, 1636–1650, 1637–1651, 1638–1652, 1639–1653, 1640–1654, 1641–1655, 1642–1656, 1643–16577 1644–1658, 1645–1659, 1646–1660, 1647–1661, 1648–1662, 1649–1663, 1630–1664, 1651–1665, 1652–1666, 1653–1667, 1654–1668, 1655–1669, 1656–1670, 1657–1671, 1658–1672, 1659–1673, 1660–1674, 1661–1675, 1662–1676, 1663–1677, 1064–1678, 1665–1679, 1666–1680, 1667–1681, 1668–1682, 1669–1683, 1670–1684, 1671–1685, 1672–1686, 1673–1687, 1674–1688, 1675–1689, 1676–1690, 1677–1691, 1678–1692, 1679–1693, 1680–1694, 1681–1695, 1682–1696, 1683–1697, 1684–1698, 1685–1699, 1686–1700, 1687–1701, 1688–1702, 1689–1703, 1690–1704, 1691–1705, 1692–1706, 1693–1707, 1694–1708, 1695–1709, 1696–1710, 1697–1711, 1698–1712, 1699–1713, 1700–1714, 1701–1715, 1702–1716, 1703–1717, 1704–1718, 1705–1719, 1706–1720, 1707–1721, 1708–1722, 1709–1723, 1710–1724, 1711–1725, 1712–1726, 1713–1727, 1714–1728, 1715–1729, 1716–1730, 1717–1731, 1718–1732, 1719–1733, 1720–1734, 1721–1735, 1722–1736, 1723–1737, 1724–1738, 1725–1739, 1726–1740, 1727–1741, 1728–1742, 1729–1743, 1730–1744, 1731–1745, 1732–1746, 1733–1747, 1734–1748, 1735–1749, 1736–1750, 1737–1751, 1738–1752, 1739–1753, 1740–1754, 1741–1755, 1742–1756, 1743–1757, 1744–1758, 1745–1759, 1746–1760, 1747–1761, 1748–1762, 1749–1763, 1750–1764, 1751–1765, 1752–1766, 1753–1767, 1754–1768, 1755–1769, 1756–1770, 1757–1771, 1758–1772, 1759–1773, 1760–1774, 1761–1775, 1762–1776, 1763–1777, 1764–1778, 1765–1779, 1766–1780, 1767–1781, 1768–1782, 1769–1783, 1770–1784, 1771–1785, 1772–1786, 1773–1787, 1774–1788, 1775–1789, 1776–1790, 1777–1791, 1778–1792, 1779–1793, 1780–1794, 1781–1795, 1782–1796, 1783–1797, 1784–1798, 1785–1799, 1786–1800, 1787–1801, 1788–1802, 1789–1803, 1790–1804, 1791–1805, 1792–1806, 1793–1807, 1794–1808, 1795–1809, 1796–1810, 1797–1811, 1798–1812, 1799–1813, 1800–1814, 1801–1815, 1802–1816, 1803–1817, 1804–1818, 1805–1819, 1806–1820, 1807–1821, 1808–1822, 1809–1823, 1810–1824, 1811–1825, 1812–1826, 1813–1827, 1814–1828, 1815–1829, 1816–1830, 1817–1831, 1818–1832, 1819–1833, 1820–1834, 1821–1835, 1822–1836, 1823–1837, 1824–1838, 1825–1839, 1826–1840, 1827–1841,
1828–1842, 1829–1843, 1830–1844, 1831–1845,
1832–1846, 1833–1847, 1834–1848, 1835–1849,
1836–1850, 1837–1851, 1838–1852, 1839–1853,
1840–1854, 1841–1855, 1842–1856, 1843–1857,
1844–1858, 1845–1859, 1846–1860, 1847–1861,
1848–1862, 1849–1863, 1850–1864, 1851–1865,
1852–1866, 1853–1867, 1854–1868, 1855–1869,
1856–1870, 1857–1871, 1858–1872, 1859–1873,
1860–1874, 1861–1875, 1862–1876, 1863–1877,
1864–1878, 1865–1879, 1866–1880, 1867–1881,
1868–1882, 1869–1883, 1870–1884, 1871–1885,
1872–1886, 1873–1887, 1874–1888, 1875–1889,
1876–1890, 1877–1891, 1878–1892, 1879–1893,
1880–1894, 1881–1895, 1882–1896, 1883–1897,
1884–1898, 1885–1899, 1886–1900, 1887–1901,
1888–1902, 1889–1903, 1890–1904, 1891–1905,
1892–1906, 1893–1907, 1894–1908, 1895–1909,
1896–1910, 1897–1911, 1898–1912, 1899–1913,
1900–1914, 1901–1915, 1902–1916, 1903–1917,
1904–1918, 1905–1919, 1906–1920, 1907–1921,
1908–1922, 1909–1923, 1910–1924, 1911–1925,
1912–1926, 1913–1927, 1914–1928, 1915–1929,
1916–1930, 1917–1931, 1918–1932, 1919–1933,
1920–1934, 1921–1935, 1922–1936, 1923–1937,
1924–1938, 1925–1939, 1926–1940, 1927–1941,
1928–1942, 1929–1943, 1930–1944, 1931–1945,
1932–1946, 1933–1947, 1934–1948, 1935–1949,
1936–1950, 1937–1951, 1938–1952, 1939–1953,
1940–1954, 1941–1955, 1942–1956, 1943–1957,
1944–1958, 1945–1959, 1946–1960, 1947–1961,
1948–1962, 1949–1963, 1950–1964, 1151–1965,
1952–1966, 1953–1967, 1954–1968, 1955–1969,
1956–1970, 1957–1971, 1958–1972, 1959–1973,
1960–1974, 1961–1975, 1962–1976, 1963–1977,
1964–1978, 1965–1979, 1966–1980, 1967–1981,
1968–1982, 1969–1983, 1970–1984, 1971–1985,
1972–1986, 1973–1987, 1974–1988, 1975–1989,
1976–1990, 1977–1991, 1978–1992, 1979–1993,
1980–1994, 1981–1995, 1982–1996, 1983–1997,
1984–1998, 1985–1999, 1986–2000, 1987–2001,
1988–2002, 1989–2003, 1990–2004, 1991–2005,
1992–2006, 1993–2007, 1994–2008, 1995–2009,
1996–2010, 1997–2011, 1998–2012, 1999–2013,
2000–2014, 2001–2015, 2002–2016, 2003–2017,
2004–2018, 2005–2019, 2006–2020, 2007–2021,
2008–2022, 2009–2023, 2010–2024, 2011–2025,
2012–2026, 2013–2027, 2014–2028, 2015–2029,
2016–2030, 2017–2031, 2018–2032, 2019–2033,
2020–2034, 2021–2035, 2022–2036, 2023–2037,
2024–2038, 2025–2039, 2026–2040, 2027–2041,
2028–2042, 2029–2043, 2030–2044, 2031–2045,
2032–2046, 2033–2047, 2034–2048, 2035–2049,
2036–2050, 2037–2051, 2038–2052, 2039–2053,
2040–2054, 2041–2055, 2042–2056, 2043–2057,
2044–2058, 2045–2059, 2046–2060, 2047–2061,
2048–2062, 2049–2063, 2050–2064, 2051–2065,
2052–2066, 2053–2067, 2054–2068, 2055–2069,
2056–2070, 2057–2071, 2058–2072, 2059–2073,
7060–2074, 2061–2075, 2062–2076, 2063–2077,
2064–2078, 2065–2079, 2066–2080, 2067–2081,
2068–2082, 2069–2083, 2070–2084, 2071–2085,
2072–2086, 2073–2087, 2074–2088, 2075–2089,
2076–2090, 2077–2091, 2078–2092, 2079–2093,
2080–2094, 2081–2095, 2082–2096. 2083–2097,
2084–2098, 2085–2099, 2086–2100, 2087–2101,
2088–2102, 2089–2103, 2090–2104, 2091–2105,
2092–2106, 2093–2107, 2094–2108, 2095–2109,
2096–2110, 2097–2111, 2098–2112, 2099–2113,
2100–2114, 2101–2115, 2102–2116, 2103–2117,
2104–2118, 2105–2119, 2106–2120, 2107–2121,
2108–2122, 2109–2123, 2110–2124, 2111–2125,
2112–2126, 2113–2127, 2114–2128, 2115–2129,
2116–2130, 2117–2131, 2118–2132, 2119–2133,
2120–2134, 2121–2135, 2122–2136, 2123–2137,
2124–2138, 2125–2139, 2126–2140, 2127–2141,
2128–2142, 2129–2143, 2130–2144, 2131–2145,
2132–2146, 2133–2147, 2134–2148, 2135–2149,
2136–2150, 2137–2151, 2138–2152, 2139–2153,
2140–2154, 2141–2155, 2142–2156, 2143–2157,
2144–2158, 2145–2159, 2146–2160, 2147–2161,
2148–2162, 2149–2163, 2150–2164, 2151–2165,
2152–2166, 2153–2167 2154–2168, 2155–2169, 2156,
–2170, 2157–2171, 2158–2172, 2159–2173, 2160–2174,
2161–2175, 2162–2176, 2163–2177, 2164–2178,
2165–2179, 2166–2180, 2167–2181, 2168–2182,
2169–2183, 2170–2184, 2171–2185, 2172–2186,
2173–2187, 2174–2188, 2175–2189, 2176–2190,
2177–2191, 2178–2192, 2179–2913, 2180–2194,
2181–2195, 2182–2196, 2183–2197, 2184–2198,
2185–2199, 2186–2200, 2187–2201, 2188–2202,
2129–2203, 2190–2204, 2191–2205, 2192–2206,
2193–2207, 2194–2208, 2195–2209, 2196–2210,
2197–2211, 2198–2212, 2199–2213, 2200–2214,
2201–2215, 2202–2216, 2203–2217, 2214–2218,
2205–2219, 2206–2220, 2227–2221, 2208–2222,
2209–2223, 2210–2224, 2211–2225, 2212–2226,
2213–2227, 2214–2228, 2215–2229, 2216–2230,
2217–2231, 2218–2232, 2219–2233, 2220–2234,
2221–2235, 2222–2236, 2223–2237, 2224–2238,
2225–2239, 2226–2240, 2227–2241, 2228–2242,
2229–2243, 2230–2244, 2231–2245, 2232–2246,
2213–2247, 2234–2248, 2235–2249, 2236–2250,
2237–2251, 2238–2252, 2239–2253, 2240–2254,
2241–2255, 2242–2256, 2243–2257, 2244–2258,
2245–2259, 2246–2260, 2247–2261, 2248–2262,
2249–2263, 2250–2264, 2251–2265, 2252–2266,
2253–2267, 2254–2268, 2255–2269, 2256–2270,
2257–2271, 2258–2272, 2259–2273, 2260–2274,
2261–2275, 2262–2276, 2263–2277, 2264–2278,
2265–2279, 2266–2280, 2267–2281, 2268–2282,
2269–2283, 2270–2284, 2271–2283, 2272–2286,
2273–2287, 2274–2288, 2275–2289, 2276–2290,
2277–2291, 2278–2299, 2279–2293, 2280–2294,
2281–2295, 2282–2296, 2283–2297, 2284–2298,
2285–2299, 2286–2300, 2287–2301, 2288–2302,
2289–2303, 2290–2304, 2291–2305, 2292–2306,
2293–2307, 2294–2308, 2295–2309, 2296–2310,
2297–2311, 2298–2312, 2299–2313, 2300–2314,
2301–2315, 2302–2315, 2303–2317, 2304–2318,
2305–2319, 2306–2320, 2307–2321, 2308–2322,
2309–2323, 2310–2324, 2311–2325, 2312–2326,
2313–2327, 2314–2328, 2315–2329, 2316–2330,
2317–2331, 2318–2332, 2319–2333, 2320–2334,
2321–2335, 2322–2336, 2323–2337, 2324–2338,
2325–2339, 2326–2340, 2327–2341, 2328–2342,
2329–2343, 2330–2344, 2331–2345, 2332–2346,
2333–2347, 2334–2348, 2335–2349, 2336–2350,
2337–2351, 2338–2352, 2339–2353, 2340–2354,
2341–2355, 2342–2356, 2343–2357, 2344–2358,
2345–2359, 2346–2360, 2347–2361, 2348–2362,
2349–2363, 2350–2364, 2351–2365, 2352–2366,
2353–2367, 2354–2368, 2355–2369, 2356–2370,
2357–2371, 2358–2372, 2359–2373, 2360–2374, 2361–2375, 2362–2376, 2363–2377, 2364–2378, 2365–2379, 2366–2380, 2367–2381, 2368–2382, 2369–2383, 2370–2384, 2371–2385, 2372–2386, 2373–2387, 2374–2388, 2375–2389, 2376–2390, 2377–2391, 2378–2392, 2379–2393, 2380–2394, 2381–2395, 2382–2396, 2383–2397, 2384–2398, 2385–2399, 2386–2400, 2387–2401, 2388–2402, 2389–2403, 2390–2404, 2391–2405, 2392–2406, 2393–2407, 2394–2408, 2395–2409, 2396–2410, 2397–2411, 2398–2412, 2399–2413, 2400–1412, 2401–2415, 2402–2416, 2403–2417, 2404–2418, 2405–2419, 2406–2420, 2407–2421, 2408–2422, 2409–2423, 2410–2424, 2411–2425, 2412–2426, 2413–2427, 2414–2428, 2415–2429, 2416–2430, 2417–2431, 2418–2432, 2419–2433, 2420–2434, 2421–2435, 2422–2436, 2423–2437, 2424–2438, 2425–2439, 2426–2440, 2427–2441, 2428–2442, 2429–2443, 2430–2444, 2431–2445, 2432–2446, 2433–2447, 2434–2448, 2435–2449, 2436–2450, 2437–2451, 2438–2452, 2439–2453, 2440–2454, 2441–2455, 2442–2456, 2443–2457, 2444–2458, 2445–2459, 2446–2460, 2447–2461, 2448–2462, 2449–2463, 2450–2464, 2451–2465, 2452–2466, 2453–2467, 2454–2468, 2455–2469, 2456–2470, 2457–2471, 2458–2472, 2459–2437, and 2460–2474 of SEQ ID NO:2.

EXAMPLE 8

Antisense Oligonucleotides of IGF-I Receptor

Antisense oligonucleotides to IGF-I receptor may be selected from molecules capable of interacting with one or more oligonucleotides selected from oligonucleotides having the sequence of nucleotides 1–15, 2–16, 35–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 29–43, 30–44, 31–45, 32–46, 33–47, 34–48, 35–49, 36–50, 37–51, 38–52, 39–53, 40–54, 41–55, 42–56, 43–57, 44–58, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 84–98, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124, 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166–180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 186–200, 187–201, 188–202, 189–203, 190–204, 191–205, 192–206, 193–207, 194–208, 195–209, 196–210, 197–211, 198–212, 199–213, 200–214, 201–215, 202–216, 203–217, 204–218, 205–219, 206–220, 207–221, 208–222, 209–223, 210–224, 211–225, 212–226, 213–227, 214–228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288, 275–289, 276–290, 277–291, 278–292, 279–293, 280–294, 281–295, 282–296, 283–297, 284–298, 285–299, 286–300, 287–301, 288–302, 289–303, 290–304, 291–305, 212–306, 293–307, 294–308, 295–309, 296–310, 297–311, 298–312, 299–313, 300–314, 301–315, 302–315, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 330–364, 351–365, 352–366, 353–367, 354–368, 355–369, 356–370, 357–371, 358–172, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388–402, 389–403, 390–404, 391–405, 392–406, 393–407, 394–408, 395–409, 396–410, 397–411, 398–412, 399–413, 400–414, 401–415, 402–416, 403–417, 404–418, 405–419, 406–420, 407–421, 408–422, 409–423, 410–424, 411–425, 412–426, 413–427, 414–428, 415–429, 416–430, 417–431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 401–475, 462–476, 463–477, 464–478, 465–479, 466–480, 467–481, 468–482, 469–483, 470–484, 471–485, 472–486, 473–487, 474–488, 475–489, 476–490, 477–491, 478–492, 479–493, 480–494, 481–495, 482–496, 483–497, 484–498, 485–499, 486–500, 487–501, 488–502, 489–503, 490–504, 491–505, 492–506, 493–507, 494–508, 495–509, 496–510, 497–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544–558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 590–604, 591–605, 592–606, 593–607, 594–608, 595–609, 596–610, 597–611, 598–612, 599–613, 600–614, 601–615, 602–616, 603–617, 604–618, 605–619, 606–620, 607–621, 608–622, 609–623, 610–624, 611–625, 612–626, 613–627, 614–628, 615–629, 610–630, 617–631, 618–632, 619–633, 620–634, 621–635, 622–636, 623–637, 624–638, 625–639, 626–640, 627–641, 628–642, 620–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 658–672, 659–673, 660–674, 661–675, 662–676, 663–677, 664–678, 665–679, 666–680, 667–681, 668–682, 669–683, 670–684, 671–685, 672–686, 673–367, 674–688, 675–689, 676–690, 677–691, 678–692, 679–693, 680–694, 681–695, 682–696, 683–697, 684–698, 685–699, 686–700, 687–701, 688–702, 789–703, 690–704, 691–705, 792–706, 693–707, 694–708, 695–709, 696–710, 697–711, 698–712, 699–713, 700–714, 701–715, 702–716, 703–717, 704–718, 705–719, 706–720, 707–721, 708–722, 709–723, 710–724, 711–725, 772–726, 713–727, 714–728, 715–729, 716–730, 717–731, 718–732, 719–733, 720–734, 721–735, 722–736, 723–737, 724–738, 725–739, 726–740, 727–741, 728–742, 729–743, 730–744, 731–745, 732–746, 733–747, 734–748, 735–749, 736–750, 737–751, 738–752, 739–753, 740–754, 741–755, 742–756, 743–757, 744–758, 745–759, 746–760, 747–761, 748–762, 749–763, 750–764, 751–765, 752–766, 753–767, 754–768, 755–769, 756–770, 757–771, 758–772, 759–773, 760–774, 761–775, 762–776, 763–777, 764–778, 765–779, 766–780, 767–781, 768–782, 769–783, 770–784, 771–785, 772–786, 773–787, 774–788, 175–789, 776–790, 777–791, 778–792, 779–793, 780–794, 781–795, 782–796, 783–797, 784–798, 785–799, 786–800, 787–801, 788–802, 789–803, 790–804, 791–805, 702–806, 793–807, 794–808, 795–809, 796–810, 797–811, 798–812, 799–813, 800–814, 801–815, 802–816, 803–817, 804–818, 805–819, 806–820, 807–821, 808–822, 809–823, 810–824, 811–825, 812–826, 813–827, 814–828, 815–829, 816–830, 817–831, 818–832, 819–833, 820–834, 821–835, 822–836, 823–837, 824–838, 825–839, 826–840, 827–841, 828–842, 829–843, 830–844, 831–845, 832–846, 833–847, 834–848, 835–849, 836–850, 837–851, 838–852, 839–853, 840–854, 841–855, 842–856, 843–857, 844–858, 845–859, 846–860, 847–861, 848–862, 849–863, 850–864, 851–865, 852–866, 853–867, 854–868, 855–869, 856–870, 857–871, 858–872, 859–873, 860–874, 861–875, 862–876, 863–877, 864–878, 865–879, 866–880, 867–881, 868–882, 869–883, 870–884, 871–885, 872–886, 873–887, 874–888, 875–889, 876–890, 877–891, 878–892, 879–893, 880–894, 881–895, 882–896, 883–897, 884–898, 885–899, 886–900, 887–901, 888–902, 889–903, 890–904, 891–905, 892–906, 893–907, 894–908, 995–909, 896–910, 897–911, 898–912, 899–913, 900–914, 901–915, 902–916, 903–917, 904–918, 905–919, 906–920, 907–921, 908–922, 909–923, 910–924, 911–925, 912–926, 913–927, 914–928, 915–929, 916–930, 917–931, 918–932, 919–933, 920–934, 921–935, 922–936, 923–937, 924–938, 925–939, 926–940, 927–941, 928–942, 929–943, 930–944, 931–945, 932–946, 903–947, 934–948, 935–949, 936–950, 937–951, 938–952, 939–953, 940–954, 941–955, 942–956, 943–957, 944–958, 945–959, 946–960, 947–961, 948–962, 949–963, 950–964, 951–965, 952–966, 953–967, 954–968, 955–969, 956–970, 957–971, 958–972, 959–973, 960–974, 961–975, 962–976, 963–977, 964–978, 965–979, 966–980, 967–981, 968–982, 969–983, 970–984, 971–985, 972–986, 973–987, 974–988, 975–989, 976–990, 977–991, 978–992, 979–993, 980–994, 981–995, 982–996, 983–997, 984–998, 985–999, 986–1000, 987–1001, 988–1002, 989–1003, 990–1004, 991–1005, 992–1006, 993–1007, 994–1008, 995–1009, 996–1010, 997–1011, 998–1012, 999–1013, 1000–1014, 1101–1015, 1002–1016, 1003–1017, 1004–1018, 1005–1019, 1006–1020, 1007–1021, 1008–1022, 1009–1023, 1010–1024, 1011–1025, 1012–1026, 1013–1027, 1014–1028, 1015–1029, 1016–1030, 1017–1031, 1018–1032, 1019–1033, 1020–1034, 1021–1035, 1022–1036, 1023–1037, 1024–1038, 1025–1039, 1026–1040, 1027–1041, 1028–1042, 1029–1043, 1030–1044, 1031–1045, 1032–1046, 1033–1047, 1034–1048, 1035–1049, 1036–1050, 1037–1051, 1038–1052, 1039–1053, 1040–1054, 1041–1055, 1042–1056, 1043–1057, 1044–1058, 1045–1059, 1046–1060, 1047–1061, 1048–1062, 1049–1063, 1050–1064, 1051–1065, 1052–1066, 1053–1067, 1054–1068, 1055–1069, 1056–1070, 1057–1071, 1058–1072, 1059–1073, 1060–1074, 1061–1075, 1062–1076, 1063–1077, 1064–1078, 1065–1079, 1066–1080, 1067–1081, 1068–1082, 1069–1083, 1070–1084, 1071–1085, 1072–1086, 1073–1087, 1074–1088, 1075–1089, 1076–1090, 1077–1091, 1078–1092, 1079–1093, 1080–1094, 1081–1095, 1082–1096, 1083–1097, 1084–1098, 1085–1099, 1086–1100, 1087–1101, 1088–1102, 1089–1103, 1090–1104, 1091–1105, 1092–1106, 1093–1107, 1094–1108, 1095–1109, 1096–1110, 1097–1111, 1098–1112, 1099–1113, 1100–1114, 1101–1115, 1102–1116, 1103–1117, 1104–1118, 1105–1119, 1106–1120, 1107–1121, 1108–1122, 1109–1123, 1110–1124, 1111–1125, 1112–1126, 1113–1127, 1114–1128, 1115–1129, 1116–1130, 1117–1131, 1118–1132, 1119–1133, 1120–1134, 1121–1135, 1122–1136, 1123–1137, 1124–1138, 1125–1139, 1126–1140, 1127–1141, 1128–1142, 1129–1143, 1130–1144, 1131–1145, 1132–1146, 1133–1147, 1134–1148, 1135–1149, 1136–1150, 1137–1151, 1138–1152, 1139–1153, 1140–1154, 1141–1155, 1142–1156, 1143–1157, 1144–1158, 1145–1159, 1146–1160, 1147–1161, 1148–1162, 1149–1163, 1150–1164, 1151–1165, 1152–1166, 1153–1167, 1154–1168, 1155–1169, 1156–1170, 1157–1171, 1158–1172, 1159–1173, 1160–1174, 1161–1175, 1162–1176, 1163–1177, 1164–1178, 1165–1179, 1166–1180, 1167–1181, 1168–1182, 1169–1183, 1170–1184, 1171–1185, 1172–1186, 1173–1187, 1174–1188, 1175–1189, 1176–1190, 1177–1191, 1179–1192, 1179–1193, 1180–1194, 1181–1195, 1182–1196, 1183–1197, 1184–1198, 1185–1199, 1186–1200, 1187–1201, 1188–1202, 1189–1203, 1190–1204, 1191–1205, 1192–1206, 1193–1207, 1194–1208, 1195–1209, 1196–1210, 1197–1211, 1198–1212, 1199–1213, 1200–1214, 1201–1215, 1202–1216, 1203–1217, 1204–1218, 1705–1219, 1206–1220, 1207–1221, 1208–1222, 1209–1223, 1210–1224, 1211–1225, 1212–1226, 1213–1227, 1214–1228, 1215–1229, 1216–1230, 1217–1231, 1218–1232, 1219–1233, 1220–1234, 1221–1235, 1222–1236, 1223–1237, 1224–1238, 1225–1239, 1226–1240, 1227–1241, 1228–1242, 1229–1243, 1230–1244, 1231–1245, 1232–1246, 1233–1247, 1234–1248, 1235–1249, 1236–1250, 1237–1251, 1238–1252, 1239–1253, 1240–1254, 1241–1255, 1242–1256, 1243–1257, 1244–1258, 1245–1259, 1246–1260, 1247–1261, 1248–1262, 1249–1263, 1250–1264, 1251–1265, 1252–1266, 1253–1267, 1254–1268, 1255–1269, 1256–1270, 1257–1271, 1258–1272, 1259–1273, 1260–1274, 1261–1275, 1262–1276, 1263–1277, 1264–1278, 1265–1279, 1266–1280, 1267–1281, 1268–1282, 1269–1283, 1270–1284, 1271–1285, 1272–1286, 1273–1287, 1274–1288, 1275–1289, 1276–1290, 1277–1291, 1278–1292, 1279–1293, 1280–1294, 1281–1295, 1282–1296, 1283–1297, 1284–1298, 1285–1299, 1286–1300, 1287–1301, 1288–1302, 1289–1303, 1290–1304, 1291–1305,
1292–1306, 1293–1307, 1294–1308, 1295–1309,
1296–1310, 1297–1311, 1298–1312, 1299–1313,
1300–1314, 1301–1315, 1302–1315, 1303–1317,
1304–1318, 1305–1319, 1306–1320, 1307–1321,
1308–1322, 1309–1323, 1310–1324, 1311–1325,
1312–1326, 1313–1327, 1314–1328, 1315–1329,
1316–1330, 1317–1331, 1318–1332, 1319–1333,
1320–1334, 1321–1335, 1322–1336, 1323–1337,
1324–1338, 1325–1339, 1326–1340, 1327–1341,
1328–1342, 1329–1343, 1330–1344, 1331–1345,
1332–1346, 1333–1347, 1334–1348, 1335–1349,
1336–1350, 1337–1351, 1338–1352, 1339–1353,
1340–1354, 1341–1355, 1342–1356, 1343–1357,
1344–1358, 1345–1359, 1346–1360, 1347–1361,
1348–1362, 1349–1363, 1350–1364, 1351–1365,
1352–1366, 1353–1367, 1354–1368, 1355–1369,
1356–1370, 1357–1371, 1358–1372, 1359–1373,
1360–1374, 1361–1375, 1362–1376, 1363–1377,
1364–1378, 1365–1379, 1366–1380, 1367–1381,
1368–1382, 1369–1383, 1370–1384, 1371–1385,
1372–1386, 1373–1387, 1374–1388, 1375–1389,
1376–1390, 1377–1391, 1378–1392, 1379–1393,
1380–1394, 1381–1395, 1382–1396, 1383–1397,
1384–1398, 1385–1399, 1386–1400, 1387–1401,
1388–1402, 1389–1403, 1390–1404, 1391–1405,
1392–1406, 1393–1407, 1394–1408, 1395–1409,
1396–1410, 1397–1411, 1398–1412, 1399–1413,
1400–1414, 1401–1415, 1402–1416, 1403–1417,
1404–1418, 1405–1419, 1406–1420, 1407–1421,
1408–1422, 1409–1423, 1410–1424, 1411–1425,
1412–1426, 1413–1427, 1414–1428, 1415–1429,
1416–1430, 1417–1431, 1418–1432, 1419–1433,
1420–1434, 1421–1435, 1422–1436, 1423–1437,
1424–1438, 1425–1439, 1426–1440, 1427–1441,
1428–1442, 1429–1443, 1430–1444, 1431–1445,
1432–1446, 1433–1447, 1434–1448, 1435–1449,
1436–1450, 1437–1451, 1438–1452, 1439–1453,
1440–1454, 1441–1455, 1442–1456, 1443–1457,
1444–1458, 1445–1459, 1446–1460, 1447–1461,
1448–1462, 1449–1463, 1450–1464, 1451–1465,
1452–1466, 1453–1467, 1454–1468, 1455–1469,
1456–1470, 1457–1471, 1458–1472, 1459–1473,
1460–1474, 1461–1475, 1462–1476, 1463–1477,
1464–1478, 1465–1479, 1466–1480, 1467–1481,
1468–1482, 1469–1483, 1470–1484, 1471–1485,
1472–1486, 1473–1487, 1474–1488, 1475–1489,
1476–1490, 1477–1491, 1478–1492, 1479–1493,
1480–1494, 1481–1495, 1482–1496, 1483–1497,
1484–1498, 1485–1499, 1486–1500, 1487–1501,
1488–1502, 1489–1503, 1490–1504, 1491–1505,
1492–1506, 1493–1507, 1494–1508, 1495–1509,
1496–1510, 1497–1511, 1498–1513, 1499–1514,
1500–1515, 1501–1515, 1502–1516, 1503–1517,
1504–1518, 1505–1519, 1506–1520, 1507–1521,
1508–1522, 1509–1523, 1510–1524, 1511–1525,
1512–1526, 1513–1527, 1514–1528, 1515–1529,
1516–1530, 1517–1531, 1518–1532, 1519–1533,
1520–1534, 1521–1535, 1522–1536, 1523–1537,
1524–1538, 1525–1539, 1526–1540, 1527–1541,
1528–1542, 1529–1543, 1530–1544, 1531–1545,
1532–1546, 1533–1547, 1534–1548, 1535–1549,
1536–1550, 1537–1551, 1538–1552, 1539–1553,
1540–1554, 1541–1555, 1542–1556, 1543–1557,
1544–1558, 1545–1550, 1546–1560, 1547–1561,
1548–1562, 1549–1563, 1550–1564, 1551–1565,
1552–1566, 1553–1567, 1554–1568, 1555–1569,
1556–1570, 1557–1571, 1558–1572, 1559–1573,
1560–1574, 1561–1575, 1562–1576, 1563–1577,
1564–1578, 1555–1579, 1566–1580, 1567–1581,
1568–1582, 1569–1583, 1570–1584, 1571–1585,
1572–1586, 1573–1587, 1574–1588, 1575–1589,
1576–1590, 1577–1591, 1578–1592, 1579–1593,
1580–1594, 1581–1595, 1582–1596, 1583–1597,
1584–1598, 1585–1599, 1586–1600, 1587–1601,
1588–1602, 1589–1603, 1590–1604, 1591–1605,
1592–1606, 1593–1607, 1594–1608, 1593–1609,
1596–1610, 1597–1611, 1598–1612, 1599–1613,
1600–1614, 1601–1615, 1602–1616, 1603–1617,
1604–1618, 1605–1619, 1606–1620, 1607–1621,
1608–1622, 1609–1623, 1610–1624, 1611–1625,
1612–1626, 1613–1627, 1614–1628, 1615–1629,
1616–1630, 1617–1631, 1618–1632, 1619–1633,
1620–1634, 1621–1635, 1622–1636, 1623–1637,
1624–1638, 1625–1639, 1626–1640, 1627–1641,
1628–1642, 1629–1643, 1630–1644, 1631–1645,
1632–1646, 1633–1647, 1634–1648, 1635–1649,
1636–1650, 1637–1651, 1638–1652, 1639–1653,
1640–1654, 1641–1655, 1642–1656, 1643–1657,
1644–1658, 1645–1659, 1646–1660, 1647–1661,
1648–1662, 1649–1663, 1650–1664, 1651–1665,
1652–1666, 1653–1667, 1654–1668, 1655–1669,
1656–1670, 1657–1671, 1658–1672, 1659–1673,
1660–1674, 1661–1675, 1662–1676, 1663–1677,
1664–1678, 1665–1679, 1666–1680, 1667–1681,
1668–1682, 1669–1683, 1670–1684, 1671–1685,
1672–1686, 1673–1687, 1674–1688, 1675–1689,
1676–1690, 1677–1691, 1678–1692, 1679–1693,
1680–1694, 1681–1695, 1682–1696, 1683–1697,
1684–1698, 1685–1699, 1686–1700, 1687–1701,
1688–1702, 1689–1703, 1690–1704, 1691–1705,
1692–1706, 1693–1707, 1694–1708, 1695–1709,
1696–1710, 1697–1711, 1698–1712, 1699–1713,
1700–1714, 1701–1715, 1702–1716, 1703–1717,
1704–1718, 1705–1719, 1706–1720, 1707–1721,
1708–1722, 1709–1723, 1710–1724, 1711–1725,
1712–1726, 1713–1727, 1714–1728, 1715–1729,
1716–1730, 1717–1731, 1718–1732, 1719–1733,
1720–1734, 1721–1735, 1722–1736, 1723–1737,
1724–1738, 1725–1739, 1726–1740, 1777–1741,
1728–1742, 1729–1743, 1730–1744, 1731–1745,
1732–1746, 1733–1747, 1734–1748, 1735–1749,
1736–1750, 1737–1751, 1738–1752, 1739–1753,
1740–1754, 1741–1755, 1742–1756, 1743–1757,
1744–1758, 1745–1759, 1746–1760, 1747–1761,
1748–1762, 1749–1763, 1750–1764, 1751–1765,
1752–1766, 1753–1767, 1754–1768, 1755–1769,
1756–1770, 1757–1771, 1758–1772, 1759–1773,
1760–1774, 1761–1775, 1762–1776, 1763–1777,
1764–1778, 1765–1779, 1766–1780, 1767–1781,
1768–1782, 1760–1783, 1770–1784, 1711–1785,
1772–1786, 1773–1787, 1774–1788, 1775–1789,
1776–1790, 1777–1791, 1778–1792, 1779–1793,
1780–1794, 1781–1795, 1782–1796, 1783–1797,
1784–1798, 1785–1799, 1796–1800, 1787–1801,
1788–1802, 1789–1803, 1790–1804, 1791–1805,
1792–1806, 1793–1807, 1794–1808, 1795–1809,
1790–1810, 1797–1811, 1798–1812, 1799–1813,
1800–1814, 1801–1815, 1802–1816, 1803–1817,
1804–1818, 1805–1819, 1806–1820, 1807–1821,
1808–1822, 1809–1823, 1810–1824, 1811–1825,
1812–1826, 1813–1827, 1814–1828, 1815–1829,
1816–1830, 1817–1831, 1818–1832, 1819–1833,
1820–1834, 1821–1835, 1822–1836, 1823–1837, 1824–1838, 1825–1839, 1826–1840, 1827–1841, 1828–1842, 1829–1843, 1830–1844, 1831–1845, 1832–1846, 1833–1847, 1834–1848, 1835–1849, 1836–1850, 1837–1851, 1838–1852, 1839–1853, 1840–1854, 1841–1855, 1842–1856, 1843–1857, 1844–1858, 1845–1859, 1846–1860, 1947–1861, 1848–1862, 1849–1863, 1850–1864, 1851–1865, 1852–1866, 1853–1867, 1854–1868, 1855–1869, 1856–1870, 1857–1871, 1858–1872, 1859–1873, 1860–1874, 1861–1875, 1862–1876, 1863–1877, 1864–1878, 1865–1879, 1866–1880, 1867–1881, 1868–1882, 1869–1883, 1870–1884, 1871–1885, 1872–1886, 1873–1887, 1874–1888, 1875–1889, 1876–1890, 1877–1891, 1878–1892, 1879–1893, 1880–1894, 1881–1895, 1882–1896, 1883–1897, 1884–1898, 1885–1899, 1886–1900, 1887–1901, 1888–1902, 1889–1903, 1890–1904, 1891–1905, 1892–1906, 1893–1907, 1894–1908, 1895–1909, 1896–1910, 1897–1911, 1898–1912, 1899–1913, 1900–1914, 1901–1915, 1902–1916, 1903–1917, 1904–1918, 1905–1919, 1906–1920, 1907–1921, 1908–1922, 1909–1923, 1910–1924, 1911–1925, 1912–1926, 1913–1927, 1914–1928, 1915–1929, 1916–1930, 1917–1931, 1918–1932, 1919–1933, 1920–1934, 1921–1935, 3922–1936, 1923–1937, 1924–1938, 1925–1939, 1926–1940, 1927–1941, 1928–1942, 1929–1943, 1930–1944, 1931–1945, 1932–1946, 1933–1947, 1934–1948, 1935–1949, 1936–1950, 1937–1951, 1938–1952, 1939–1953, 1940–1954, 1941–1955, 1944–1956, 1943–1957, 1944–1958, 1945–1959, 1946–1960, 1947–1961, 1948–1962, 1949–1963, 1950–1964, 1951–1965, 1952–1966, 1953–1967, 1954–1968, 1955–1969, 1956–1970, 1957–1971, 1958–1972, 1959–1973, 1960–1974, 1961–1975, 1962–1976, 1963–1977, 1964–1978, 1965–1979, 1966–1980, 1967–1981, 1968–1982, 1969–1983, 1970–1984, 1971–1985, 1972–1986, 1973–1987, 1974–1988, 1975–1989, 1976–1990, 1977–1991, 1978–1992, 1979–1993, 1980–1994, 1981–1995, 1982–1996, 1983–1997, 1984–1998, 1985–1999, 1986–2000, 1987–2001, 1988–2002, 1989–2003, 1990–2004, 1991–2005, 1992–2006, 1993–2007, 1994–2008, 1995–2009, 1996–2010, 1997–2011, 1998–2012, 1999–2013, 2000–2014, 2001–2015, 2002–2016, 2003–2017, 2004–2018, 2005–2019, 2006–2020, 2007–2021, 2008–2022, 2009–2023, 2010–2024, 2011–2025, 2012–2026, 2013–2027, 2014–2028, 2015–2029, 2016–2030, 2017–2031, 2018–2032, 2019–2033, 2020–2034, 2021–2035, 2022–2036, 2023–2037, 2024–2038, 2025–2039, 2026–2040, 2027–2041, 2028–2042, 2029–2043, 2030–2044, 2031–2045, 2032–2046, 2033–2047, 2034–2048, 2035–2049, 2036–2050, 2037–2051, 2038–2052, 2039–2053, 2040–2054, 2041–2055, 2042–2056, 2043–2057, 2044–2058, 2045–2059, 2046–2060, 2047–2061, 2048–2062, 2049–2063, 2050–2064, 2051–2065, 2052–2066, 2053–2067, 2054–2068, 2055–2069, 2056–2070, 2057–2071, 2058–2072, 2059–2073, 2060–2074, 2061–2075, 2062–2076, 2063–2077, 2064–2078, 2065–2079, 2066–2080, 2067–2081, 2068–2082, 2069–2083, 2070–2084, 2071–2085, 2072–2086, 2073–2087, 2074–2088, 2075–2089, 2076–2090, 2077–2091, 2078–2092, 2079–2093, 2080–2094, 2081–2095, 2082–2096, 2083–2097, 2084–2098, 2085–2099, 2086–2100, 2097–2101, 2088–2102, 2089–2103, 2090–2104, 2091–2105, 2092–2106, 2093–2107, 2094–2108, 2095–2109, 2096–2110, 2097–2111, 2098–2112, 2099–2113, 2100–2114, 2101–2115, 2102–2116, 2103–2117, 2104–2118, 2105–2119, 2106–2120, 2107–2121, 2108–2122, 2109–2123, 2110–2124, 2111–2125, 2112–2126, 2113–2127, 2114–2128, 2115–2129, 2116–2130, 2117–2131, 2118–2132, 2119–2133, 2120–2134, 2121–2135, 2122–2136, 2123–2137, 2124–2138, 2125–2139, 2126–2140, 2127–2141, 2128–2142, 2129–2143, 2130–2144, 2131–2145, 2132–2146, 2133–2147, 2134–2148, 2135–2149, 2136–2150, 2137–2151, 2138–2132, 2139–2153, 2140–2154, 2141–2155, 2142–2156, 2143–2157, 2144–2158, 2145–2159, 2146–2160, 2147–2161, 2148–2162, 2149–2163, 2150–2164, 2151–2165, 2152–2166, 2153–2167, 2154–2168, 2155–2169, 2156–2170, 2157–2171, 2158–2112, 2159–2173, 2160–2174, 2161–2175, 2162–2176, 2163–2177, 2164–2178, 2165–2179, 2166–2180, 2167–2181, 2168–2182, 2169–2183, 2170–2184, 2171–2185, 2172–2186, 2173–2187, 2174–2188, 2175–2189, 2176–2190, 2177–2191, 2178–2192, 2179–2193, 2180–2194, 2181–2195, 2182–2196, 2183–2197, 2184–2198, 2185–2199, 2186–2200, 2187–2201, 2188–2202, 2189–2203, 2190–2204, 2191–2205, 2192–2206, 2193–2207, 2194–2208, 2195–2209, 2196–2210, 2197–2211, 2198–2212, 2199–2213, 2200–2214, 2201–2215, 2202–2216, 2203–2217, 2204–2218, 2205–2219, 2206–2220, 2207–2221, 2208–2222, 2209–2223, 2210–2224, 2211–2225, 2212–2226, 2213–2227, 2214–2228, 2215–2229, 2216–2230, 2217–2231, 2218–2232, 2219–2233, 2220–2234, 2221–2235, 2222–2236, 2223–2237, 2224–2238, 2225–2239, 2226–2240, 2227–2241, 2228–2242, 2229–2243, 2230–2244, 2231–2245, 2232–2246, 2233–2247, 2234–2248, 2235–2249, 2236–2250, 2237–2251, 2238–2252, 2239–2253, 2240–2254, 2241–2255, 2242–2256, 2243–2257, 2244–2258, 2245–2259, 2246–2260, 2247–2261, 2248–2262, 2249–2263, 2250–2264, 2251–2265, 2252–2266, 2253–2267, 2254–2268, 2255–2269, 2256–2270, 2257–2271, 2258–2272, 2259–2273, 2260–2274, 2261–2275, 2262–2276, 2263–2277, 2264–2278, 2265–2279, 2266–2280, 2267–2281, 2268–2282, 2269–2283, 2270–2284, 2271–2285, 2272–2286, 2273–2287, 2274–2288, 2275–2289, 2276–2290, 2277–2291, 2278–2292, 2279–2293, 2280–2294, 2281–2295, 2282–2296, 2283–2297, 2284–2298, 2285–2299, 2286–2300, 2287–2301, 2288–2302, 2289–2303, 2290–2304, 2291–2305, 2292–2306, 2293–2307, 2294–2308, 2295–2309, 2296–2310, 2297–2311, 2298–2312, 2299–2317, 2300–2314, 2301–2315, 2302–2315, 2303–2317, 2304–2318, 2305–2319, 2306–2320, 2307–2321, 2308–2322, 2309–2323, 2310–2324, 2311–2325, 2312–2326, 2313–2327, 2314–2328, 2315–2329, 2316–2330, 2317–2331, 2318–2332, 2319–2333, 2320–2334, 2321–2335, 2322–2336, 2323–2337, 2324–2338, 2325–2339, 2320–2340, 2327–2341, 2328–2342, 2329–2343, 2330–2344, 2331–2345, 2332–2346, 2333–2347, 2334–2348, 2335–2349, 2336–2350, 2337–2351, 2338–2352, 2339–2353, 2340–2354, 2341–2355, 2342–2356, 2343–2357, 2344–2358, 2345–2359, 2346–2360, 2347–2361, 2348–2362, 2349–2363, 2350–2364, 2351–2365, 2352–2366, 2353–2367, 2354–2368, 2355–2369, 2356–2370, 2357–2371, 2358–2372, 2359–2373, 2360–2374, 2361–2375, 2362–2376, 2363–2377,
2364–2378, 2365–2379, 2366–2380, 2367–2381,
2368–2382, 2369–2383, 2370–2384, 2371–2385,
2372–2386, 2373–2387, 2374–2388, 2375–2389,
2376–2390, 2377–2391, 2378–2392, 2379–2393,
2380–2394, 2381–2395, 2382–2396, 2383–2397,
2384–2398, 2385–2399, 2386–2400, 2387–2401,
2388–2402, 2389–2403, 2390–2404, 2391–2405,
2392–2406, 2393–2407, 2394–2408, 2395–2409,
2396–2410, 2397–2411, 2398–2412, 2399–2413,
2400–1412, 2401–2415, 2402–2416, 2403–2417,
2404–2418, 2405–2419, 2406–2420, 2407–2421,
2408–2422, 2409–2423, 2410–2424, 2411–2425,
2412–2426, 2413–2427, 2414–2428, 2415–2429,
2416–2430, 2417–2431, 2418–2432, 2419–2433,
2420–2434, 2421–2435, 2422–2436, 2423–2437,
2424–2438, 2425–2439, 2426–2440, 2427–2441,
2428–2442, 2429–2443, 2430–2444, 2431–2445,
2432–2446, 2433–2447, 2434–2448, 2435–2449,
2436–2450, 2437–2451, 2438–2452, 2439–2453,
2440–2454, 2441–2455, 2442–2456, 2443–2457,
2444–2458, 2445–2459, 2446–2460, 2447–2461,
2448–2462, 2449–2463, 2450–2464, 2451–2465,
2452–2466, 2453–2467, 2454–2468, 2455–2469,
2456–2470, 2457–2471, 2458–2472, 2459–2473,
2460–2474, 2461–2475, 2462–2476, 2463–2477,
2464–2478, 2465–2479, 2466–2480, 2467–2481,
2468–2482, 2469–2483, 2470–2484, 2471–2485,
2472–2486, 2473–2487, 2474–2488, 2475–2489,
2476–2490, 2477–2491, 2478–2492, 2479–2493,
2480–2494, 2481–2495, 2482–2496, 2483–2497,
2484–2498, 2485–2499, 2486–2500, 2487–2501,
2488–2502, 2489–2503, 2490–2504, 2491–2505,
2492–2506, 2493–2507, 2494–2508, 2495–2509,
2496–2510, 2497–2511, 2498–2513, 2499–2514,
2500–2515, 2501–2515, 2502–2516, 2503–2517,
2504–2518, 2505–2519, 2506–2520, 2507–2521,
2508–2522, 2509–2523, 2510–2524, 2511–2525,
2512–2526, 2513–2527, 2514–2528, 2515–2529,
2516–2530, 2517–2531, 2518–2532, 2519–2533,
2520–2534, 2521–2535, 2522–2536, 2523–2537,
2524–2538, 2525–2539, 2576–2540, 2527–2541,
2528–2542, 2529–2543, 2530–2544, 2531–2545,
2532–2546, 2533–2547, 2534–2548, 2535–2549,
2536–2550, 2537–2551, 2538–2552, 2539–2553,
2540–2554, 2541–2555, 2542–2556, 2543–2557,
2544–2558, 2545–2559, 2546–2560, 2547–2561,
2548–2562, 2549–2563, 2550–2564, 2551–2565,
2552–2566, 2553–2567, 2554–2568, 2555–2569,
2556–2570, 2557–2571, 2558–2572, 2559–2573,
2560–2574, 2561–2575, 2562–2576, 2563–2577,
2564–2578, 2565–2579, 2566–2580, 2567–2581,
2568–2582, 2569–2583, 2570–2584, 2571–2585,
2572–2586, 2573–2587, 2574–2588, 2575–2589,
2576–2590, 2577–2591, 2578–2592, 2579–2593,
2580–2594, 2581–2595, 2589–2596, 2583–2597,
2584–2598, 2585–2599, 2586–2600, 2587–2601,
2588–2602, 2589–2603, 2590–2604, 2591–2605,
2592–2606, 2593–2607, 2594–2608, 2595–2609,
2596–2610, 2597–2611, 2598–2612, 2599–2613,
2600–2614, 2601–2615, 2602–2616, 2603–2617,
2604–2618, 2605–2619, 2606–2620, 2607–2621,
2608–2622, 2609–2623, 2610–2624, 2611–2625,
2612–2626, 2613–2627, 2614–2628, 2615–2629,
2616–2630, 2617–2631, 2618–2632, 2619–2633,
2620–2634, 2621–2635, 2622–2636, 2623–2637,
2624–2638, 2625–2639, 2626–2640, 2627–2641,
2628–2642, 2629–2643, 2630–2644, 2631–2645,
2632–2646, 2633–2647, 2634–2648, 2635–2649,
2636–2650, 2637–2651, 2638–2652, 2639–2653,
2640–2654, 2641–2655, 2642–2656, 2643–2657,
2644–2658, 2645–2659, 2646–2660, 2647–2661,
2648–2652, 2649–2653, 2650–2664, 2651–2665,
2652–2666, 2653–2667, 2654–2668, 2655–2669,
2656–2670, 2657–2671, 2658–2672, 2659–2673,
2660–2674, 2661–2675, 2662–2676, 2663–2677,
2604–2678, 2665–2679, 2666–2680, 2667–2681,
2668–2682, 2069–2683, 2670–2684, 2671–2685,
2672–2686, 2673–2687, 2674–2688, 2675–2689,
2676–2690, 2677–2691, 2678–2692, 2679–2693,
2680–2694, 2681–2695, 2682–2696, 2683–2697,
2684–2698, 2685–2699, 2686–2700, 2687–2701,
2688–2702, 2689–2703, 2690–2704, 2691–2705,
2692–2706, 2693–2707, 2694–2708, 2695–2709,
2696–2710, 2697–2711, 2698–2712, 2699–2713,
2700–2714, 2701–2715, 2702–2716, 2703–2717,
2704–2718, 2705–2719, 2706–2720, 2707–2721,
2708–2722, 2709–2723, 2710–2724, 2711–2725,
2712–2726, 2713–2727, 2714–2728, 2715–2729,
2716–2730, 2717–2731, 2718–2732, 2719–2733,
2720–2734, 2721–2735, 2722–2736, 2723–2737,
2724–2738, 2725–2739, 2726–2740, 2727–2741,
2728–2742, 2729–2743, 2730–2744, 2731–2745,
2732–2746, 2733–2747, 2734–2748, 2735–2749,
2736–2750, 2737–2751, 2738–2752, 2739–2753,
2740–2754, 2741–2755, 2742–2756, 2743–2757,
2744–2758, 2745–2759, 2746–2760, 2747–2761,
2748–2762, 2749–2763, 2750–2764, 2751–2765,
2752–2766, 2753–2767, 2754–2768, 2755–2769,
2756–2770, 2757–2771, 2758–2772, 2759–2773,
2760–2774, 2761–2775, 2762–2776, 2763–2777,
2764–2778, 2765–2779, 2766–2780, 2767–2781,
2768–2782, 2769–2783, 2770–2784, 2771–2785,
2772–2786, 2773–2787, 2774–2788, 2775–2789,
2776–2790, 2777–2791, 2778–2792, 2779–2793,
2780–2794, 2781–2795, 2782–2796, 2783–2797,
2794–2798, 2785–2799, 2786–2800, 2787–2801,
2788–2802, 2789–2803, 2790–2804, 2791–2805,
2792–2806, 2793–2807, 2794–2808, 2795–2809,
2796–2810, 2797–2811, 2798–2812, 2799–2813,
2800–2814, 2801–2815, 2802–2816, 2803–2817,
2804–2818, 2805–2819, 2806–2820, 2807–2821,
2808–2822, 2809–2823, 2810–2824, 2811–2825,
2812–2826, 2813–2827, 2814–2828, 2815–2829,
2816–2830, 2817–2831, 2818–2832, 2819–2833,
2820–2834, 2821–2835, 2822–2836, 2823–2837,
2824–2838, 2825–2839, 2826–2840, 2827–2841,
2828–2842, 2829–2843, 2830–2844, 2831–2845,
2832–2846, 2833–2847, 2834–2848, 2835–2849,
2836–2850, 2837–2851, 2838–2852, 2839–2853,
2840–2854, 2841–2855, 2842–2856, 2843–2857,
2844–2858, 2845–2859, 2846–2860, 2847–2861,
2848–2862, 2849–2863, 2850–2864, 2851–2865,
2852–2866, 2853–2867, 2854–2868, 2855–2869,
2856–2870, 2855–2871, 2858–2872, 2859–2873,
2860–2874, 2861–2875, 2862–2876, 2863–2877,
2864–2878, 2865–2879, 2866–2880, 2867–2881,
2868–2882, 2869–2883, 2870–2884, 2871–2885,
2872–2886, 2873–2887, 2874–2888, 2875–2889,
2876–2890, 2877–2891, 2878–2892, 2879–2893,
2880–2894, 2881–2895, 2882–2896, 2883–2897,
2884–2898, 2885–2899, 2886–2900, 2887–2901,
2888–2902, 2889–2903, 2890–2904, 2891–2905,
2892–2906, 2893–2907, 2894–2908, 2895–2909, 2896–2910, 2897–2911, 2898–2912, 2899–2913,
2900–2914, 2901–2915, 2902–2916, 2903–2917,
2904–2918, 2905–2919, 2906–2920, 2907–2921,
2908–2922, 2909–2923, 2910–2924, 2911–2925,
2912–2926, 2913–2927, 2914–2928, 2915–2929,
2916–2930, 2917–2931, 2918–2932, 2919–2933,
2920–2934, 2921–2935, 2922–2936, 2923–2937,
2924–2938, 2925–2939, 2926–2940, 2927–2941,
2928–2942, 2929–2943, 2930–2944, 2931–2945,
2932–2946, 2933–2947, 2934–2948, 2935–2949,
2936–2950, 2937–2951, 2938–2952, 2939–2953,
2940–2954, 2941–2955, 2942–2956, 2943–2957,
2944–2958, 2945–2959, 2946–2960, 2947–2961,
2948–2962, 2949–2963, 2950–2964, 2951–2965,
2952–2966, 2953–2967, 2954–2968, 2955–2969,
2956–2970, 2957–2971, 2958–2972, 2959–2973,
2960–2974, 2961–2975, 2962–2976, 2963–2977,
2964–2978, 2965–2979, 2966–2980, 2967–2981,
2968–2982, 2969–2983, 2970–2984, 2971–2985,
2972–2986, 2973–2987, 2974–2988, 2975–2989,
2976–2990, 2977–2991, 2978–2992, 2979–2993,
2980–2994, 2981–2995, 2982–2996, 2983–2997,
2984–2998, 2985–2999, 2986–3000, 2987–3001,
2988–3002, 2989–3003, 2990–3004, 2991–3005,
2992–3006, 2993–3007, 2994–3008, 2995–3009,
2996–3010, 2997–3011, 2998–3012, 2999–3013,
3000–3014, 3001–3015, 3002–3016, 3003–3017,
3004–3018, 3005–3019, 3006–3020, 3007–3021,
3008–3022, 3009–3023, 3010–3024, 3011–3025,
3012–3026, 3013–3027, 3014–3028, 3015–3029,
3016–3030, 3017–3031, 3018–3032, 3019–3033,
3020–3034, 3021–3035, 3022–3036, 3023–3037,
3024–3038, 3025–3039, 3026–3040, 3027–3041,
3028–3042, 3029–3043, 3030–3044, 3031–3045,
3032–3046, 3033–3047, 3034–3048, 3035–3049,
3036–3050, 3037–3051, 3038–3052, 3039–3053,
3040–3054, 3041–3055, 3042–3056, 3043–3057,
3044–3058, 3045–3059, 3046–3060, 3047–3061,
3048–3062, 3049–3063, 3050–3064, 3051–3065,
3052–3066, 3053–3067, 3054–3068, 3055–3069,
3056–3070, 3057–3071, 3058–3072, 3059–3073,
3060–3074, 3061–3075, 3062–3076, 3063–3077,
3064–3078, 3065–3079, 3066–3080, 3067–3081,
3068–3082, 3069–3083, 3070–3084, 3071–3085,
3072–3086, 3073–3087, 3074–3088, 3075–3089,
3076–3090, 3077–3091, 3078–3092, 3079–3093,
3080–3094, 3081–3095, 3082–3096, 3083–3097,
3084–3098, 3085–3099, 3086–3100, 3087–3101,
3088–3102, 3089–3103, 3090–3104, 3091–3105,
3092–3106, 3093–3107, 3094–3108, 3095–3109,
3096–3110, 3097–3111, 3098–3112, 3099–3113,
3100–3114, 3101–3115, 3102–3116, 3103–3117,
3104–3118, 3105–3119, 3106–3120, 3107–3121,
3108–3122, 3109–3123, 3110–3124, 3111–3125,
3112–3126, 3113–3127, 3114–3128, 3115–3129,
3116–3130, 3117–3131, 3118–3132, 3119–3133,
3120–3134, 3121–3135, 3122–3136, 3123–3137,
3124–3138, 3125–3139, 3126–3140, 3127–3141,
3128–3142, 3129–3143, 3130–3144, 3131–3145,
3132–3146, 3133–3147, 3134–3148, 3135–3149,
3136–3150, 3137–3151, 3138–3152, 3139–3153,
3140–3154, 3141–3155, 3142–3156, 3143–3157,
3144–3158, 3145–3159, 3146–3160, 3147–3161,
3148–3162, 3149–3163, 3150–3164, 3151–3165,
3152–3166, 3153–3167, 3154–3168, 3155–3169,
3156–3170, 3157–3171, 3158–3172, 3159–3173,
3160–3174, 3161–3175, 3162–3176, 3163–3177,
3164–3178, 3165–3179, 3166–3180, 3167–3181,
3168–3182, 3169–3183, 3170–3184, 3171–3185,
3172–3186, 3173–3187, 3174–3188, 3175–3189,
3176–3190, 3177–3191, 3178–3192, 3179–3193,
3180–3194, 3181–3195, 3182–3196, 3183–3197,
3184–3198, 3185–3199, 3186–3200, 3187–3201,
3188–3202, 3189–3203, 3190–3204, 3191–3205,
3192–3206, 3103–3207, 3194–3208, 3195–3209,
3196–3210, 3197–3211, 3198–3212, 3199–3213,
3200–3214, 3201–3215, 3202–3216, 3203–3217,
3204–3218, 3205–3219, 3206–3220, 3207–3221,
3208–3222, 3209–3223, 3210–3224, 3211–3225,
3212–3226, 3213–3227, 3214–3228, 3215–3229,
3216–3230, 3211–3231, 3218–3232, 3219–3233,
3220–3234, 3221–3235, 3222–3236, 3223–3237,
3224–3238, 3225–3239, 3226–3240, 3227–3241,
3228–3242, 3229–3243, 3230–3244, 3231–3245,
3232–3246, 3233–3247, 3234–3248, 3235–3249,
3236–3250, 3237–3251, 3238–3252, 3239–3253,
3240–3254, 3241–3255, 3242–3256, 3243–3257,
3244–3258, 3245–3259, 3246–3260, 3247–3261,
3248–3262, 3249–3263, 3250–3264, 3251–3265,
3252–3266, 3253–3267, 3254–3268, 3255–3269,
3256–3270, 3257–3271, 3258–3272, 3259–3273,
3260–3274, 3261–3275, 3262–3276, 2763–3277,
3264–3278, 3265–3279, 3266–3280, 3267–3281,
3268–3282, 3269–3283, 3270–3284, 3271–3285,
3272–3286, 3273–3287, 3274–3288, 3275–3289,
3276–3290, 3277–3291, 3278–3292, 3279–3293,
3280–3294, 3281–3295, 3282–3296, 3283–3297,
3284–3298, 3285–3299, 3286–3300, 3287–3301,
3288–3302, 3289–3303, 3290–3304, 3291–3305,
3292–3306, 3293–3307, 3294–3308, 3295–3309,
3296–3310, 3297–3311, 3298–3312, 3299–3313,
3304–3314, 3301–3315, 3302–3316, 3303–3317,
3304–3318, 3305–3319, 3306–3320, 3307–3321,
3308–3322, 3309–3323, 3310–3324, 3311–3325,
3312–3326, 3313–3327, 3314–3328, 3315–3329,
3316–3330, 3317–3331, 3318–3332, 3319–3333,
3320–3334, 3321–3335, 3322–3336, 3323–3337,
3324–3338, 3325–3339, 3326–3340, 3327–3341,
3328–3342, 3329–3343, 3330–3344, 3331–3345,
3332–3346, 3333–3347, 3334–3348, 3335–3349,
3336–3350, 3337–3351, 3338–3352, 3339–3353,
3340–3354, 3341–3355, 3342–3356, 3343–3357,
3344–3358, 3345–3359, 3346–3360, 3347–3361,
3348–3362, 3349–3363, 3350–3364, 3351–3365,
3352–3366, 3353–3367, 3354–3368, 3355–3369,
3356–3370, 3357–3371, 3358–3372, 3359–3373,
3360–3374, 3361–3375, 3362–3376, 3363–3377,
3364–3378, 3365–3379, 3366–3380, 3367–3381,
3368–3382, 3369–3383, 3370–3384, 3371–3385,
3372–3386, 3373–3387, 3374–3388, 3375–3389,
3376–3390, 3377–3391, 3378–3392, 3379–3393,
3380–3394, 3381–3395, 3382–3396, 3383–3397,
3384–3398, 3385–3399, 3380–3400, 3387–3401,
3388–3402, 3389–3403, 3390–3404, 3391–3405,
3392–3406, 3393–3407, 3394–3408, 3395–3409,
3396–3410, 3397–3411, 3398–3412, 3399–3413,
3400–3414, 3401–3415, 3402–3416, 3403–3417,
3404–3418, 3405–3419, 3406–3420, 3407–3421,
3408–3422, 3409–3423, 3410–3424, 3411–3425,
3412–3426, 3413–3427, 3414–3428, 3415–3429,
3416–3430, 3417–3431, 3418–3432, 3419–3433,
3420–3434, 3421–3435, 3422–3436, 3423–3437,
3424–3438, 3425–3439, 3426–3440, 3427–3441,
3428–3442, 3429–3443, 3430–3444, 3431–3445, 3432–3446, 3433–3447, 3434–3448, 3435–3449,
3436–3450, 3437–3451, 3438–3452, 3439–3454,
3440–3454, 3441–3455, 3442–3456, 3443–3457,
3444–3458, 3445–3459, 3446–3460, 3447–3461,
3448–3462, 3449–3463, 3450–3464, 3451–3465,
3452–3466, 3453–3467, 3454–3468, 3455–3469,
3456–3470, 3457–3471, 3458–3472, 3459–3473,
3460–3474, 3461–3475, 3462–3476, 3463–3477,
3464–3478, 3465–3479, 3466–3480, 3467–3481,
3468–3482, 3469–3483, 3470–3484, 3471–3485,
3472–3486, 3473–3487, 3474–3488, 3475–3489,
3476–3490, 3477–3491, 3478–3492, 3479–3493,
3480–3494, 3481–3495, 3482–3496, 3483–3497,
3484–3498, 3435–3499, 3486–3500, 3487–3501,
3488–3502, 3489–3503, 3490–3504, 3491–3505,
3492–3506, 3493–3507, 3494–3508, 3495–3509,
3496–3510, 3497–3511, 3498–3513, 3499–3514,
3500–3515, 3501–3515, 3502–3516, 3503–3517,
3504–3518, 3505–3519, 3506–3520, 3507–3521,
3508–3522, 3509–3523, 3510–3524, 3511–3525,
3512–3526, 3513–3527, 3514–3528, 3515–3529,
3516–3530, 3317–3531, 3518–3532, 3519–3533,
3520–3534, 3521–3535, 3522–3536, 3523–3537,
3524–3538, 3525–3539, 3526–3540, 3527–3541,
3528–3542, 3529–3543, 3530–3544, 3531–3545,
3532–3546, 3533–3547, 3534–3548, 3535–3549,
3536–3550, 3537–3551, 3538–3552, 3539–3553,
3540–3554, 3541–3555, 3542–3556, 3543–3557,
3544–3558, 3545–3559, 3546–3560, 3547–3561,
3548–3562, 3549–3563, 3550–3564, 3551–3565,
3552–3566, 3553–3567, 3554–3568, 3555–3569,
3556–3570, 3557–3571, 3558–3572, 3559–3573,
3560–3574, 3561–3575, 3562–3576, 3563–3577,
3564–3578, 3565–3579, 3566–3580, 3567–3581,
3568–3582, 3569–3583, 3570–3584, 3571–3585,
3572–3586, 3573–3587, 3574–3588, 3575–3589,
3576–3590, 3577–3591, 3578–3592, 3579–3593,
3580–3594, 3581–3595, 3582–3596, 3583–3597,
3584–3598, 3585–3599, 3586–3600, 3587–3601,
3588–3602, 3589–3603, 3590–3604, 3591–3605,
3592–3606, 3593–3607, 3594–3608, 3595–3609,
3596–3610, 3597–3611, 3598–3612, 3599–3613,
3600–3614, 3601–3615, 3602–3616, 3603–3617,
3604–3618, 3605–3619, 3606–3620, 3607–3621,
3608–3622, 3609–3623, 3610–3624, 3611–3625,
3612–3626, 3613–3627, 3614–3628, 3615–3629,
3616–3630, 3617–3631, 3618–3632, 3619–3633,
3620–3634, 3621–3635, 3622–3636, 3623–3637,
3624–3638, 3625–3639, 3626–3640, 3627–3641,
3628–3642, 3629–3643, 3630–3644, 3631–3645,
3632–3646, 3633–3647, 3634–3648, 3637–3649,
3636–3650, 3637–3651, 3638–3652, 3639–3653,
3640–3654, 3641–3655, 3642–3656, 3643–3657,
3644–3658, 3645–3659, 3646–3660, 3647–3661,
3648–3662, 3649–3663, 3650–3664, 3651–3665,
3652–3666, 3653–3667, 3654–3668, 3655–3669,
3656–3670, 3657–3671, 3658–3672, 3659–3673,
3660–3674, 3661–3675, 3662–3676, 3663–3677,
3664–3678, 3665–3679, 3666–3680, 3667–3681,
3668–3682, 3669–3683, 3670–3684, 3671–3685,
3672–3686, 3673–3687, 3674–3688, 3675–3689,
3676–3690, 3677–3691, 3678–3692, 3679–3693,
3680–3694, 3681–3695, 3682–3696, 3683–3697,
3684–3698, 3685–3699, 3686–3700, 3687–3701,
3688–3702, 3689–3703, 3690–3704, 3691–3705,
3692–3706, 3693–3707, 3694–3708, 3695–3709,
3696–3710, 3697–3711, 3698–3712, 3699–3713,
3700–3714, 3701–3715, 3702–3716, 3703–3717,
3704–3718, 3705–3719, 3706–3720, 3707–3721,
3708–3722, 3709–3723, 3710–3724, 3711–3725,
3712–3726, 3713–3727, 3714–3728, 3715–3729,
3716–3730, 3717–3731, 3718–3732, 3719–3733,
3720–3734, 3721–3735, 3722–3736, 3723–3737,
3724–3738, 3725–3739, 3726–3740, 3727–3741,
3728–3742, 3729–3743, 3730–3744, 3731–3745,
3732–3746, 3733–3747, 3734–3748, 3735–3749,
3736–3750, 3737–3751, 3738–3752, 3739–3753,
3740–3754, 3741–3755, 3742–3756, 3743–3757,
3744–3758, 3745–3759, 3746–3760, 3747–3761,
3748–3762, 3749–3763, 3750–3764, 3751–3765,
3752–3766, 3753–3767, 3754–3768, 3755–3769,
3756–3770, 3757–3771, 3758–3772, 3759–3773,
3760–3774, 3761–3775, 3762–3776, 3763–3777,
3764–3778, 3765–3779, 3766–3780, 3767–3781,
3768–3782, 3769–3783, 3770–3784, 3771–3785,
3772–3786, 3773–3787, 3774–3788, 3775–3789,
3776–3790, 3777–3791, 3778–3792, 3779–3793,
3780–3794, 3781–3795, 3782–3796, 3783–3797,
3784–3798, 3785–3799, 3786–3800, 3787–3801,
3788–3802, 3789–3803, 3790–3804, 3791–3805,
3792–3806, 3793–3807, 3794–3808, 3795–3809,
3796–3810, 3797–3811, 3798–3812, 3799–3813,
3800–3814, 3801–3815, 3802–3816, 3803–3817,
3804–3818, 3805–3819, 3806–3820, 3807–3821,
3808–3822, 3809–3823, 3810–3824, 3811–3825,
3812–3826, 3813–3827, 3814–3828, 3815–3829,
3816–3830, 3817–3831, 3818–3832, 3819–3833,
3820–3834, 3821–3835, 3822–3836, 3823–3837,
3824–3838, 3825–3839, 3826–3840, 3827–3841,
3828–3842, 3829–3843, 3830–3844, 3831–3845,
3832–3846, 3833–3847, 3834–3848, 3835–3849,
3836–3850, 3837–3851, 3838–3852, 3839–3853,
3840–3854, 3841–3855, 3842–3856, 3843–3857,
3844–3858, 3845–3859, 3846–3860, 3847–3861,
3848–3862, 3849–3863, 3850–3864, 3851–3865,
3852–3866, 3853–3867, 3854–3868, 3855–3869,
3856–3870, 3857–3871, 3858–3872, 3859–3873,
3860–3874, 3861–3875, 3862–3876, 3863–3877,
3864–3878, 3865–3879, 3866–3880, 3867–3881,
3868–3882, 3869–3883, 3870–3884, 3871–3885,
3872–3886, 3873–3887, 3874–3888, 3875–3889,
3876–3890, 3877–3891, 3878–3892, 3879–3893,
3880–3894, 3881–3895, 3882–3896, 3883–3897,
3884–3898, 3885–3899, 3886–3900, 3887–3901,
3888–3902, 3889–3903, 3890–3904, 3891–3905,
3892–3906, 3893–3907, 3894–3908, 3895–3909,
3896–3910, 3897–3911, 3898–3912, 3899–3913,
3900–3914, 3901–3915, 3902–3916, 3903–3917,
3904–3918, 3905–3919, 3906–3920, 3907–3921,
3908–3922, 3909–3923, 3910–3924, 3911–3925,
3912–3926, 3913–3927, 3914–3928, 3915–3929,
3916–3930, 3917–3931, 3918–3932, 3919–3933,
3920–3934, 3921–3935, 3922–3936, 3923–3937,
3924–3938, 3925–3939, 3926–3940, 3927–3941,
3929–3942, 3929–3943, 3930–3944, 3931–3945,
3932–3946, 3933–3947, 3934–3948, 3935–3949,
3936–3950, 3937–3951, 3908–3952, 3939–3953,
3940–3954, 3941–3955, 3942–3956, 3943–3957,
3944–3958, 3945–3959, 3946–3960, 3947–3961,
3948–3962, 3949–3963, 3950–3964, 3951–3965,
3952–3966, 3953–3967, 3954–3968, 3955–3969,
3956–3970, 3957–3971, 3958–3972, 3959–3973,
3960–3974, 3961–3975, 3962–3976, 3963–3977,
3964–3978, 3965–3979, 3966–3980, 3967–3981, 3968–3982, 3969–3983, 3970–3984, 3971–3985,
3972–3986, 3973–3987, 3974–3988, 3975–3989,
3976–3990, 3977–3991, 3978–3992, 3979–3993,
3980–3994, 3981–3995, 3982–3996, 3983–3997,
3984–3998, 3985–3999, 3986–4000, 3987–4001,
3988–4002, 3989–4003, 3990–4004, 3991–4005,
3992–4006, 3993–4007, 3994–4008, 3995–4009,
3996–4010, 3997–4011, 3998–4012, 3999–4013,
4000–4014, 4001–4015, 4002–4016, 4003–4017,
4004–4018, 4005–4019, 4006–4020, 4007–4021,
4008–4022, 4009–4023, 4010–4024, 4011–4025,
4012–4026, 4013–4027, 4014–4028, 4015–4029,
4016–4030, 4017–4031, 4018–4032, 4019–4033,
4020–4034, 4021–4035, 4022–4036, 4023–4037,
4024–4038, 4025–4039, 4026–4040, 4027–4041,
4028–4042, 4029–4043, 4030–4044, 4031–4045,
4032–4046, 4033–4047, 4034–4048, 4035–4049,
4036–4050, 4037–4051, 4038–4052, 4039–4053,
4040–4054, 4041–4055, 4042–4056, 4043–4057,
4044–4058, 4045–4059, 4040–4060, 4047–4061,
4048–4062, 4049–4063, 4050–4064, 4051–4065,
4052–4066, 4053–4067, 4054–4068, 4055–4069,
4056–4070, 4057–4071, 4058–4072, 4059–4073,
4060–4074, 4061–4075, 4062–4076, 4063–4077,
4064–4078, 4065–4079, 4066–4080, 4067–4081,
4068–4082, 4069–4083, 4070–4084, 4071–4085,
4072–4086, 4073–4087, 4074–4088, 4075–4089,
4076–4090, 4077–4091, 4078–4092, 4079–4093,
4080–4094, 4081–4095, 4082–4096, 4083–4097,
4084–4098, 4085–4099, 4086–4100, 4087–4101,
4088–4102, 4089–4103, 4090–4104, 4091–4105,
4092–4106, 4093–4107, 4094–4108, 4095–4109,
4096–4110, 4097–4111, 4098–4112, 4099–4113,
4100–4114, 4101–4115, 4102–4116, 4103–4117,
4104–4118, 4105–4119, 4106–4120, 4107–4121,
4108–4122, 4109–4123, 4110–4124, 4111–4125,
4119–4126, 4113–4127, 4114–4128, 4115–4129,
4116–4130, 4117–4131, 4118–4132, 4119–4133,
4120–4134, 4121–4135, 4122–4136, 4123–4137,
4124–4138, 4125–4139, 4126–4140, 4127–4141,
4128–4142, 4129–4143, 4130–4144, 4131–4145,
4132–4146, 4133–4147, 4134–4148, 4135–4149,
4136–4150, 4137–4151, 4138–4152, 4139–4153,
4140–4154, 4141–4155, 4142–4156, 4143–4157,
4144–4158, 4145–4159, 4146–4160, 4147–4161,
4148–4162, 4149–4163, 4150–4164, 4151–4165,
4152–4166, 4153–4167, 4154–4168, 4155–4169,
4156–4170, 4157–4171, 4158–4172, 4159–4173,
4160–4174, 4161–4175, 4162–4176, 4163–4177,
4164–4178, 4165–4179, 4166–4180, 4167–4181,
4168–4182, 4169–4183, 4170–4184, 4171–4185,
4172–4186, 4173–4187, 4174–4188, 4175–4189,
4176–4190, 4177–4191, 4178–4192, 4179–4193,
4180–4194, 4181–4195, 4182–4196, 4183–4197,
4184–4198, 4185–4199, 4186–4200, 4187–4201,
4188–4202, 4189–4203, 4190–4204, 4191–4205,
4192–4206, 4193–4207, 4194–4208, 4195–4209,
4196–4210, 4197–4211, 4198–4212, 4199–4213,
4200–4214, 4201–4215, 4202–4216, 4203–4217,
4204–4218, 4205–4219, 4206–4220, 4207–4221,
4208–4222, 4209–4223, 4210–4224, 4211–4225,
4212–4226, 4213–4227, 4214–4228, 4215–4229,
4216–4230, 4217–4231, 4218–4232, 4219–4232,
4220–4234, 4221–4235, 4222–4236, 4223–4237,
4224–4238, 4225–4239, 4226–4240, 4227–4241,
4228–4242, 4229–4243, 4230–4244, 4231–4245,
4232–4246, 4233–4247, 4234–4248, 4235–4249,
4236–4250, 4237–4251, 4238–4252, 4239–4253,
4240–4254, 4241–4255, 4242–4256, 4243–4257,
4244–4258, 4245–4759, 4246–4260, 4247–4261,
4248–4262, 4249–4263, 4250–4264, 4251–4265,
4252–4266, 4253–4267, 4254–4268, 4255–4269,
4256–4270, 4257–4271, 4258–4272, 4259–4273,
4260–4274, 4261–4275, 4262–4276, 4263–4277,
4264–4278, 4265–4279, 4266–4280, 4267–4281,
4268–4282, 4269–4283, 4270–4284, 4271–4285,
4272–4286, 4273–4287, 4274–4288, 4275–4289,
4276–4290, 4277–4291, 4278–4292, 4279–4293,
4280–4294, 4281–4295, 4282–4296, 4283–4297,
4284–4298, 4285–4299, 4286–4300, 4287–4301,
4288–4302, 4289–4303, 4290–4304, 4291–4305,
4292–4306, 4293–4307, 4294–4308, 4295–4309,
4296–4310, 4297–4311, 4298–4312, 4299–4313,
4300–4314, 4301–4315, 4302–4316, 4303–4317,
4304–4318, 4305–4319, 4306–4320, 4307–4321,
4308–4322, 4309–4323, 4310–4324, 4311–4325,
4312–4326, 4313–4327, 4314–4328, 4315–4329,
4316–4330, 4317–4331, 4318–4332, 4319–4333,
4320–4334, 4321–4335, 4322–4336, 4323–4337,
4324–4338, 4325–4339, 4326–4340, 4327–4341,
4328–4342, 4329–4343, 4330–4344, 4331–4345,
4332–4346, 4333–4347, 4334–4348, 4335–4349,
4336–4350, 4337–4351, 4338–4352, 4339–4353,
4340–4354, 4341–4355, 4342–4356, 4343–4357,
4344–4358, 4345–4359, 4346–4360, 4347–4361,
4348–4362, 4349–4363, 4350–4364, 4351–4365,
4352–4366, 4353–4367, 4354–4368, 4355–4369,
4356–4370, 4357–4371, 4358–4372, 4359–4373,
4360–4374, 4361–4375, 4362–4376, 4363–4377,
4364–4378, 4365–4379, 4366–4380, 4367–4381,
4368–4382, 4369–4383, 4370–4384, 4371–4385,
4372–4386, 4373–4387, 4374–4388, 4375–4389,
4376–4390, 4377–4391, 4378–4392, 4379–4393,
4380–4394, 4381–4395, 4382–4396, 4383–4397,
4384–4398, 4385–4399, 4386–4400, 4387–4401,
4388–4402, 4389–4403, 4390–4404, 4391–4405,
4392–4406, 4393–4407, 4394–4408, 4395–4409,
4396–4410, 4397–4411, 4398–4412, 4399–4413,
4400–4414, 4401–4415, 4402–4416, 4403–4417,
4404–4418, 4405–4419, 4406–4420, 4407–4421,
4408–4422, 4409–4423, 4410–4424, 4411–4425,
4412–4426, 4413–4427, 4414–4428, 4415–4429,
4416–4430, 4417–4431, 4418–4432, 4419–4433,
4420–4434, 4421–4435, 4422–4436, 4423–4437,
4424–4438, 4425–4439, 4426–4440, 4427–4441,
4428–4442, 4429–4443, 4430–4444, 4431–4445,
4432–4446, 4433–4447, 4434–4448, 4435–4449,
4436–4450, 4437–4451, 4438–4452, 4439–4453,
4440–4454, 4441–4455, 4442–4456, 4443–4457,
4444–4458, 4445–4459, 4446–4460, 4447–4461,
4448–4462, 4449–4463, 4450–4464, 4151–4465,
4452–4466, 4453–4467, 4454–4468, 4455–4469,
4456–4470, 4457–4471, 4458–4472, 4459–4473,
4460–4474, 4461–4475, 4462–4476, 4463–4477,
4464–4478, 4465–4479, 4466–4480, 4467–4481,
4468–4482, 4469–4483, 4470–4484, 4471–4485,
4472–4486, 4473–4487, 4474–4488, 4475–4489,
4476–4490, 4477–4491, 4478–4492, 4479–4493,
4480–4494, 4481–4495, 4482–4496, 4483–4497,
4484–4498, 4485–4499, 4486–4500, 4487–4501,
4488–4502, 4489–4503, 4490–4504, 4491–4505,
4492–4506, 4493–4507, 4494–4508, 4495–4509,
4496–4510, 4497–4511, 4498–4513, 4499–4514,
4500–4515, 4501–4515, 4502–4516, 4503–4517, 4504–4518, 4505–4519, 4506–4520, 4507–4521, 4508–4522, 4509–4523, 4510–4524, 4511–4525, 4512–4526, 4513–4527, 4514–4528, 4515–4529, 4516–4530, 4517–4531, 4518–4532, 4519–4533, 4520–4534, 4521–4535, 4522–4536, 4523–4537, 4524–4538, 4525–4539, 4526–4540, 4527–4541, 4528–4542, 4529–4543, 4530–4544, 4531–4545, 4532–4546, 4533–4547, 4534–4548, 4535–4549, 4536–4550, 4537–4551, 4538–4552, 4539–4553, 4540–4534, 4541–4555, 4542–4556, 4543–4557, 4544–4558, 4545–4559, 4546–4560, 4547–4561, 4548–4562, 4549–4563, 4550–4564, 4551–4565, 4552–4566, 4553–4567, 4554–4568, 4555–4569, 4556–4570, 4557–4571, 4558–4572, 4559–4573, 4560–4574, 4561–4575, 4562–4576, 4563–4577, 4564–4578, 4565–4579, 4566–4580, 4567–4581, 4568–4582, 4569–4583, 4570–4584, 4571–4585, 4572–4586, 4573–4587, 4574–4588, 4575–4589, 4576–4590, 4577–4591, 4578–4592, 4579–4593, 4580–4594, 4581–4595, 4582–4596, 4583–4597, 4584–4598, 4585–4599, 4586–4600, 4587–4601, 4588–4602, 4589–4603, 4590–4604, 4591–4605, 4592–4606, 4593–4607, 4594–4608, 4595–4609, 4596–4610, 4597–4611, 4598–4612, 4599–4613, 4600–4614, 4601–4615, 4602–4616, 4603–4617, 4604–4618, 4605–4619, 4606–4620, 4607–4621, 4608–4622, 4609–4623, 4610–4624, 4611–4625, 4612–4626, 4613–4627, 4614–4628, 4615–4629, 4616–4630, 4617–4631, 4618–4632, 4619–4633, 4620–4634, 4621–4635, 4622–4636, 4623–4637, 4624–4638, 4625–4639, 4626–4640, 4627–4641, 4628–4642, 4629–4643, 4630–4644, 4631–4645, 4632–4646, 4633–4647, 4634–4648, 4635–4649, 4636–4650, 4637–4651, 4638–4652, 4639–4653, 4640–4654, 4641–4655, 4642–4656, 4643–4657, 4644–4658, 4645–4659, 4646–4660, 4647–4661, 4648–4662, 4649–4663, 4650–4664, 4651–4665, 4652–4666, 4653–4667, 4654–4668, 4655–4669, 4656–4670, 4657–4671, 4658–4672, 4659–4673, 4660–4674, 4661–4675, 4662–4676, 4663–4677, 4664–4678, 4665–4679, 4666–4680, 4667–4681, 4668–4682, 4669–4683, 4670–4684, 4671–4685, 4672–4686, 4673–4687, 4674–4688, 4675–4689, 4676–4690, 4677–4691, 4678–4692, 4679–4693, 4680–4694, 4681–4695, 4682–4696, 4683–4697, 4684–4698, 4685–4699, 4686–4700, 4687–4701, 4688–4702, 4689–4703, 4690–4704, 4691–4705, 4692–4706, 4693–4707, 4694–4708, 4695–4709, 4696–4710, 4697–4711, 4698–4712, 4699–4713, 4700–4714, 4701–4715, 4702–4716, 4703–4717, 4704–4718, 4705–4719, 4706–4720, 4707–4721, 4708–4722, 4709–4723, 4710–4724, 4711–4725, 4712–4726, 4713–4727, 4714–4728, 4715–4729, 4716–4730, 4717–4731, 4718–4732, 4719–4733, 4720–4734, 4721–4735, 4722–4736, 4723–4737, 4724–4738, 4725–4739, 4726–4740, 4727–4741, 4728–4742, 4729–4743, 4730–4744, 4731–4745, 4732–4746, 4733–4747, 4734–4748, 4735–4749, 4736–4750, 4737–4751, 4738–4752, 4739–4753, 4740–4754, 4741–4755, 4742–4756, 4743–4757, 4744–4758, 4745–4759, 4746–4760, 4747–4761, 4748–4762, 4749–4763, 4750–4764, 4751–4765, 4752–4766, 4753–4767, 4754–4768, 4755–4769, 4756–4770, 4757–4771, 4758–4772, 4759–4773, 4760–4774, 4761–4775, 4762–4776, 4763–4777, 4764–4778, 4765–4779, 4766–4780, 4767–4781, 4768–4782, 4769–4783, 4770–4784, 4771–4785, 4772–4786, 4773–4787, 4774–4788, 4775–4789, 4776–4790, 4777–4791, 4778–4792, 4779–4793, 4780–4794, 4781–4795, 4782–4796, 4783–4797, 4784–4798, 4785–4799, 4786–4800, 4787–4801, 4788–4802, 4789–4803, 4790–4804, 4791–4805, 4792–4806, 4793–4807, 4794–4808, 4795–4809, 4796–4810, 4797–4811, 4798–4812, 4799–4813, 4800–4814, 4801–4815, 4802–4816, 4803–4817, 4804–4818, 4805–4819, 4806–4820, 4807–4821, 4808–4822, 4809–4823, 4810–4824, 4811–4825, 4812–4826, 4813–4827, 4814–4828, 4815–4829, 4816–4830, 4817–4831, 4818–4832, 4819–4833, 4820–4834, 4821–4835, 4822–4836, 4823–4837, 4824–4838, 4825–4839, 4826–4840, 4827–4841, 4828–4842, 4829–4843, 4830–4844, 4831–4845, 4832–4846, 4833–4847, 4834–4848, 4835–4849, 4836–4850, 4837–4851, 4838–4852, 4839–4853, 4840–4854, 4841–4855, 4842–4856, 4843–4857, 4844–4858, 4845–4859, 4846–4860, 4847–4861, 4848–4862, 4849–4863, 4850–4864, 4851–4865, 4852–4866, 4853–4867, 4854–4868, 4855–4869, 4856–4870, 4857–4871, 4858–4872, 4859–4873, 4860–4874, 4861–4875, 4862–4876, 4863–4877, 4864–4878, 4865–4879, 4866–4880, 4867–4881, 4868–4882, 4869–4883, 4870–4884, 4871–4885, 4872–4886, 4873–4887, 4874–4888, 4875–4889, 4876–4890, 4877–4891, 4878–4892, 4879–4893, 4880–4894, 4881–4895, 4882–4896, 4883–4897, 4884–4898, 4885–4899, 4886–4900, 4887–4901, 4888–4902, 4889–4903, 4890–4904, 4891–4905, 4892–4906, 4893–4907, 4894–4908, 4895–4909, 4896–4910, 4897–4911, 4898–4912, 4899–4913, 4900–4914, 4901–4915, 4902–4916, 4903–4917, 4904–4918, 4905–4919, 4906–4920, 4907–4921, 4908–4922, 4909–4923, 4910–4924, 4911–4925, 4912–4926, 4913–4927, 4914–4928, 4915–4929, 4916–4930, 4917–4931, 4918–4932, 4919–4933, 4920–4934, 4921–4935, 4922–4936, 4923–4937, 4924–4938, 4925–4939, 4926–4940, 4927–4941, 4928–4942, 4929–4943, 4930–4944, 4931–4945, 4932–4946, 4933–4947, 4934–4948, 4935–4949, 4936–4950, 4937–4951, 4938–4952, 4939–4953, 4940–4954, 4941–4955, 4942–4956, 4943–4957, 4944–4958, 4945–4959, 4046–4960, 4947–4961, 4948–4962, 4949–4963, 4950–4964, 4951–4965, 4952–4966, 4953–4967, 4954–4968, 4955–4969, 4956–4970, 4957–4971, 4958–4972, 4959–4973, 4960–4974, 4961–4975, 4962–4976, 4963–4977, 4964–4978, 4965–4979, 4966–4980, 4967–4981, 4968–4982, 4969–4983, 4970–4984, 4971–4985, 4972–4986, 4973–4987, 4974–4988 and 4975–4989 of SEQ ID NO:3.

EXAMPLE 9

Inhibition of IGF-I Binding by Antisense Oligonucleotides to IGF-I Receptor

Sub-confluent HaCaT cells were treated as described above with phosphorothioate oligonucleotides IGFR.AS (antisense: 5'-ATCTCTCCGCTTCCC-3'; [SEQ ID NO. 10]; ref 13) and IGFR.S (sense control: 5'-GAAAGGAAGCGGAGAGAT-3'; [SEQ ID NO. 11]; ref 13) IGF-I binding to the cell monolayers was then measured as $^{125}$I-IGF-I.

EXAMPLE 10

Inhibition of IGFBP-3 Production Using Antisense Oligonucleotides

Figure 7:
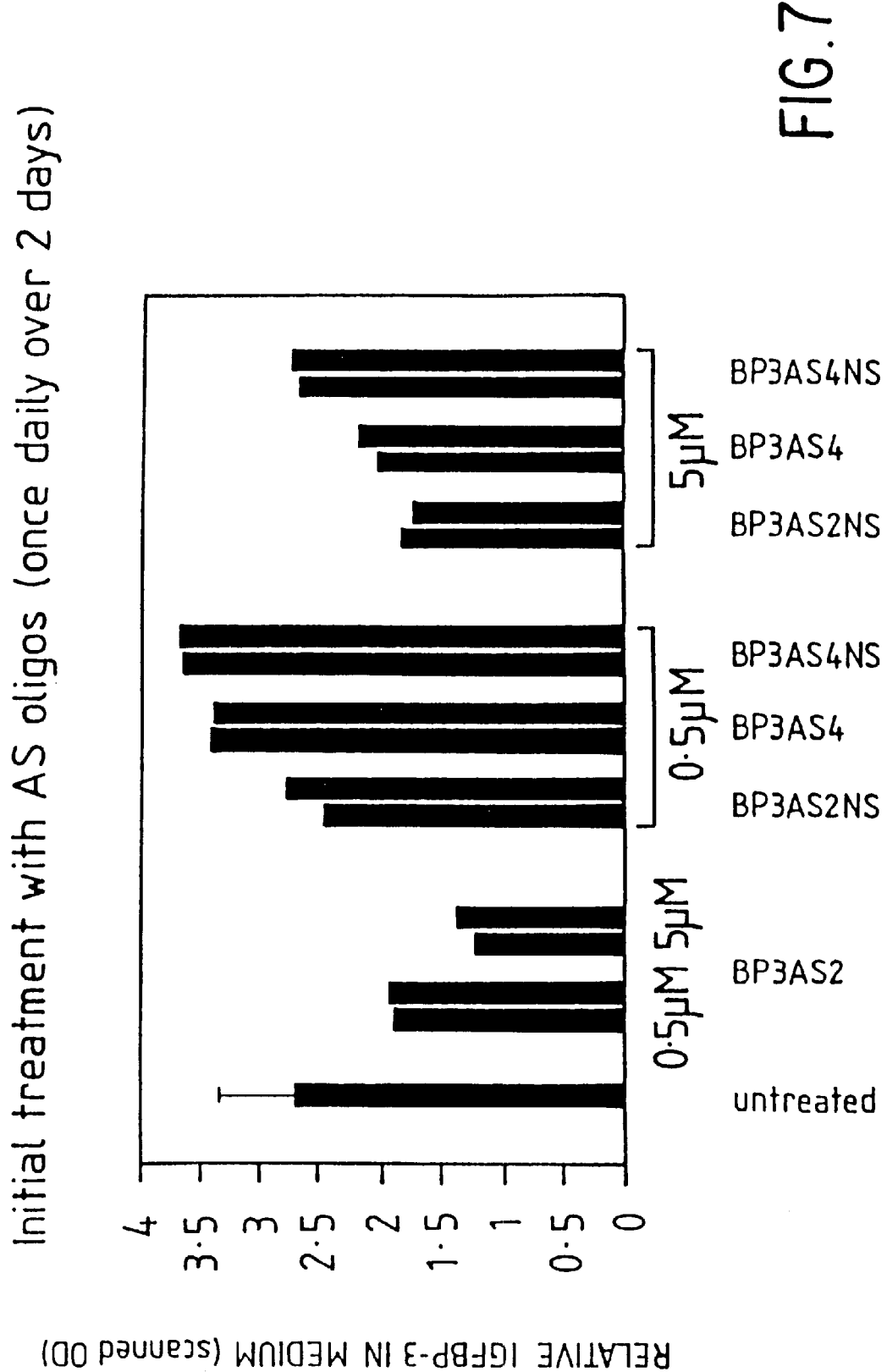
FIG. 7 is a graphical representation showing inhibition of IGFBP-3 production in culture medium following initial treatment with antisense oligonucleotides once daily over a 2 day period.
Figure 8:
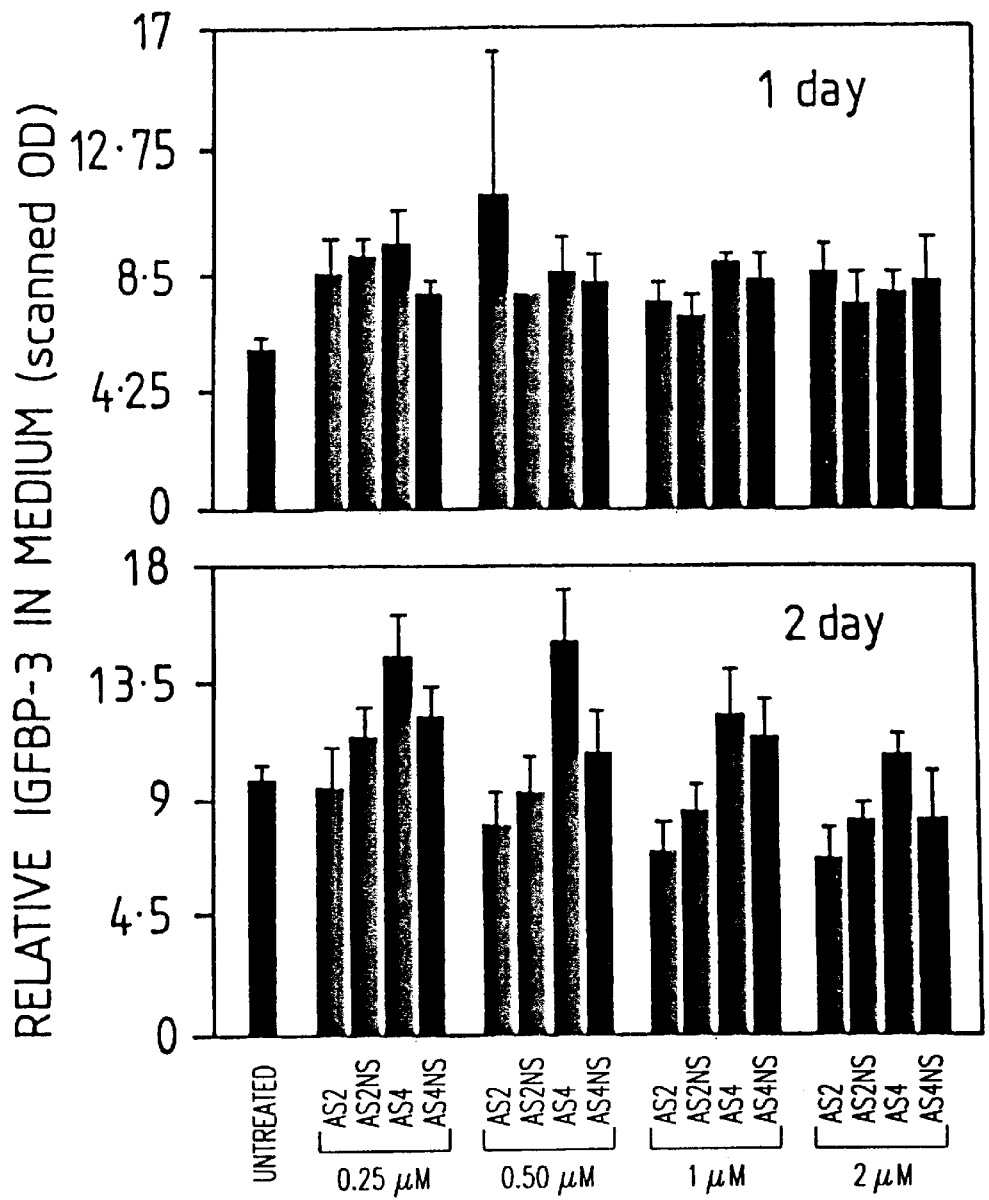
FIG. 8 is a graphical representation showing optimization of IGFBP-3 antisense oligonucleotide concentration as determined by relative IGFBP-3 concentration in culture medium.

The results of this experiment are shown in FIGS. 7 and 8.

HaCaT cells were initially plated in DMEM with 10% v/v serum, then AS oligo experiments were performed in complete "Keratinocyte-SFM" (Gibco) to exclude the influence of exogenous IGFBPs. Oligos were synthesised as phosphorothioate (nuclease-resistant) derivatives (Bresatec, South Australia) and were as follows: antisense: AS2, (SEQ ID NO:4) 5'-GCGCCCGCTGCATGACGCCTGCAAC-3' (IGFBP-3 start codon); controls: AS2NS (SEQ ID NO:8), 5'-CGGAGATGCCGCATGCCAGCGCAGG-3'; AS4 (SEQ ID NO:6), 5'-AGGCGGCTGACGGCACTA-3'; AS4NS (SEQ ID NO:9), 5'-GACAGCGTCGGAGCGATC-3'; IGFRAS (SEQ ID NO:10), 5'-ATCTCTCCGCTTCCTTTC-3'; IGFRS (SEQ ID NO:11), 5'-GAAAGGAAGCGGAGAGAT-3'. Oligos to IGFBP-3 were based on the published sequence of Spratt et al [12]. AS oligos were added to HaCaT monolayers in 0.5 ml medium in 24-well plates at the concentrations and addition frequencies indicated. IGFBP-3 measured in cell-conditioned medium using a dot-blot assay, adapted from the Western ligand blot method of Hossenlopp et al [11], in which 100 μl of conditioned medium was applied to nitrocellulose filters with a vacuum dot-blot apparatus. After drying the membranes at 37° C., relative amounts of IGFBP are determined by $^{125}$I-IGF-I-binding, autoradiography and computerised imaging densitometry. Triplicate wells (except in FIG. 7, where duplicate wells were measured as shown) were analysed and corrected for changes in cell number per well. Relative cell number per well was determined using an amido black dye method, developed specifically for cultured monolayers of HaCaT cells (14). Cell numbers differed by less than 10% after treatment. For oligos to the IGF receptor, receptor quantitation in intact HaCaT monolayers was by overnight incubation with $^{125}$I-IGF-I (30,000cpm/well) at 4° C.

EXAMPLE 11

Inhibition of IGFBP-2 Production Using Ribozymes

Experiments involving ribozymes are generally conducted as described in Internaitonal Patent Application No. WO 89/05852 and in Haselhoff and Gerlach [8]. Ribozymes are constructed with a hybridising region which is complementary in nucleotide sequence to at least part of a target RNA which, in this case, encodes IGFBP-2. Activity of ribozymes is measurable on, for example, Northern blots or using animal models such as in the nude mouse model (15; 16) or the "flaky skin" mouse model (17; 18).

EXAMPLE 12

Inhibition of IGFBP-3 Production Using Ribozymes

The methods described in Example 11 are used for the screening of ribozymes which inhibit IGFBP-3 production. The activity of the ribozymes is determined as in Example 11.

EXAMPLE 13

Inhibition of IGF-1 Production Using Ribozymes

The methods described in Example 11 are used for the screening of ribozymes which inhibit IGF-1 production. The activity of the ribozymes is determined as in Example 11.

EXAMPLE 14

Inhibition of IGF-1 Receptor Production Using Ribozymes

The methods described in Example 11 are used for the screening of ribozymes which inhibit IGF-1 production. The activity of the ribozymes is determined as in Example 11.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Sara V *Physiological Reviews* 70: 591–614, 1990.
2. Rechler M M and Brown A L *Growth Regulation* 2: 55–68, 1992.
3. Clemmons D R *Growth Regn* 2: 80, 1992.
4. Oakes S R, K M Haynes, M J Waters, A C Herington and G A Werther *J. Clin Endocrinol Metab* 73: 1368–1373, 1992.
5. Camacho-Hubner C et al. *J Biol Chem* 267: 11949–11956, 1992.
6. Neely K E et al. *J Inv Derm* 96: 104, 1991.
7. Ts'O P O P, Aurelian L, Chang E and Miller P S. Nonionic oligonucleotide analogs (Matagen T M) as anticodic agents in duplex and triplex formation in "Antisense Strategies", Annals of the New York Academy of Sciences 660:159–177 (Baserga R and Denhardt D T, eds.), 1993.
8. Haseloff J and Gerlach L *Nature* 334: 586–591, 1988.
9. Boukamp P, Petrussevska R T, Breitkreuz D, Hornung J, Markham A, Fusenig N E. *J Cell Biol* 106: 761–771, 1988.
10. Rheinwald and Green *Cell* 6: 331–344, 1975.
11. Hossenlopp P, Seurin D, Segovia-Quinson B, Hardouin S, Binoux M. *Anal Biochem* 154: 138–143, 1986.
12. Spratt S K, Tatsuno G P, Yamanaka M K, Ark B C, Detmer J, Mascarenhas D, Flynn J, Talkington-Verser C, Spencer E M. *Growth Factors* 3: 63–72, 1990.
13. Pietrzkowski, Z, Sell C, Lammers R, Ullrich A and Baserga R. *Mol. Cell. Biol.* 12: 3883–3889, 1992.
14. Schulz J, Dettlaff S, Fritzsche U, Harms U, Schiebel H, Derer W, Fusenig N E, Hulsen A and Bohm M. *J. Immunol. Meth.* 167: 1–13, 1994.
15. Baker B S, Brent L, Valdimarsson H, Powles A V, Al-Imara L, Walker M and Fry L. *Brit. J. Bermatol* 126: 105–110, 1992.
16. Nanney L B et al *J. Invest. Bermatol* 98: 296–301, 1992.
17. Sundberg J P et al *Immunol. Investigations* 22: 389–401, 1993.
18. Sundberg J P et al *J. Invest. Dermatol* 102: 781–788, 1994.

What is claimed is:

1. A nucleic acid molecule comprising at least about 10 nucleotides that hybridizes to or forms a heteroduplex with an mRNA molecule directed from a gene corresponding to a genomic form of SEQ ID NO:1 or SEQ ID NO:2 and which thereby reduces translation of said mRNA molecule.

2. A nucleic molecule according to claim 1 wherein said molecule comprises at least about 15 nucleotides.

3. A nucleic acid molecule according to claim 2 wherein said molecule hybridizes to or forms a heteroduplex with at least one nucleotide sequence of about 15 nucleotides in length present as a contiguous sequence within SEQ ID NO:1 or SEQ. ID NO:2.

4. A ribozyme comprising a hybridising region and a catalytic region wherein the hybridising region is capable of hybridising to at least part of a target mRNA sequence transcribed from a genomic gene corresponding to SEQ ID NO:1 or SEQ ID NO:2 wherein said catalytic domain is capable of cleaving said target mRNA sequence to reduce or inhibit IGF-I mediated cell proliferation or inflammation.

5. A pharmaceutical composition for topical administration said composition comprising a nucleic acid molecule that inhibits or otherwise reduces IGF-1 mediated cell proliferation wherein said nucleic acid comprises at least about ten nucleotides and hybridizes to or forms a heteroduplex with an mRNA molecule directed from a gene encoding human IGFBP-2 or IGFBP-3, said composition further comprising one or more pharmaceutically acceptable carriers.

6. A pharmaceutical composition according to claim 5 wherein said antisense molecule hybridizes to or forms a duplex with at least one nucleotide sequence of about 15 nucleotides in length present as a contiguous sequence within SEQ ID NO:2.

\* \* \* \* \*